United States Patent
Waters et al.

(10) Patent No.: US 6,297,007 B1
(45) Date of Patent: Oct. 2, 2001

(54) METHOD FOR ISOLATION OF BIOSYNTHESIS GENES FOR BIOACTIVE MOLECULES

(75) Inventors: Barbara Waters, Delta; Vivian Miao, Surrey, both of (CA); Yap Wai Ho, Singapore (SG); Seow Kah Tong, Johor (MY)

(73) Assignee: Terragen Diversity Inc., Vancouver (CA)

( * ) Notice: Subject to any disclaimer, the term of this patent is extended or adjusted under 35 U.S.C. 154(b) by 0 days.

(21) Appl. No.: 08/861,774

(22) Filed: May 22, 1997

(51) Int. Cl.$^7$ ............... C12Q 1/68; C12P 19/34; C07H 21/04
(52) U.S. Cl. ............... 435/6; 435/6; 435/91.2; 435/172.1; 536/22.1; 536/24.3
(58) Field of Search ............... 435/91.2, 6, 172.1; 536/24.3, 22.1

(56) References Cited

U.S. PATENT DOCUMENTS

| 4,935,340 | * | 6/1990 | Baltz et al. ............... | 435/6 |
| 5,849,491 | | 12/1998 | Radomski et al. ............ | 435/6 |

FOREIGN PATENT DOCUMENTS

| WO87/03907 | | 7/1987 | (WO) . | |
| WO 97.12991 | * | 4/1997 | (WO) ............... | 435/91.2 |

OTHER PUBLICATIONS

Bibb et al., "Analysis of the nucleotide sequence of the Streptomyces glaucescens tcml genes provides key information about the enzymology of polyketide antibiotic biosynthesis", The EMBO journal, vol. 8 (9), pp. 2727–2736, Aug. 1989.*

Cortes et al., "An unusually large multifunctional polypeptide in the erythromycin producing polyketide synthase of Saccharopolyspora erythrae", Nature, vol. 348, pp. 176–178, Nov. 1990.*

Leskiw et al.,"Cloning and Nucleotide determinationof the isopenicillin N synthetase gene from Streptomyces clavuligerus", gene, vol. 62, pp. 187–196.*

Zenova et al., "Compatible culture of Actinomycestes and Algae", Biol. Nauki (MOSC), vol. 0 (5), pp. 73–78, Aug. 1980.*

Wipat et al., "Streptomyces marker plasmids for monitoring survival and spread of Streptomyces in soil", Applied and Environmental Microbiology, vol. 57 (11), pp. 3322–3329, Nov. 1991.*

Cortes, J., et al., "An unusually large multifunctional polypeptide in the erythromycin–producing polyketide synthase of *Saccharopolyspora erythraea*", Nature 348:176–178, Nov. 8, 1990.

Malpartida, F., et al., "Homology between Streptomyces genes coding for synthesis of different polyketides used to clone antibiotic biosynthetic genes", Nature 325;818–821, Feb. 26, 1987.

Katz, L. and S. Donadio, "Polyketide Synthesis: Prospects for Hybrid Antibiotics", Annu Rev. Microgiol. 47:875–912, 1993.

Turgay, K., et al., "Four homologous domains in the primary structure of GrsB are related to domains in a superfamily of adenylate–forming enzymes", Molecular Microbiology 6(18):2743–2744.

* cited by examiner

Primary Examiner—Jeffrey Fredman
Assistant Examiner—Arun Chakrabarti
(74) Attorney, Agent, or Firm—Pennie & Edmonds LLP

(57) ABSTRACT

Degenerate primers which hybridize with various classes of antibiotic biosynthesis genes were used to amplify fragments of DNA from soil and lichen extracts. Cloning and sequencing of the amplified products showed that these products included a variety of novel and previously uncharacterized antibiotic biosynthesis gene sequences, the products of which have the potential to be active as antibiotics, immunosuppressors, antitumor agents, etc. Thus, antibiotic biosynthesis genes can be recovered from soil or lichens by a combining a sample with a pair of amplification primers under conditions suitable for polymerase chain reaction amplification, wherein the primer set is a degenerate primer set selected to hybridize with conserved regions of known antibiotic biosynthetic pathway genes, for example Type I and Type II polyketide synthase genes, isopenicillin N synthase genes, and peptide synthetase genes; cycling the combined sample through a plurality of amplification cycles to amplify DNA complementary to the primer set; and isolating the amplified DNA.

16 Claims, No Drawings

```
                          SEQUENCE LISTING

<160> NUMBER OF SEQ ID NOS: 94

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 1
gcsrtsgacc cgcagcgcgc                                                    20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 2
gatsrcgtcc gcrttsgtsc c                                                  21

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: primer
<221> NAME/KEY: modified_base
<222> LOCATION: (14)
<223> OTHER INFORMATION: n=a, c, g or t
```

```
<400> SEQUENCE: 3
ctsacsksgg scgnacsgcs acscg                                      25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 4
gttsacsgcg tagaaccasg cgaa                                       24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: primer
<221> NAME/KEY: modified_base
<222> LOCATION: (9)
<223> OTHER INFORMATION: n=a, c, g or t
<221> NAME/KEY: modified_base
<222> LOCATION: (18)
<223> OTHER INFORMATION: n=a, c, g, or t

<400> SEQUENCE: 5
ttcggsggnt tccagwsngc satg                                       24

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: primer
<221> NAME/KEY: modified_base
<222> LOCATION: (14)
<223> OTHER INFORMATION: n=a, c, g or t
<221> NAME/KEY: modified_base
<222> LOCATION: (24)
<223> OTHER INFORMATION: n=a, c, g, or t

<400> SEQUENCE: 6
tcsaksagsg csansgastc gtancc                                     26

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 7
ggbtcsggst tyttctacgc                                            20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 8
cctsggtctg gwasagsacg                                            20

<210> SEQ ID NO 9
<211> LENGTH: 35
```

```
<212> TYPE: DNA
<213> ORGANISM: Artificial Sequence
<220> FEATURE:
<223> OTHER INFORMATION: Description of Artificial Sequence: primer

<400> SEQUENCE: 9
atctacacst csggcacsac sggcaagccs aaggg                              35

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: primer
<221> NAME/KEY: modified_base
<222> LOCATION: (3)
<223> OTHER INFORMATION: n=a, c , g or t
<221> NAME/KEY: modified_base
<222> LOCATION: (9)
<223> OTHER INFORMATION: n=a, c, g or t
<221> NAME/KEY: modified_base
<222> LOCATION: (12)
<223> OTHER INFORMATION: n=a, c, g, or t
<221> NAME/KEY: modified_base
<222> LOCATION: (19)
<223> OTHER INFORMATION: n=a, c, g, or t

<400> SEQUENCE: 10
awngagksnc cnccsrrsnm gaagaa                                       26

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: primer
<221> NAME/KEY: modified_base
<222> LOCATION: (3)
<223> OTHER INFORMATION: n=a, c, g or t
<221> NAME/KEY: modified_base
<222> LOCATION: (9)
<223> OTHER INFORMATION: n=a, c, g, or t
<221> NAME/KEY: modified_base
<222> LOCATION: (12)
<223> OTHER INFORMATION: n=a, c, g, or t
<221> NAME/KEY: modified_base
<222> LOCATION: (15)
<223> OTHER INFORMATION: n=a, c, g, or t
<221> NAME/KEY: modified_base
<222> LOCATION: (24)
<223> OTHER INFORMATION: n=a, c, g, or t

<400> SEQUENCE: 11
mgngargcny tngcnatgga yccncarcar mg                                32

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: primer
<221> NAME/KEY: modified_base
<222> LOCATION: (6)
<223> OTHER INFORMATION: n=a, c, g or t
<221> NAME/KEY: modified_base
<222> LOCATION: (9)
<223> OTHER INFORMATION: n=a, c, g, or t
<221> NAME/KEY: modified_base
<222> LOCATION: (15)
<223> OTHER INFORMATION: n=a, c, g, or t
<221> NAME/KEY: modified_base
<222> LOCATION: (18)
<223> OTHER INFORMATION: n=a, c, g, or t
```

```
<221> NAME/KEY: modified_base
<222> LOCATION: (21)
<223> OTHER INFORMATION: n=a, c, g, or t
<221> NAME/KEY: modified_base
<222> LOCATION: (24)
<223> OTHER INFORMATION: n=a, c, g, or t
<221> NAME/KEY: modified_base
<222> LOCATION: (30)
<223> OTHER INFORMATION: n=a, c, g, or t

<400> SEQUENCE: 12
ggrtcnccna rytgngtncc ngtnccrtgn gc                                       32

<210> SEQ ID NO 13
<211> LENGTH: 1206
<212> TYPE: DNA
<213> ORGANISM: Artificial Sequence
<220> FEATURE:
<223> OTHER INFORMATION: Description of Artificial Sequence: Clone ksfs

<400> SEQUENCE: 13
gcggtggacc cgcagcagcg cctcatgctg gagctggcct ggtccgcgct ggaaagcgca          60
ggtcatccgc cctcgatatt ccccggcctg atcgggtct atgtcggcat gaactggaat         120
cgctatcgcg cgaattgcat ttctgcacac cctgatgtgg tggagcgatt cggtgaattg        180
aacacagcgc tcgccaacga atacgacttt cttgctaccc gaatctccta caagctcaat       240
ctgcgcggtc ccagcgtcac tatcagcacc gcttgttcga cttccctggt tgccattgct      300
caggcttcgc aggcgttgct caactatgaa tgcgacattg ctttggctgg ggttgcctcc      360
ataaccgtgc ctgtcaatgc aggctacctc taccaagaaa ggtggcatgc tttcaccgaa     420
gggcattgtc ctacattcga tgccccagca cgggaccact tcaatgatgc ccctgtctc      480 cttttttgcgg gcctggaaaa cccatccagg agggggggggg gggccctcat acccggcctt     540
tcaagcggga acctctcaca ggaagcggat gtttcagccg aagggatgtt gaacattgac    600
gccggcagca cggggggacaa gttcagggat gggcgcgctt tgttgtatg gggggggcct    660 ggaagaagca ttcaagggac ggtgatcaaa cttaacccct tcattggcgg gtttgccgcg    720
gaacaaggac gggttcggac aaggcgagtt taccggcgcc caggcgtcaa tggtcagggc    780
ggagttcatt tcgctttggc ggtggagttt gcgggatatt cgaatcccgc aagcatcggg    840
atttcattcg aaaacccacg ggcacgggcg acgccattgg gcgatccgat agaagtggcc    900
gcgctaaaga tggttttttcg ccgacgctcg ttccagaggc gccgttgcgc ccttggatcg    960
gtcaagagtt gtgtcggaca cctggttcac gccgccggcg tgaccggatt tatcaaggct   1020
gtcttgtcgg tctaccacgg caagatcgca ccgacactgt ttttcgagaa agcaaatccg   1080
aggctcgggc tggaagacag tcctttctat gtcaatgccg gactcgagaa gtggacggcc   1140
gccgagcagc cacgccgcgc gggggtcagt gctttcgggg tcggtggcac caatgcgcac   1200
gcgatc                                                              1206

<210> SEQ ID NO 14
<211> LENGTH: 402
<212> TYPE: PRT
<213> ORGANISM: Artificial Sequence
<220> FEATURE:
<223> OTHER INFORMATION: Description of Artificial Sequence: Clone ksfs

<400> SEQUENCE: 14

Ala Val Asp Pro Gln Gln Arg Leu Met Leu Glu Leu Ala Trp Ser Ala
 1               5                  10                  15
```

-continued

Leu Glu Ser Ala Gly His Pro Pro Ser Ile Phe Pro Gly Leu Ile Gly
             20                  25                  30

Val Tyr Val Gly Met Asn Trp Asn Arg Tyr Arg Ala Asn Cys Ile Ser
         35                  40                  45

Ala His Pro Asp Val Val Glu Arg Phe Gly Glu Leu Asn Thr Ala Leu
 50                  55                  60

Ala Asn Glu Tyr Asp Phe Leu Ala Thr Arg Ile Ser Tyr Lys Leu Asn
 65                  70                  75                  80

Leu Arg Gly Pro Ser Val Thr Ile Ser Thr Ala Cys Ser Thr Ser Leu
                 85                  90                  95

Val Ala Ile Ala Gln Ala Ser Gln Ala Leu Leu Asn Tyr Glu Cys Asp
             100                 105                 110

Ile Ala Leu Ala Gly Val Ala Ser Ile Thr Val Pro Val Asn Ala Gly
         115                 120                 125

Tyr Leu Tyr Gln Glu Arg Trp His Ala Phe Thr Glu Gly His Cys Pro
     130                 135                 140

Thr Phe Asp Ala Pro Ala Arg Asp His Phe Asn Asp Ala Pro Cys Leu
145                 150                 155                 160

Leu Phe Ala Gly Leu Glu Asn Pro Ser Arg Arg Gly Gly Ala Leu
                 165                 170                 175

Ile Pro Gly Leu Ser Ser Gly Asn Leu Ser Gln Glu Ala Asp Val Ser
             180                 185                 190

Ala Glu Gly Met Leu Asn Ile Asp Ala Gly Ser Thr Gly Asp Lys Phe
         195                 200                 205

Arg Asp Gly Arg Ala Phe Val Val Trp Gly Pro Gly Arg Ser Ile
     210                 215                 220

Gln Gly Thr Val Ile Lys Leu Asn Pro Phe Ile Gly Gly Phe Ala Ala
225                 230                 235                 240

Glu Gln Gly Arg Val Arg Thr Arg Arg Val Tyr Arg Arg Pro Gly Val
                 245                 250                 255

Asn Gly Gln Gly Gly Val His Phe Ala Leu Ala Val Glu Phe Ala Gly
             260                 265                 270

Tyr Ser Asn Pro Ala Ser Ile Gly Ile Ser Phe Glu Asn Pro Arg Ala
         275                 280                 285

Arg Ala Thr Pro Leu Gly Asp Pro Ile Glu Val Ala Ala Leu Lys Met
     290                 295                 300

Val Phe Arg Arg Arg Ser Phe Gln Arg Arg Cys Ala Leu Gly Ser
305                 310                 315                 320

Val Lys Ser Cys Val Gly His Leu Val His Ala Ala Gly Val Thr Gly
                 325                 330                 335

Phe Ile Lys Ala Val Leu Ser Val Tyr His Gly Lys Ile Ala Pro Thr
             340                 345                 350

Leu Phe Phe Glu Lys Ala Asn Pro Arg Leu Gly Leu Glu Asp Ser Pro
         355                 360                 365

Phe Tyr Val Asn Ala Gly Leu Glu Lys Trp Thr Ala Ala Glu Gln Pro
     370                 375                 380

Arg Arg Ala Gly Val Ser Ala Phe Gly Val Gly Gly Thr Asn Ala His
385                 390                 395                 400

Ala Ile

<210> SEQ ID NO 15
<211> LENGTH: 565
<212> TYPE: DNA
<213> ORGANISM: Artificial Sequence

```
<220> FEATURE:
<223> OTHER INFORMATION: Description of Artificial Sequence: Clone
      ipnsfs

<400> SEQUENCE: 15
ggctccgggt tttctacgc gtccaaccac gggatcgacg tcacgcgggt gcgcgacgag      60
gtgaacaagt tccacgccga gatgacgccc ggggagaagt tcgagctggc catcaacgcc    120
tacaacgacg cgaatccgca tacccgcaac gggtattaca tggccgtcga aggcaagaag    180
gccgtcgagt cctctgcta cctcaacccg gccttcaccc ccgagcaccc gatgatcgag     240
gcgggcgcgg cggggcacga ggtgaacaac tggccggacg aggctcgcca ccccggcttc    300
cgtgagtacg ggggagcagt acttcgaaga ggatcctccg acctgtcact ggtgctgctg    360
cgtgggtacg cgctggccct gggcaaggac gagaactact tcgacgacta cgtcaagcac    420
tccgacacgc tctcggccgt ctcgctgatc cgttacccgt acctggagaa ctacccgccg    480
gtgaagaccg gtccggacgg cgagaagctc agcttcgagg atcacttcga cgtctcgctg    540
atcaccgtgc tcttccagac ccagg                                         565

<210> SEQ ID NO 16
<211> LENGTH: 188
<212> TYPE: PRT
<213> ORGANISM: Artificial Sequence
<220> FEATURE:
<223> OTHER INFORMATION: Description of Artificial Sequence: Clone
      ipnsfs

<400> SEQUENCE: 16

Gly Ser Gly Phe Phe Tyr Ala Ser Asn His Gly Ile Asp Val Thr Arg
  1               5                  10                  15

Val Arg Asp Glu Val Asn Lys Phe His Ala Glu Met Thr Pro Gly Glu
                 20                  25                  30

Lys Phe Glu Leu Ala Ile Asn Ala Tyr Asn Asp Ala Asn Pro His Thr
             35                  40                  45

Arg Asn Gly Tyr Tyr Met Ala Val Glu Gly Lys Lys Ala Val Glu Ser
         50                  55                  60

Phe Cys Tyr Leu Asn Pro Ala Phe Thr Pro Glu His Pro Met Ile Glu
 65                  70                  75                  80

Ala Gly Ala Ala Gly His Glu Val Asn Asn Trp Pro Asp Glu Ala Arg
                 85                  90                  95

His Pro Gly Phe Arg Glu Tyr Gly Gly Ala Val Leu Arg Arg Gly Ser
                100                 105                 110

Ser Asp Leu Ser Leu Val Leu Leu Arg Gly Tyr Ala Leu Ala Leu Gly
            115                 120                 125

Lys Asp Glu Asn Tyr Phe Asp Asp Tyr Val Lys His Ser Asp Thr Leu
        130                 135                 140

Ser Ala Val Ser Leu Ile Arg Tyr Pro Tyr Leu Glu Asn Tyr Pro Pro
145                 150                 155                 160

Val Lys Thr Gly Pro Asp Gly Glu Lys Leu Ser Phe Glu Asp His Phe
                165                 170                 175

Asp Val Ser Leu Ile Thr Val Leu Phe Gln Thr Gln
            180                 185

<210> SEQ ID NO 17
<211> LENGTH: 1172
<212> TYPE: DNA
<213> ORGANISM: Artificial Sequence
<220> FEATURE:
```

<223> OTHER INFORMATION: Description of Artificial Sequence: Clone ps32

<400> SEQUENCE: 17

```
aaggaggggc cgcccggggc gaagaagctg tccgtccgac tgacacgttc cactccgagg      60
agcccggacc agatgcgcgc cagctttacc tcgaccggcg tagatggcgg gtcgtagtca     120
gtgcgatccg atgagtcatc tggaggtgca ggcagcacct tcagatcgat cttgccgctc     180
gccatgcgcg gcatctcgcg gagctcgacg aatgcagccg gaatcatgta ctcgggcaac     240
cgcgtgcgaa gatgatcgcg cagctcggac gcggcgaccg aggcgagccg aggcgaccag     300
tacgcaacga gacgcttgtc gccggcccgc tcctgccgcg ccaggacgac ggccgtctcg     360
acaccggggt gatcggccag cgccgcctcg atctcaccga gctcgatgcg gaagccgcgg     420
atcttgacct gatgatccgc gcgcccgatg aagtcgaggt tgccgtccgg aagccagcgc     480
accaggtcgc cggtccggta cagccgcgag ccaggtgcac cgaatggatc gggtacgaac     540
cgcgctccgg tgagggcggc atcatcgaca tagccgcgcg cgaggttctc gccaccgatg     600
tacagctcgc cgatcacgcg cgccggaacg ggctcgagtg cgctatcgag cacgtagacc     660
tgaacgttgt cgagcggacg gccgatcgac ggcagctcgg acccgtgttc ggacgcgggc     720
gacacgatcg cccacgtcgt atcgaccgcg ttctccgtcg ggccgtactc gttgagcatg     780
cggtagtgcg catcgcgcgg tggacgccgc gtgagtcgat caccgcccgt acgcagcacg     840
cgcaacgagc gtggaaagtc gccagccgcg agcaacgcgt cgagtagccg gcctggaaga     900
tcggagatcg tgatccccca tcgcgtcagg ttctcgagca ggcgcggcgg atcgaggcg      960
agctcgttgt ccaccagatg aagcgggcg cccgtcgcca gcgtggacca cagctcgagc    1020
gccgcggcat cgaacgacat cgagtagatc tgcgtcacgc ggtcgtcggc actgatctcg    1080
acggcacgct ggttccacgc gatcaaattt ctcagtgcac ggtgcggcac ggcgacgccc    1140
ttcggcttgc ccgtcgtgcc cgacgtgtag at                                  1172
```

<210> SEQ ID NO 18
<211> LENGTH: 390
<212> TYPE: PRT
<213> ORGANISM: Artificial Sequence
<220> FEATURE:
<223> OTHER INFORMATION: Description of Artificial Sequence: Clone ps32

<400> SEQUENCE: 18

```
Ile Tyr Thr Ser Gly Thr Thr Gly Lys Pro Lys Gly Val Ala Val Pro
  1               5                  10                  15

His Arg Ala Leu Arg Asn Leu Ile Ala Trp Asn Gln Arg Ala Val Glu
                 20                  25                  30

Ile Ser Ala Asp Asp Arg Val Thr Gln Ile Tyr Ser Met Ser Phe Asp
             35                  40                  45

Ala Ala Ala Leu Glu Leu Trp Ser Thr Leu Ala Thr Gly Ala Arg Leu
         50                  55                  60

His Leu Val Asp Asn Glu Leu Arg Leu Asp Pro Arg Leu Leu Glu
     65                  70                  75                  80

Asn Leu Thr Arg Trp Gly Ile Thr Ile Ser Asp Leu Pro Gly Arg Leu
                 85                  90                  95

Leu Asp Ala Leu Leu Ala Ala Gly Asp Phe Pro Arg Ser Leu Arg Val
                100                 105                 110

Leu Arg Thr Gly Gly Asp Arg Leu Thr Arg Arg Pro Pro Arg Asp Ala
            115                 120                 125
```

His Tyr Arg Met Leu Asn Glu Tyr Gly Pro Thr Glu Asn Ala Val Asp
    130                 135                 140

Thr Thr Trp Ala Ile Val Ser Pro Ala Ser Glu His Gly Ser Glu Leu
145                 150                 155                 160

Pro Ser Ile Gly Arg Pro Leu Asp Asn Val Gln Val Tyr Val Leu Asp
                165                 170                 175

Ser Ala Leu Glu Pro Val Pro Ala Arg Val Ile Gly Glu Leu Tyr Ile
            180                 185                 190

Gly Gly Glu Asn Leu Ala Arg Gly Tyr Val Asp Asp Ala Ala Leu Thr
        195                 200                 205

Gly Ala Arg Phe Val Pro Asp Pro Phe Gly Ala Pro Gly Ser Arg Leu
    210                 215                 220

Tyr Arg Thr Gly Asp Leu Val Arg Trp Leu Pro Asp Gly Asn Leu Asp
225                 230                 235                 240

Phe Ile Gly Arg Ala Asp His Gln Val Lys Ile Arg Gly Phe Arg Ile
                245                 250                 255

Glu Leu Gly Glu Ile Glu Ala Ala Leu Ala Asp His Pro Gly Val Glu
            260                 265                 270

Thr Ala Val Val Leu Ala Arg Gln Glu Arg Ala Gly Asp Lys Arg Leu
        275                 280                 285

Val Ala Tyr Trp Ser Pro Arg Leu Ala Ser Val Ala Ala Ser Glu Leu
    290                 295                 300

Arg Asp His Leu Arg Thr Arg Leu Pro Glu Tyr Met Ile Pro Ala Ala
305                 310                 315                 320

Phe Val Glu Leu Arg Glu Met Pro Arg Met Ala Ser Gly Lys Ile Asp
                325                 330                 335

Leu Lys Val Leu Pro Ala Pro Asp Ser Ser Asp Arg Thr Asp
            340                 345                 350

Tyr Asp Pro Pro Ser Thr Pro Val Glu Val Lys Leu Ala Arg Ile Trp
        355                 360                 365

Ser Gly Leu Leu Gly Val Glu Arg Val Ser Arg Thr Asp Ser Phe Phe
    370                 375                 380

Ala Pro Gly Gly Pro Ser
385                 390

<210> SEQ ID NO 19
<211> LENGTH: 472
<212> TYPE: DNA
<213> ORGANISM: Artificial Sequence
<220> FEATURE:
<223> OTHER INFORMATION: Description of Artificial Sequence: Clone clf

<400> SEQUENCE: 19

```
ttcggcgggt tccagacggc catggtgctg acgacgggac gggacaatga gaagtagcgt      60
cgcggtcacc ggcatcggcc tggtggccgc caacgggctc accaccgagg acgtgtggtc     120
ggccgtgctc ggcggccgca gcggccttgg aacgatcacc cgtttcgacg ccgcgggcta     180
cccggcccgg atcgcggcg aggtgtcgca gttcgtggcc gaggagcaca tcgccgaccg      240
gctgatcccg cagaccgacc acatgacccg gctggcgctg ccgcggccg agtcggcgat      300 ccgggacgcc aaggtgggac ctggccgagc tgcccgattc ggcgcgggcg tggtcaccgc     360
cgcgacggca ggcggcttcg agttcggcca gcgggagctg gagaacctgt ggcgcaaggg     420
gcctgagcac gtcagcccct accagtcctt cgcctggttc tacgccgtca ac             472
```

```
<210> SEQ ID NO 20
<211> LENGTH: 142
<212> TYPE: PRT
<213> ORGANISM: Artificial Sequence
<220> FEATURE:
<223> OTHER INFORMATION: Description of Artificial Sequence: Clone clf

<400> SEQUENCE: 20

Met Arg Ser Ser Val Ala Val Thr Gly Ile Gly Leu Val Ala Ala Asn
 1               5                  10                  15

Gly Leu Thr Thr Glu Asp Val Trp Ser Ala Val Leu Gly Gly Arg Ser
                20                  25                  30

Gly Leu Gly Thr Ile Thr Arg Phe Asp Ala Ala Gly Tyr Pro Ala Arg
            35                  40                  45

Ile Ala Gly Glu Val Ser Gln Phe Val Ala Glu His Ile Ala Asp
    50                  55                  60

Arg Leu Ile Pro Gln Thr Asp His Met Thr Arg Leu Ala Leu Ala Ala
 65                 70                  75                  80

Ala Glu Ser Ala Ile Arg Asp Ala Lys Val Gly Pro Gly Arg Ala Ala
                85                  90                  95

Arg Phe Gly Ala Gly Val Val Thr Ala Ala Thr Ala Gly Gly Phe Glu
            100                 105                 110

Phe Gly Gln Arg Glu Leu Glu Asn Leu Trp Arg Lys Gly Pro Glu His
        115                 120                 125

Val Ser Pro Tyr Gln Ser Phe Ala Trp Phe Tyr Ala Val Asn
    130                 135                 140

<210> SEQ ID NO 21
<211> LENGTH: 637
<212> TYPE: DNA
<213> ORGANISM: Xanthoparmelia cumberlandia

<400> SEQUENCE: 21
tatattactc caggttgctt acgaagcatt ggagatgtcc ggatatttcg ccgattcgtc      60
caggcctgag gatgtcggtt gctatattgg agcttgtgca acagattacg atttcaacgt     120
agcatcccat cctcccacgg cgtattcagc gactggcacg ctccgatctt ttctaagtgg     180
caagctgtcg cattactttg gttggtccgg tccctctctt gtcctagaca ctgcctgctc     240
ttcgtcggcg gtggctattc atactgcatg tactgctttg aggactggcc agtgttctca     300
agctctagca ggcgggatca cgttgatgac aagcccgtat ctctatgaga acttctctgc     360
agcccatttc ttgagtccaa cgggaggttc aaagccgttc agcgcagrtg cagatggata     420
ctgtagagga gaaggtggtg gcctcgtggt cttgaaacga cttcagatg ctctcaggga      480 tgatgaccat attattagtg tcatcgctgg ctcggcggtc aaccagaacg acaactgcgt     540
gcctatcacc gtccctcaca cttcgtctca gggaaatctc tatgaacgag ttaccagaca     600 ggcagggtg acacccaata aagtcacttt tgtggaa                               637

<210> SEQ ID NO 22
<211> LENGTH: 212
<212> TYPE: PRT
<213> ORGANISM: Xanthoparmelia cumberlandia
<220> FEATURE:
<221> NAME/KEY: SITE
<222> LOCATION: (136)
<223> OTHER INFORMATION: Xaa=unknown amino acid

<400> SEQUENCE: 22
```

```
Ile Leu Leu Gln Val Ala Tyr Glu Ala Leu Glu Met Ser Gly Tyr Phe
 1               5                  10                  15

Ala Asp Ser Ser Arg Pro Glu Asp Val Gly Cys Tyr Ile Gly Ala Cys
             20                  25                  30

Ala Thr Asp Tyr Asp Phe Asn Val Ala Ser His Pro Pro Thr Ala Tyr
         35                  40                  45

Ser Ala Thr Gly Thr Leu Arg Ser Phe Leu Ser Gly Lys Leu Ser His
     50                  55                  60

Tyr Phe Gly Trp Ser Gly Pro Ser Leu Val Leu Asp Thr Ala Cys Ser
 65                  70                  75                  80

Ser Ser Ala Val Ala Ile His Thr Ala Cys Thr Ala Leu Arg Thr Gly
                 85                  90                  95

Gln Cys Ser Gln Ala Leu Ala Gly Gly Ile Thr Leu Met Thr Ser Pro
            100                 105                 110

Tyr Leu Tyr Glu Asn Phe Ser Ala Ala His Phe Leu Ser Pro Thr Gly
        115                 120                 125

Gly Ser Lys Pro Phe Ser Ala Xaa Ala Asp Gly Tyr Cys Arg Gly Glu
    130                 135                 140

Gly Gly Gly Leu Val Val Leu Lys Arg Leu Ser Asp Ala Leu Arg Asp
145                 150                 155                 160

Asp Asp His Ile Ile Ser Val Ile Ala Gly Ser Ala Val Asn Gln Asn
                165                 170                 175

Asp Asn Cys Val Pro Ile Thr Val Pro His Thr Ser Ser Gln Gly Asn
            180                 185                 190

Leu Tyr Glu Arg Val Thr Arg Gln Ala Gly Val Thr Pro Asn Lys Val
        195                 200                 205

Thr Phe Val Glu
    210

<210> SEQ ID NO 23
<211> LENGTH: 1177
<212> TYPE: DNA
<213> ORGANISM: Artificial Sequence
<220> FEATURE:
<223> OTHER INFORMATION: Description of Artificial Sequence: Clone

<400> SEQUENCE: 23
gcacgacggg caagcccaag gggggcgatg aacagccatc gaggaatttg caatcgctta     60
ctgtggatgc aagatgctta caaactaact gaaactgatc gcgttctgca aaaaacgcct    120
tttagtttcg acgtttccgt ttgggagttt ttctggcctc tcttgacagg ggcgcgttta    180
gtgatggctc aaccaggcgg acagcgagat gcaacttact taattaacac catcgtccaa    240
gaggaaatta caacactgca ttttgtcccc tccatgttgc ggatatttct ccaaactaaa    300
gggctagaac gttgtcaatc tctaaaacgg gtgttttgta gtggagaagc cttaccagtt    360
gacctccagg agcggttttt tgactcgatg ggatgtgaac tacacaacct ctatggtcct    420
accgaagcgg caattgatgt cacattttgg cagtgtcaaa gagagagtaa cttaaaaagt    480
gtaccgattg ggagagcgat cgccaacact caamtttata tcctcgactc ccatttacaa    540
gcagttccct gggtgcgat cggcgaactt tatattggtg gtatcggcgt tgctagaggs    600
tatcttaacc gtccagactt aacagccgag cgatttattt cccatccctt taaggaaggc    660
grraaacttt acaaaacagg agacttagcc cgatatctgg ccgatggcaa tatcgaatac    720
atcggtagaa ttgatcatca agtaaaaatt cggggtttcc gcatcgaact ggagaaaatc    780
gaaactttac tagcacaaca cccgaccata cagcaaactg tcgtcacagc tagaattgat    840
```

```
catctcgaaa accagcgatt agtcgcctac atcgttcctc attcagagca gacactaacc    900
acagacgaac tgcgccactt cctcaaaaag aaactgccag aatatatggt gcctagtact    960
ttcgttttcc tagacactct accctaacc cccaacggca aaattgaccg tcgcgcttta    1020
ccagcacccg actcaacaag gcttgattca gaaaacacat atcttgctcc ccgcgattaa    1080
ttagaatttc agttgactaa aatttggtca gaaattttag gtatccagcc tatcggtgtc    1140
agggacaact tcttcttcct tgggcggccc ctcccctt                           1177
```

<210> SEQ ID NO 24
<211> LENGTH: 392
<212> TYPE: PRT
<213> ORGANISM: Artificial Sequence
<220> FEATURE:
<223> OTHER INFORMATION: Description of Artificial Sequence: Clone
<221> NAME/KEY: SITE
<222> LOCATION: (172)
<223> OTHER INFORMATION: Xaa=unknown amino acid
<221> NAME/KEY: SITE
<222> LOCATION: (360)
<223> OTHER INFORMATION: Xaa=unknown amino acid

<400> SEQUENCE: 24

```
Ala Arg Arg Ala Ser Pro Arg Gly Ala Met Asn Ser His Arg Gly Ile
  1               5                  10                  15

Cys Asn Arg Leu Leu Trp Met Gln Asp Ala Tyr Lys Leu Thr Glu Thr
             20                  25                  30

Asp Arg Val Leu Gln Lys Thr Pro Phe Ser Phe Asp Val Ser Val Trp
         35                  40                  45

Glu Phe Phe Trp Pro Leu Leu Thr Gly Ala Arg Leu Val Met Ala Gln
 50                  55                  60

Pro Gly Gly Gln Arg Asp Ala Thr Tyr Leu Ile Asn Thr Ile Val Gln
 65                  70                  75                  80

Glu Glu Ile Thr Thr Leu His Phe Val Pro Ser Met Leu Arg Ile Phe
                 85                  90                  95

Leu Gln Thr Lys Gly Leu Glu Arg Cys Gln Ser Leu Lys Arg Val Phe
            100                 105                 110

Cys Ser Gly Glu Ala Leu Pro Val Asp Leu Gln Glu Arg Phe Phe Asp
        115                 120                 125

Ser Met Gly Cys Glu Leu His Asn Leu Tyr Gly Pro Thr Glu Ala Ala
    130                 135                 140

Ile Asp Val Thr Phe Trp Gln Cys Gln Arg Glu Ser Asn Leu Lys Ser
145                 150                 155                 160

Val Pro Ile Gly Arg Ala Ile Ala Asn Thr Gln Xaa Tyr Ile Leu Asp
                165                 170                 175

Ser His Leu Gln Ala Val Pro Leu Gly Ala Ile Gly Glu Leu Tyr Ile
            180                 185                 190

Gly Gly Ile Gly Val Ala Arg Gly Tyr Leu Asn Arg Pro Asp Leu Thr
        195                 200                 205

Ala Glu Arg Phe Ile Ser His Pro Phe Lys Glu Gly Lys Leu Tyr
    210                 215                 220

Lys Thr Gly Asp Leu Ala Arg Tyr Leu Ala Asp Gly Asn Ile Glu Tyr
225                 230                 235                 240

Ile Gly Arg Ile Asp His Gln Val Lys Ile Arg Gly Phe Arg Ile Glu
                245                 250                 255

Leu Gly Glu Ile Glu Thr Leu Leu Ala Gln His Pro Thr Ile Gln Gln
            260                 265                 270
```

```
Thr Val Val Thr Ala Arg Ile Asp His Leu Glu Asn Gln Arg Leu Val
            275                 280                 285

Ala Tyr Ile Val Pro His Ser Glu Gln Thr Leu Thr Thr Asp Glu Leu
        290                 295                 300

Arg His Phe Leu Lys Lys Leu Pro Glu Tyr Met Val Pro Ser Thr
305                 310                 315                 320

Phe Val Phe Leu Asp Thr Leu Pro Leu Thr Pro Asn Gly Lys Ile Asp
                325                 330                 335

Arg Arg Ala Leu Pro Ala Pro Asp Ser Thr Arg Leu Asp Ser Glu Asn
            340                 345                 350

Thr Tyr Leu Ala Pro Arg Asp Xaa Leu Glu Phe Gln Leu Thr Lys Ile
            355                 360                 365

Trp Ser Glu Ile Leu Gly Ile Gln Pro Ile Gly Val Arg Asp Asn Phe
        370                 375                 380

Phe Phe Leu Gly Arg Pro Leu Pro
385                 390

<210> SEQ ID NO 25
<211> LENGTH: 406
<212> TYPE: PRT
<213> ORGANISM: Artificial Sequence
<220> FEATURE:
<223> OTHER INFORMATION: Description of Artificial Sequence: KS beta
      gene

<400> SEQUENCE: 25

Met Ser Ile Arg Thr Val Val Thr Gly Leu Gly Ile Ala Ala Pro Asn
1               5                   10                  15

Gly Leu Gly Ile Glu Glu Tyr Trp Ser Ala Thr Leu Ala Gly Arg Gly
            20                  25                  30

Ala Ile Gly Pro Leu Thr Arg Phe Asp Ala Ser Ser Tyr Pro Ser Arg
        35                  40                  45

Leu Ala Gly Glu Ile Arg Gly Phe Thr Ala Ala Glu His Leu Pro Gly
    50                  55                  60

Arg Leu Leu Pro Gln Thr Asp Arg Met Thr Gln Leu Ala Leu Val Ser
65                  70                  75                  80

Ala Gly Trp Ala Leu Asp Asp Ala Gly Val Val Pro Asp Glu Leu Pro
                85                  90                  95

Ala Tyr Asp Met Gly Val Ile Thr Ala Ser His Ala Gly Gly Phe Glu
            100                 105                 110

Phe Gly Gln Asn Glu Leu Lys Ala Leu Trp Ser Lys Gly Gly Lys Tyr
        115                 120                 125

Val Ser Ala Tyr Gln Ser Phe Ala Trp Phe Tyr Ala Val Asn Ser Gly
    130                 135                 140

Gln Ile Ser Ile Arg Asn Gly Met Arg Gly Pro Ser Gly Val Val Val
145                 150                 155                 160

Ser Asp Gln Ala Gly Gly Leu Asp Ala Leu Gln Ala Arg Gln
                165                 170                 175

Ile Arg Lys Gly Thr Pro Leu Ile Val Ser Gly Ala Val Asp Ala Ser
            180                 185                 190

Leu Cys Thr Trp Gly Trp Val Ala Gln Leu Ala Gly Gly Arg Leu Ser
        195                 200                 205

Arg Ser Asp Asp Pro Gly His Ala Tyr Val Pro Phe Asp Asp Ala Ala
    210                 215                 220
```

```
Val Gly His Val Pro Gly Glu Gly Ala Leu Leu Ile Leu Glu Glu
225                 230                 235                 240

Ala Glu His Ala Arg Ser Arg Gly Ala Arg Arg Ile Tyr Gly Glu Ile
            245                 250                 255

Thr Gly His Ala Ser Thr Phe Asp Pro Pro Trp Ser Gly Arg Gly
            260                 265                 270

Pro Ala Val Gln Arg Val Ile Glu Ala Leu Ala Asp Ala Gly Thr
            275                 280                 285

Val Pro Asp Glu Val Asp Val Phe Ala Asp Ala Ala Leu Pro
290                 295                 300

Glu Leu Asp Arg Ile Glu Ala Ala Ile Thr Lys Val Phe Gly Pro
305             310                 315                 320

His Ala Val Pro Val Thr Ala Pro Lys Thr Met Thr Gly Arg Leu Tyr
            325                 330                 335

Ser Gly Ala Ala Pro Leu Asp Val Ala Ala Ala Cys Leu Ala Ile Arg
            340                 345                 350

Asp Gly Leu Ile Pro Pro Thr Ile His Ser Ser Leu Ser Gly Arg Tyr
            355                 360                 365

Glu Ile Asp Leu Val Thr Gly Ala Pro Arg Thr Ala Pro Val Arg Thr
370                 375                 380

Ala Leu Val Val Ala Arg Gly His Gly Gly Phe Asn Ser Ala Val Val
385                 390                 395                 400

Val Arg Ala Pro Arg Asp
                405

<210> SEQ ID NO 26
<211> LENGTH: 415
<212> TYPE: PRT
<213> ORGANISM: Artificial Sequence
<220> FEATURE:
<223> OTHER INFORMATION: Description of Artificial Sequence: KS beta
      gene

<400> SEQUENCE: 26

Met Thr Ser Glu Leu Leu Glu Arg Thr Ala Val Arg Ser Ala Thr Ala
 1               5                  10                  15

Val Phe Thr Gly Ile Gly Val Thr Ala Pro Asn Gly Leu Gly Thr Ala
            20                  25                  30

Ala Trp Trp Gln Ala Thr Val Ala Gly Glu Ser Gly Ile Arg Pro Val
        35                  40                  45

Ser Arg Phe Asp Ala Ser Gly Tyr Pro Ser Thr Leu Ala Gly Glu Val
    50                  55                  60

Pro Gly Phe Asp Ala Glu Glu His Ile Pro Ser Arg Leu Leu Ser Gln
65                  70                  75                  80

Thr Asp His Met Thr Arg Leu Ala Leu Thr Ala Ala Lys Glu Ala Leu
                85                  90                  95

Glu Asp Ser Gly Ala Asp Pro Ala Glu Met Pro Gln Tyr Ser Ala Gly
            100                 105                 110

Ala Val Thr Ala Ala Ser Ala Gly Gly Phe Glu Phe Gly Gln Arg Glu
        115                 120                 125

Leu Gln Ala Leu Trp Ser Lys Gly Gly Gln Tyr Val Ser Ala Tyr Gln
    130                 135                 140

Ser Tyr Ala Trp Phe Tyr Ala Val Asn Thr Gly Gln Ile Ser Ile Arg
145                 150                 155                 160

His Gly Leu Arg Gly Pro Ser Gly Val Leu Val Thr Glu Gln Ala Gly
                165                 170                 175
```

```
Gly Leu Glu Ala Val Ala Gln Ala Arg Arg Gln Leu Arg Lys Gly Ser
            180                 185                 190

Lys Leu Ile Val Thr Gly Val Asp Gly Ala Val Cys Pro Trp Gly
        195                 200                 205

Trp Thr Ala Gln Leu Ala Gly Gly Arg Met Ser Pro Val Ala Asp Pro
    210                 215                 220

Ala Arg Ala Phe Leu Pro Phe Asp Ser Glu Ala Ser Gly Tyr Val Ala
225                 230                 235                 240

Gly Glu Gly Gly Ala Ile Leu Val Leu Glu Asp Ala Glu Ala Ala Arg
                245                 250                 255

Glu Arg Gly Ala Arg Ile Tyr Gly Arg Leu Ser Gly Tyr Ala Ala Thr
            260                 265                 270

Phe Asp Pro Ala Pro Gly Arg Gly Glu Pro Gly Leu Arg Arg Ala
    275                 280                 285

Ala Glu Leu Ala Leu Thr Glu Ala Gly Leu Ser Ala Ser Asp Val Asp
    290                 295                 300

Val Val Phe Ala Asp Ala Ser Gly Val Pro Glu Leu Asp Arg Gln Glu
305                 310                 315                 320

Glu Ala Ala Leu Thr Ala Leu Phe Gly Pro Arg Gly Val Pro Val Thr
                325                 330                 335

Ala Pro Lys Thr Met Thr Gly Arg Leu Ser Ala Gly Gly Ala Ser Leu
            340                 345                 350

Asp Leu Ala Ala Ala Leu Leu Ser Ile Arg Asp Ala Val Ile Pro Pro
            355                 360                 365

Thr Val Asn Val Thr Ser Pro Val Ala Ala Asp Ala Leu Asp Leu Val
    370                 375                 380

Thr Glu Ala Arg Arg Gly Pro Val Arg Thr Ala Leu Val Leu Ala Arg
385                 390                 395                 400

Gly Thr Gly Gly Phe Asn Ala Ala Val Val Thr Ala Ala Asn
                405                 410                 415

<210> SEQ ID NO 27
<211> LENGTH: 403
<212> TYPE: PRT
<213> ORGANISM: Artificial Sequence
<220> FEATURE:
<223> OTHER INFORMATION: Description of Artificial Sequence: KS beta
      gene

<400> SEQUENCE: 27

Met Ile Pro Val Ala Val Thr Gly Met Gly Val Ala Ala Pro Asn Gly
  1               5                  10                  15

Leu Gly Ala Ala Asp Tyr Trp Ala Ala Thr Arg Gly Gly Lys Ser Gly
            20                  25                  30

Ile Gly Arg Ile Thr Arg Phe Asp Pro Ser Ser Tyr Pro Ala Arg Leu
        35                  40                  45

Ala Gly Glu Ile Pro Gly Phe Glu Ala Ala Glu His Leu Pro Gly Arg
    50                  55                  60

Leu Leu Pro Gln Thr Asp Arg Val Thr Arg Leu Ser Leu Ala Ala Ala
65                  70                  75                  80

Asp Trp Ala Leu Ala Asp Ala Gly Val Glu Pro Glu Ser Phe Asp Pro
                85                  90                  95

Leu Asp Met Gly Val Val Thr Ala Gly His Ala Gly Gly Phe Glu Phe
            100                 105                 110
```

```
Gly Gln Gly Glu Leu Gln Lys Leu Trp Ala Lys Gly Ser Gln Phe Val
        115                 120                 125

Ser Ala Tyr Gln Ser Phe Ala Trp Phe Tyr Ala Val Asn Ser Gly Gln
130                 135                 140

Ile Ser Ile Arg His Gly Met Lys Gly Pro Asn Gly Val Val Val Ser
145                 150                 155                 160

Asp Gln Ala Gly Gly Leu Asp Ala Leu Ala Gln Ala Arg Arg Leu Val
                165                 170                 175

Arg Lys Gly Thr Pro Leu Ile Val Cys Gly Ala Val Asp Ala Ser Ile
            180                 185                 190

Cys Pro Trp Gly Trp Val Ala Gln Leu Ala Gly Gly Arg Met Ser Asp
        195                 200                 205

Ser Asp Glu Pro Ala Arg Ala Tyr Leu Pro Phe Asp Arg Asp Ala Arg
210                 215                 220

Gly Tyr Leu Pro Gly Glu Gly Ala Ile Leu Ile Met Glu Pro Ala
225                 230                 235                 240

Ala Ala Ala Arg Ala Arg Gly Ala Lys Val Tyr Gly Glu Ile Ser Gly
                245                 250                 255

Tyr Gly Ala Thr Phe Asp Pro Pro Gly Ser Gly Ser Gly Ser Thr
            260                 265                 270

Leu Arg Thr Ala Ile Arg Val Ala Leu Asp Asp Ala Gly Val Ala Pro
        275                 280                 285

Gly Asp Val Asp Ala Val Phe Ala Asp Gly Ala Gly Val Pro Glu Leu
290                 295                 300

Asp Arg Ala Glu Ala Glu Ala Ile Thr Asp Val Phe Gly Ser Gly Gly
305                 310                 315                 320

Val Pro Val Thr Val Pro Lys Thr Met Thr Gly Arg Leu Tyr Ser Gly
                325                 330                 335

Ala Ala Pro Leu Asp Val Ala Cys Ala Leu Leu Ala Met Gln Ala Gly
            340                 345                 350

Val Ile Pro Pro Thr Val His Ile Asp Pro Cys Pro Glu Tyr Gly Leu
        355                 360                 365

Asp Leu Val Leu His Gln Ala Arg Pro Ala Thr Val Arg Thr Ala Leu
370                 375                 380

Val Leu Ala Arg Gly His Gly Phe Asn Ser Ala Met Ala Val Arg
385                 390                 395                 400

Ala Gly Arg

<210> SEQ ID NO 28
<211> LENGTH: 407
<212> TYPE: PRT
<213> ORGANISM: Artificial Sequence
<220> FEATURE:
<223> OTHER INFORMATION: Description of Artificial Sequence: KS beta
      gene

<400> SEQUENCE: 28

Met Ser Ala Arg Phe Leu Val Thr Gly Ile Gly Val Ala Ala Pro Ser
1               5                   10                  15

Gly Leu Gly Val Glu Asp Phe Trp Ser Val Thr Arg Ile Gly Lys Asn
                20                  25                  30

Ala Ile Gly Pro Val Thr Arg Phe Asp Ala Ser Ala Tyr Pro Ser Arg
            35                  40                  45

Leu Ala Gly Glu Ile His Gly Phe Glu Pro Lys Glu His Leu Pro Gly
        50                  55                  60
```

```
Arg Leu Val Pro Gln Thr Asp Arg Val Thr Gln Leu Ala Leu Val Ala
 65                  70                  75                  80

Ala Asp Cys Ala Phe Ala Asp Ala Gly Ile Glu Pro Gly Thr Ile Asp
                 85                  90                  95

Pro Tyr Ala Met Gly Val Val Thr Ala Ala Gly Ala Gly Gly Phe Glu
            100                 105                 110

Phe Ala Glu Asn Glu Leu Arg Lys Leu Trp Ser Glu Gly Ala Lys Arg
        115                 120                 125

Val Ser Ala Tyr Gln Ser Phe Ala Trp Phe Tyr Ala Val Asn Ser Gly
130                 135                 140

Gln Ile Ser Ile Arg Asn Gly Leu Arg Gly Pro Ala Gly Val Val Ile
145                 150                 155                 160

Ser Asp Gln Ala Gly Leu Asp Ala Leu Ala Gln Ala Arg Arg Gln
                165                 170                 175

Leu Arg Lys Gly Ser Lys Leu Ile Ala Thr Gly Gly Phe Asp Ala Pro
            180                 185                 190

Ile Cys Ser Leu Gly Trp Ala Ser Gln Pro Arg Thr Gly Gly Leu Met
        195                 200                 205

Phe His Glu Arg Thr Glu Pro Glu Arg Ala Tyr Leu Pro Phe Glu Asp
    210                 215                 220

Ala Ala Ala Gly Tyr Val Pro Gly Glu Gly Gly Ala Met Leu Ile Leu
225                 230                 235                 240

Glu Asp Glu Asp Ser Ala Arg Asp Arg Gly Ala Arg Thr Val Tyr Gly
                245                 250                 255

Glu Phe Ala Gly Tyr Gly Ala Thr Leu Asp Pro Lys Pro Gly Ser Gly
            260                 265                 270

Arg Glu Pro Gly Leu Arg Arg Ala Ile Asp Val Ala Leu Thr Asp Ala
        275                 280                 285

Ala Cys His Pro Ala Glu Val Glu Val Phe Ala Asp Gly Ala Ala
290                 295                 300

Thr Pro Arg Leu Asp Arg Glu Glu Ala Glu Ala Ile Thr Ala Val Phe
305                 310                 315                 320

Gly Pro Arg Ala Val Pro Val Thr Val Pro Lys Thr Met Thr Gly Arg
                325                 330                 335

Ile Asn Ser Gly Gly Ala Pro Ile Asp Val Val Ser Ala Val Leu Ser
            340                 345                 350

Met Arg Glu Gly Leu Ile Pro Pro Thr Thr Asn Val Glu Leu Ser Asp
        355                 360                 365

Ala Tyr Asp Leu Asp Leu Val Ala Val Arg Pro Arg Thr Ala Ser Val
    370                 375                 380

Arg Thr Ala Leu Val Leu Ala Arg Gly Arg Gly Gly Phe Asn Ser Ala
385                 390                 395                 400

Val Val Val Arg Ala Val Asp
                405
```

<210> SEQ ID NO 29
<211> LENGTH: 643
<212> TYPE: DNA
<213> ORGANISM: Artificial Sequence
<220> FEATURE:
<223> OTHER INFORMATION: Description of Artificial Sequence: Clone
      Xa.cum.6H

<400> SEQUENCE: 29

-continued

```
ggatctgctt gaggtagtct acgaggcact ggagtcagca gggtactttg gcgccaagtc      60
aaacccggaa cctgatgact atggatgcta tatcggtgca gtgatgaaca actactatga     120
caacgtttct tgccatccac ccaccgcata cgctactctt ggaacgtcgc gttgcttcct     180
tagtggctgc atgagccatt actttggatg gacgggacct tccttgacca ttgatacggc     240
ttgctcgtca tcactagttg ctataaacac cgcttgtaga gcaatatggt ctggtgagtg     300
ctcccgggcc atagctgggg gtaccaatgt cttcacaagt ccgtttgact accagaatct     360
tcgcgccgca ggattcctca gccctagcgg gcaatgcaag ccgtttgatg cttctgctga     420
tggctactgc cgtggagaag gagttggtgt cgttgtgctt aagcctttga cggctgctat     480
gcaagagaac gataacatcc ttggcgtcat tgtgggtct gcagcaaacc aaaaccaaaa     540
cctcagtcat atcacggtgc cccattcggg ctcacaagtc cagctttatc gaaaggtgat     600
gaagcttgca ggtatagagc cagagtcagt ctcctacgtt gag                       643
```

<210> SEQ ID NO 30
<211> LENGTH: 214
<212> TYPE: PRT
<213> ORGANISM: Artificial Sequence
<220> FEATURE:
<223> OTHER INFORMATION: Description of Artificial Sequence: Clone
      Xa.cum.6H

<400> SEQUENCE: 30

```
Asp Leu Leu Glu Val Val Tyr Glu Ala Leu Glu Ser Ala Gly Tyr Phe
  1               5                  10                  15

Gly Ala Lys Ser Asn Pro Glu Pro Asp Asp Tyr Gly Cys Tyr Ile Gly
             20                  25                  30

Ala Val Met Asn Asn Tyr Tyr Asp Asn Val Ser Cys His Pro Pro Thr
         35                  40                  45

Ala Tyr Ala Thr Leu Gly Thr Ser Arg Cys Phe Leu Ser Gly Cys Met
     50                  55                  60

Ser His Tyr Phe Gly Trp Thr Gly Pro Ser Leu Thr Ile Asp Thr Ala
 65                  70                  75                  80

Cys Ser Ser Ser Leu Val Ala Ile Asn Thr Ala Cys Arg Ala Ile Trp
                 85                  90                  95

Ser Gly Glu Cys Ser Arg Ala Ile Ala Gly Gly Thr Asn Val Phe Thr
            100                 105                 110

Ser Pro Phe Asp Tyr Gln Asn Leu Arg Ala Ala Gly Phe Leu Ser Pro
        115                 120                 125

Ser Gly Gln Cys Lys Pro Phe Asp Ala Ser Ala Asp Gly Tyr Cys Arg
    130                 135                 140

Gly Glu Gly Val Gly Val Val Leu Lys Pro Leu Thr Ala Ala Met
145                 150                 155                 160

Gln Glu Asn Asp Asn Ile Leu Gly Val Ile Val Gly Ser Ala Ala Asn
                165                 170                 175

Gln Asn Gln Asn Leu Ser His Ile Thr Val Pro His Ser Gly Ser Gln
            180                 185                 190

Val Gln Leu Tyr Arg Lys Val Met Lys Leu Ala Gly Ile Glu Pro Glu
        195                 200                 205

Ser Val Ser Tyr Val Glu
    210
```

<210> SEQ ID NO 31
<211> LENGTH: 643

<212> TYPE: DNA
<213> ORGANISM: Leptogium corniculatum

<400> SEQUENCE: 31

```
aatcctcatg gaatcagctt ggcaaacact agaaaacgct ggcataactg cgaacaaagt    60
agctggcagc agtacaggag tttttgtggg tgctagtggc tctgattact gttgggtaat   120
ggagcgggta ggtattccca tagaagctca cgttgcaacg ggcacgtcgt tggcagcgct   180
ggcaaatcgc atctcttact tttttgactt gcgaggccca agcatcgtca ttgatacggc   240
gtgttctagt tcgttgatgg cagtgcatca ggcggttcaa tctatccgag caggtgagtg   300
cttacaagca ctggtgggcg gtatacatat catgagccat ccggctaaca gtattgcata   360
ttacaaggct gggatgttgg cgcatgatgg caagtgcaag acatttgacg atcgcgcaga   420
tgggtacgtt cgcagtgaag gcgctgtgat gcttctgctc aagcaattgc atcaggcgga   480
agcagatggc gatctaattt atgcgacaat caagggtca gcctcgaatc atggtggaca   540
gtccgccggc ctcaccgtac cgaatccgca acagcaggca gcactcttaa ccaatgcctg   600
gaaagcctct ggtgtagacc ctaacacgat tagttttatc gaa                     643
```

<210> SEQ ID NO 32
<211> LENGTH: 214
<212> TYPE: PRT
<213> ORGANISM: Leptogium corniculatum

<400> SEQUENCE: 32

```
Ile Leu Met Glu Ser Ala Trp Gln Thr Leu Glu Asn Ala Gly Ile Thr
  1               5                  10                  15

Ala Asn Lys Val Ala Gly Ser Ser Thr Gly Val Phe Val Gly Ala Ser
             20                  25                  30

Gly Ser Asp Tyr Cys Trp Val Met Glu Arg Val Gly Ile Pro Ile Glu
         35                  40                  45

Ala His Val Ala Thr Gly Thr Ser Leu Ala Ala Leu Ala Asn Arg Ile
     50                  55                  60

Ser Tyr Phe Phe Asp Leu Arg Gly Pro Ser Ile Val Ile Asp Thr Ala
 65                  70                  75                  80

Cys Ser Ser Ser Leu Met Ala Val His Gln Ala Val Gln Ser Ile Arg
                 85                  90                  95

Ala Gly Glu Cys Leu Gln Ala Leu Val Gly Gly Ile His Ile Met Ser
            100                 105                 110

His Pro Ala Asn Ser Ile Ala Tyr Tyr Lys Ala Gly Met Leu Ala His
        115                 120                 125

Asp Gly Lys Cys Lys Thr Phe Asp Asp Arg Ala Asp Gly Tyr Val Arg
    130                 135                 140

Ser Glu Gly Ala Val Met Leu Leu Leu Lys Gln Leu His Gln Ala Glu
145                 150                 155                 160

Ala Asp Gly Asp Leu Ile Tyr Ala Thr Ile Lys Gly Ser Ala Ser Asn
                165                 170                 175

His Gly Gly Gln Ser Ala Gly Leu Thr Val Pro Asn Pro Gln Gln Gln
            180                 185                 190

Ala Ala Leu Leu Thr Asn Ala Trp Lys Ala Ser Gly Val Asp Pro Asn
        195                 200                 205

Thr Ile Ser Phe Ile Glu
    210
```

<210> SEQ ID NO 33
<211> LENGTH: 637
<212> TYPE: DNA
<213> ORGANISM: Leptogium corniculatum

<400> SEQUENCE: 33

```
tatattactc caggttgctt acgaagcatt ggaaatgtcc gggtatttcg ccgactcgtc      60
caagcctgag gacgtaggtt gctatattgg agcttgtgca acagattacg atttcagcgt     120
agcgtcccat cctcctacgg catactcagc aactggcacg ctccgatctt tcctgagtgg     180
caagctgtca cattactttg gttggtctgg tccctctctt gtcctggaca ccgcctgctc     240
ttcatcggcg gtggccattc acactgcatg tactgctttg aggactggcc agtgttctca     300
ggctttagca ggcgggatta ctttgatgac cagcccgtat ctctttgaga actttgctgc     360
cgcccatttc ttgagcccaa cgggaggctc aaagccgttc agtgcagatg cagatgggta     420
ttgtagagga aagggggtg ggctcgtggt cttgaaacga ctttcagatg ctatcaggga     480
taacgaccac atcattagcg tcatcgctgg ctcagccgtc aaccagaacg ctaactgtgt     540
gcctatcacc gtccctcata cttcgtctca ggcaatctc tatgaacgag ttaccgcaca     600
ggcaggggtg acacctaata aggtcacttt tgtggaa                              637
```

<210> SEQ ID NO 34
<211> LENGTH: 212
<212> TYPE: PRT
<213> ORGANISM: Leptogium corniculatum

<400> SEQUENCE: 34

```
Ile Leu Leu Gln Val Ala Tyr Glu Ala Leu Glu Met Ser Gly Tyr Phe
 1               5                  10                  15

Ala Asp Ser Ser Lys Pro Glu Asp Val Gly Cys Tyr Ile Gly Ala Cys
            20                  25                  30

Ala Thr Asp Tyr Asp Phe Ser Val Ala Ser His Pro Pro Thr Ala Tyr
        35                  40                  45

Ser Ala Thr Gly Thr Leu Arg Ser Phe Leu Ser Gly Lys Leu Ser His
    50                  55                  60

Tyr Phe Gly Trp Ser Gly Pro Ser Leu Val Leu Asp Thr Ala Cys Ser
65                  70                  75                  80

Ser Ser Ala Val Ala Ile His Thr Ala Cys Thr Ala Leu Arg Thr Gly
                85                  90                  95

Gln Cys Ser Gln Ala Leu Ala Gly Gly Ile Thr Leu Met Thr Ser Pro
            100                 105                 110

Tyr Leu Phe Glu Asn Phe Ala Ala His Phe Leu Ser Pro Thr Gly
        115                 120                 125

Gly Ser Lys Pro Phe Ser Ala Asp Ala Asp Gly Tyr Cys Arg Gly Glu
    130                 135                 140

Gly Gly Gly Leu Val Val Leu Lys Arg Leu Ser Asp Ala Ile Arg Asp
145                 150                 155                 160

Asn Asp His Ile Ile Ser Val Ile Ala Gly Ser Ala Val Asn Gln Asn
                165                 170                 175

Ala Asn Cys Val Pro Ile Thr Val Pro His Thr Ser Ser Gln Gly Asn
            180                 185                 190

Leu Tyr Glu Arg Val Thr Ala Gln Ala Gly Val Thr Pro Asn Lys Val
        195                 200                 205
```

Thr Phe Val Glu
    210

<210> SEQ ID NO 35
<211> LENGTH: 691
<212> TYPE: DNA
<213> ORGANISM: Leptogium corniculatum

<400> SEQUENCE: 35

```
ccatctgcta gaaatcagct acgaggcgct cgagaatgca ggctttccac tgcctagcat    60
tgctggcacg aacatgggtg tctttgtcgg cggaagcaac tctgagtatc gagcgcacat   120
cggaaacgat accgacaact taccgatgtt tgaagcaaca ggcaatgcag aatctctgct   180
ggcgaatcga gtctcttatg tgtatgatct ccacggcgca gtctgacga ttggtaccgc    240
ttgttccgtc gagtttagca gctttggata gcgcgtttct cagcttgcag ctggtaagtc    300
gtccacagca attgttgccg gctccgttgt tcgaatcgta ccgtcatcga ccatctcacc   360
ttctactatg aagtaagcag tcatggctct tgacacggag actactcacc attccaggct   420
tctgtcacca gaagggcggt gttatgcgtt cgatgacaga gccactagtg gttttggaag   480
gggtgaaggt tctgcctgca taatattgga aaccttagag gcagccttaa gagacaacga   540
cccaatccga tcggtcattc gcaattcggg agtcaatcaa gatggtaaaa ctgcaggtat   600
cacaatgcca aatggggaag cgcaagcttc attgatacaa tctgtttatc gcactgctgg   660
attggaccct ctgcagacag attacgtcga g                                    691
```

<210> SEQ ID NO 36
<211> LENGTH: 215
<212> TYPE: PRT
<213> ORGANISM: Leptogium corniculatum
<220> FEATURE:
<221> NAME/KEY: SITE
<222> LOCATION: (90)
<223> OTHER INFORMATION: Xaa=unknown amino acid

<400> SEQUENCE: 36

```
His Leu Leu Glu Ile Ser Tyr Glu Ala Leu Glu Asn Ala Gly Phe Pro
  1               5                  10                  15

Leu Pro Ser Ile Ala Gly Thr Asn Met Gly Val Phe Val Gly Gly Ser
                 20                  25                  30

Asn Ser Glu Tyr Arg Ala His Ile Gly Asn Asp Thr Asp Asn Leu Pro
             35                  40                  45

Met Phe Glu Ala Thr Gly Asn Ala Glu Ser Leu Leu Ala Asn Arg Val
         50                  55                  60

Ser Tyr Val Tyr Asp Leu His Gly Ala Ser Leu Thr Ile Gly Thr Ala
 65                  70                  75                  80

Cys Ser Val Glu Phe Ser Ser Phe Gly Xaa Arg Val Ser Gln Leu Ala
                 85                  90                  95

Ala Gly Lys Ser Ser Thr Ala Ile Val Ala Gly Ser Val Val Arg Ile
                100                 105                 110

Val Pro Ser Ser Thr Ile Ser Pro Ser Thr Met Lys Leu Leu Ser Pro
            115                 120                 125

Glu Gly Arg Cys Tyr Ala Phe Asp Asp Arg Ala Thr Ser Gly Phe Gly
        130                 135                 140

Arg Gly Glu Gly Ser Ala Cys Ile Ile Leu Glu Thr Leu Glu Ala Ala
145                 150                 155                 160

Leu Arg Asp Asn Asp Pro Ile Arg Ser Val Ile Arg Asn Ser Gly Val
                165                 170                 175
```

Asn Gln Asp Gly Lys Thr Ala Gly Ile Thr Met Pro Asn Gly Glu Ala
                180                 185                 190

Gln Ala Ser Leu Ile Gln Ser Val Tyr Arg Thr Ala Gly Leu Asp Pro
        195                 200                 205

Leu Gln Thr Asp Tyr Val Glu
    210                 215

<210> SEQ ID NO 37
<211> LENGTH: 680
<212> TYPE: DNA
<213> ORGANISM: Leptogium corniculatum

<400> SEQUENCE: 37
aactgttaga ggtcagttac gaggcgtttg agaatgcggg catatcatta tcgagtgttg    60
caggtaccga cgttggggta ttcatcagtg ccagcaccaa tgattaccgt ttcgttttcc   120
acaacgacct cgacacattg ccaatgtttg aatccactgg gagtgaatta tcgatcatgt   180
ccaatcgtat ctcctatact ttcaatctta gaggtccaag tatgacgatt gatactccct   240
gttcctcaag tttgatcgca ctccatacag cattcagaag tctacaggtc ggagaaagct   300
cttgcgccat tgtcggtgga tctaacctcc acatcactcc agattcctac atttcattct   360
cgacgatgag gtaagcacta tcgtttgcga attacctatc tttgattacg agtgactaag   420
ttgtacaggc tcctgtcgcc ccatggacga tcgtgcagtc aatgggtttg ggcgcggaga   480
gggcacaagt tgcataatac tgaagccttt agatgccgca ttgaaagacc acgatcccat   540
aagggcagtt attcgcaata cgggcactaa tcaagatggg aagacgacag gtatcacgat   600
gccgaatggt gaagcacagg ccgccttaat gcaatcagtc tacgaggcag cgggcttaga   660
tccccttgaa acagactatg                                               680

<210> SEQ ID NO 38
<211> LENGTH: 209
<212> TYPE: PRT
<213> ORGANISM: Leptogium corniculatum

<400> SEQUENCE: 38

Leu Leu Glu Val Ser Tyr Glu Ala Phe Glu Asn Ala Gly Ile Ser Leu
  1               5                  10                  15

Ser Ser Val Ala Gly Thr Asp Val Gly Val Phe Ile Ser Ala Ser Thr
                 20                  25                  30

Asn Asp Tyr Arg Phe Val Phe His Asn Asp Leu Asp Thr Leu Pro Met
             35                  40                  45

Phe Glu Ser Thr Gly Ser Glu Leu Ser Ile Met Ser Asn Arg Ile Ser
         50                  55                  60

Tyr Thr Phe Asn Leu Arg Gly Pro Ser Met Thr Ile Asp Thr Pro Cys
 65                  70                  75                  80

Ser Ser Ser Leu Ile Ala Leu His Thr Ala Phe Arg Ser Leu Gln Val
                 85                  90                  95

Gly Glu Ser Ser Cys Ala Ile Val Gly Gly Ser Asn Leu His Ile Thr
                100                 105                 110

Pro Asp Ser Tyr Ile Ser Phe Ser Thr Met Ser Cys Thr Gly Ser Cys
            115                 120                 125

Arg Pro Met Asp Asp Arg Ala Val Asn Gly Phe Gly Arg Gly Glu Gly
        130                 135                 140

Thr Ser Cys Ile Ile Leu Lys Pro Leu Asp Ala Ala Leu Lys Asp His
145                 150                 155                 160

```
Asp Pro Ile Arg Ala Val Ile Arg Asn Thr Gly Thr Asn Gln Asp Gly
                165                 170                 175

Lys Thr Thr Gly Ile Thr Met Pro Asn Gly Glu Ala Gln Ala Ala Leu
            180                 185                 190

Met Gln Ser Val Tyr Glu Ala Ala Gly Leu Asp Pro Leu Glu Thr Asp
        195                 200                 205

Tyr

<210> SEQ ID NO 39
<211> LENGTH: 691
<212> TYPE: DNA
<213> ORGANISM: Leptogium corniculatum

<400> SEQUENCE: 39
gcatttgctg gaggtgagct atgaagcgct tgaaaatgct ggcctttctc ttccttgcat      60
tgccggcacc aaaatgggag tcttcgttgg tggaggcaat gcakagtatc gatcgcatat    120
cggccaagat attgacaatc tgcctatgtt cgaggcaact ggtaacgcag aggcgctatt    180
ggcgaataga gtttcttatg tatatgatct tcgaggaccg agtctaacca ccgataccgc    240
ctgttcctca gtctcgccg ctttgaacac ggcattctta gtctacagg ctggcgagtc      300 gtctacagca ctggtcggta gctcagtaat tcggcttagg cctgagtcag ccatctcact    360
ttccagcatg cagtaagtcc ttcatggtgc acctgcatac attgctaata agtgcaggct    420
tctatcccca gatggaaaat cttacgcgtt cgatgagaga gctaccagtg gttttggaag    480
gggtgagggt tcgggttgca taatactaaa acccctggac gcagccgtga gagacggaga    540
cccaattaga gcagtcattt gtaactcggg tgtaaaccaa gacggcaaga ctgctggtat    600
tacaatgcct aatggacacg cgcaagcttc tctaatacgg tctgtttatc agtctacagg    660
gatagaccct ttaatgacgg actatgtcga a                                   691

<210> SEQ ID NO 40
<211> LENGTH: 215
<212> TYPE: PRT
<213> ORGANISM: Leptogium corniculatum
<220> FEATURE:
<221> NAME/KEY: SITE
<222> LOCATION: (35)
<223> OTHER INFORMATION: Xaa=unknown amino acid

<400> SEQUENCE: 40

His Leu Leu Glu Val Ser Tyr Glu Ala Leu Glu Asn Ala Gly Leu Ser
 1               5                  10                  15

Leu Pro Cys Ile Ala Gly Thr Lys Met Gly Val Phe Val Gly Gly Gly
            20                  25                  30

Asn Ala Xaa Tyr Arg Ser His Ile Gly Gln Asp Ile Asp Asn Leu Pro
        35                  40                  45

Met Phe Glu Ala Thr Gly Asn Ala Glu Ala Leu Leu Ala Asn Arg Val
    50                  55                  60

Ser Tyr Val Tyr Asp Leu Arg Gly Pro Ser Leu Thr Thr Asp Thr Ala
65                  70                  75                  80

Cys Ser Ser Ser Leu Ala Ala Leu Asn Thr Ala Phe Leu Ser Leu Gln
                85                  90                  95

Ala Gly Glu Ser Ser Thr Ala Leu Val Gly Ser Ser Val Ile Arg Leu
            100                 105                 110

Arg Pro Glu Ser Ala Ile Ser Leu Ser Ser Met Gln Leu Leu Ser Pro
        115                 120                 125
```

```
Asp Gly Lys Ser Tyr Ala Phe Asp Glu Arg Ala Thr Ser Gly Phe Gly
    130                 135                 140
Arg Gly Glu Gly Ser Gly Cys Ile Ile Leu Lys Pro Leu Asp Ala Ala
145                 150                 155                 160
Val Arg Asp Gly Asp Pro Ile Arg Ala Val Ile Cys Asn Ser Gly Val
                165                 170                 175
Asn Gln Asp Gly Lys Thr Ala Gly Ile Thr Met Pro Asn Gly His Ala
            180                 185                 190
Gln Ala Ser Leu Ile Arg Ser Val Tyr Gln Ser Thr Gly Ile Asp Pro
        195                 200                 205
Leu Met Thr Asp Tyr Val Glu
    210                 215

<210> SEQ ID NO 41
<211> LENGTH: 637
<212> TYPE: DNA
<213> ORGANISM: Leptogium corniculatum

<400> SEQUENCE: 41
gctgtttctt caaactagct ggcaatgcat tgaagatgcg ggatataacc ccacatcctt    60
tgcaggtagc aagtgtggcg tatttgtcgg ctgcgaaacg ggagactatg gaaagattgt   120
gcagcgatat gaattgagcg ctctcggatt gctaggctct tctgcggcac tgctcccggc   180
aaggatctcc tatttcctca acctccaggg cccttgtatg gcgatcgaca cagcctgctc   240
tgcatcccta gttgccatag ccaacgcctg cgacagcctg gtactgggtc actccgatgc   300
agccttggcc ggaggagtct acgtcctctc cgggccggaa atgcacatta tgatgagcaa   360
agctggtatc ttgtcacccg atggcagatg tttcaccttc gatcgacgtg ctaacggctt   420
tgtaccgggc gaaggtgtgg gcgtcgtgtt actcaaacgc cttgccgatg ccgaaaaaga   480
cggtgataat atctgtggtg tgattcgagg ctgggggtg aatcaagacg gcaagaccag   540
tggaattaca gcacctaacg gacagtcaca gcaacgattg cagaaagaag tctacgaacg   600
gtttcagatt cagccagcag acattcaact ggttgag                            637

<210> SEQ ID NO 42
<211> LENGTH: 212
<212> TYPE: PRT
<213> ORGANISM: Leptogium corniculatum

<400> SEQUENCE: 42

Leu Phe Leu Gln Thr Ser Trp Gln Cys Ile Glu Asp Ala Gly Tyr Asn
  1                   5                  10                  15
Pro Thr Ser Phe Ala Gly Ser Lys Cys Gly Val Phe Val Gly Cys Glu
                 20                  25                  30
Thr Gly Asp Tyr Gly Lys Ile Val Gln Arg Tyr Glu Leu Ser Ala Leu
             35                  40                  45
Gly Leu Leu Gly Ser Ser Ala Ala Leu Leu Pro Ala Arg Ile Ser Tyr
         50                  55                  60
Phe Leu Asn Leu Gln Gly Pro Cys Met Ala Ile Asp Thr Ala Cys Ser
 65                  70                  75                  80
Ala Ser Leu Val Ala Ile Ala Asn Ala Cys Asp Ser Leu Val Leu Gly
                 85                  90                  95
His Ser Asp Ala Ala Leu Ala Gly Gly Val Tyr Val Leu Ser Gly Pro
            100                 105                 110
```

-continued

```
Glu Met His Ile Met Met Ser Lys Ala Gly Ile Leu Ser Pro Asp Gly
        115                 120                 125

Arg Cys Phe Thr Phe Asp Arg Arg Ala Asn Gly Phe Val Pro Gly Glu
    130                 135                 140

Gly Val Gly Val Val Leu Leu Lys Arg Leu Ala Asp Ala Glu Lys Asp
145                 150                 155                 160

Gly Asp Asn Ile Cys Gly Val Ile Arg Gly Trp Gly Val Asn Gln Asp
                165                 170                 175

Gly Lys Thr Ser Gly Ile Thr Ala Pro Asn Gly Gln Ser Gln Gln Arg
            180                 185                 190

Leu Gln Lys Glu Val Tyr Glu Arg Phe Gln Ile Gln Pro Ala Asp Ile
        195                 200                 205

Gln Leu Val Glu
    210

<210> SEQ ID NO 43
<211> LENGTH: 643
<212> TYPE: DNA
<213> ORGANISM: Parmelia sulcata

<400> SEQUENCE: 43
gatgatgata gaagtcgctt accaaggact tgagagtgca gggctgtctc ttcaggatgt      60
tgccggatcg aggactggag tcttcattgg ccatttcagc agtgattacc gagacatgat     120
attcagagat cccgagaggg caccgaccta cactttcagt ggggttagta agacgtcatt     180
ggcgaatcgc atctcctggc tgttcgacct gaaaggccca agtttcagct ggacacagc     240 ctgctcgtcg agtctggtcg ccctgcattt ggcttgccaa agcttacgcg ctggagagtc     300
agatatcgcc attgtcggag gggtcaacct tctctggaat ccggagttgt tcatgtatct     360
ctccaatcag cactttctct cgccagatgg gaaatgtaaa agctttgacg aatccggcga     420
tggctatggt cgtggcgaag gcattgccgc tcttgtacta agaagagtcg acgacgcgat     480
tgcggcccgg gaccctattc gtgccatcat tcgcggtact gggagtaatc aggacggaca     540
caccaaaggc ttcacccctcc ccagcgcaga agcccaggcg aggttgatta gagatacgta     600
ctctgccgcg gggctaggtt ttagagacac gcgatacgta gaa                        643

<210> SEQ ID NO 44
<211> LENGTH: 214
<212> TYPE: PRT
<213> ORGANISM: Parmelia sulcata

<400> SEQUENCE: 44

Met Met Ile Glu Val Ala Tyr Gln Gly Leu Glu Ser Ala Gly Leu Ser
1               5                   10                  15

Leu Gln Asp Val Ala Gly Ser Arg Thr Gly Val Phe Ile Gly His Phe
            20                  25                  30

Ser Ser Asp Tyr Arg Asp Met Ile Phe Arg Asp Pro Glu Arg Ala Pro
        35                  40                  45

Thr Tyr Thr Phe Ser Gly Val Ser Lys Thr Ser Leu Ala Asn Arg Ile
    50                  55                  60

Ser Trp Leu Phe Asp Leu Lys Gly Pro Ser Phe Ser Leu Asp Thr Ala
65                  70                  75                  80

Cys Ser Ser Ser Leu Val Ala Leu His Leu Ala Cys Gln Ser Leu Arg
                85                  90                  95

Ala Gly Glu Ser Asp Ile Ala Ile Val Gly Gly Val Asn Leu Leu Trp
            100                 105                 110
```

Asn Pro Glu Leu Phe Met Tyr Leu Ser Asn Gln His Phe Leu Ser Pro
        115                 120                 125

Asp Gly Lys Cys Lys Ser Phe Asp Glu Ser Gly Asp Gly Tyr Gly Arg
    130                 135                 140

Gly Glu Gly Ile Ala Ala Leu Val Leu Arg Arg Val Asp Asp Ala Ile
145                 150                 155                 160

Ala Ala Arg Asp Pro Ile Arg Ala Ile Ile Arg Gly Thr Gly Ser Asn
                165                 170                 175

Gln Asp Gly His Thr Lys Gly Phe Thr Leu Pro Ser Ala Glu Ala Gln
            180                 185                 190

Ala Arg Leu Ile Arg Asp Thr Tyr Ser Ala Ala Gly Leu Gly Phe Arg
        195                 200                 205

Asp Thr Arg Tyr Val Glu
    210

<210> SEQ ID NO 45
<211> LENGTH: 655
<212> TYPE: DNA
<213> ORGANISM: Parmelia sulcata

<400> SEQUENCE: 45
rgtccttatg gagaccgtct acgaggcaat tgagtctgcg ggtatgactt tgaaggggct      60
gcaaggcagc gacacaagtg tgtatgccgg cgtcatgtgt ggcgactacg aggccataca     120
gctccgcgat ctggacgcgg ccccgactta tttcgcagtg gaacctcgc gagctatcct     180 ctccaatcga atctcgtatt tcttcaactg gcacggcgcg tccatcacca tggacacggc     240
atgttcctct agtctggtcg ccattcactt ggccgttcag rgcttcgggg caaatgaatc     300
acgratggcc gtggcgtgtg ggtcgaacct cattctcgga cccgagagtt acattattga     360
aagcaaggtg aagatgctgt ccccggacgg tctcagccga atgtgggata agacgccaa     420 cggctatgcg cgtggagatg gcgttgcggc cgttgttttg aagactctca gcgccgcgct     480
ggcggacgga gaccacattg aatgtctcat acgggagacg ggactcaacc aggacggtgc     540
gacagccggt ctcaccatgc ctagcgccac tgcgcagcga gctcttattc acagtacgta     600
caccaaggca ggtcttgatc tcactgccca ggcagaccgt ccccagtatt tcgag          655

<210> SEQ ID NO 46
<211> LENGTH: 218
<212> TYPE: PRT
<213> ORGANISM: Parmelia sulcata
<220> FEATURE:
<221> NAME/KEY: SITE
<222> LOCATION: (94)
<223> OTHER INFORMATION: Xaa=unknown amino acid

<400> SEQUENCE: 46

Val Leu Met Glu Thr Val Tyr Glu Ala Ile Glu Ser Ala Gly Met Thr
1                5                  10                  15

Leu Lys Gly Leu Gln Gly Ser Asp Thr Ser Val Tyr Ala Gly Val Met
            20                  25                  30

Cys Gly Asp Tyr Glu Ala Ile Gln Leu Arg Asp Leu Asp Ala Ala Pro
        35                  40                  45

Thr Tyr Phe Ala Val Gly Thr Ser Arg Ala Ile Leu Ser Asn Arg Ile
    50                  55                  60

Ser Tyr Phe Phe Asn Trp His Gly Ala Ser Ile Thr Met Asp Thr Ala
65                  70                  75                  80

```
Cys Ser Ser Ser Leu Val Ala Ile His Leu Ala Val Gln Xaa Leu Arg
                85                  90                  95

Ala Asn Glu Ser Arg Met Ala Val Ala Cys Gly Ser Asn Leu Ile Leu
            100                 105                 110

Gly Pro Glu Ser Tyr Ile Ile Glu Ser Lys Val Lys Met Leu Ser Pro
        115                 120                 125

Asp Gly Leu Ser Arg Met Trp Asp Lys Asp Ala Asn Gly Tyr Ala Arg
    130                 135                 140

Gly Asp Gly Val Ala Ala Val Val Leu Lys Thr Leu Ser Ala Ala Leu
145                 150                 155                 160

Ala Asp Gly Asp His Ile Glu Cys Leu Ile Arg Glu Thr Gly Leu Asn
                165                 170                 175

Gln Asp Gly Ala Thr Ala Gly Leu Thr Met Pro Ser Ala Thr Ala Gln
            180                 185                 190

Arg Ala Leu Ile His Ser Thr Tyr Thr Lys Ala Gly Leu Asp Leu Thr
        195                 200                 205

Ala Gln Ala Asp Arg Pro Gln Tyr Phe Glu
    210                 215
```

<210> SEQ ID NO 47
<211> LENGTH: 754
<212> TYPE: DNA
<213> ORGANISM: Parmelia sulcata
<220> FEATURE:
<221> NAME/KEY: modified_base
<222> LOCATION: (753)
<223> OTHER INFORMATION: n=a, c, g or t

<400> SEQUENCE: 47

```
aggtctgttg gagacggttt atcgcgcctt tgaaaacggt aaggccaccc tgggaataaa      60
ccggcttctc gtcctgacgg cttactctat gctagctggt atacccatgg agcaggtcct    120
cgggtcgaag acatccgttt acgtgggatg tttcacccgc gagttcgagc agttgctcgc    180
gagggacccc gagatgaatc tgaaatacat cgctacgggc accggcacgg cgatgctgtc    240
gaatcgcctc tcctggttct atgacttgaa aggcgccagt atcactcttg atactgcctg    300
ttcgtccagt ctcaatgcgt gccatcttgc ttgcgcaagc ttacgtaatg agaagccaa     360
tatggtaaga ctccaactca tcgcgggact gaacaattgc atactgatcc atcaaaggcc    420
ctggtaggag gctgcaatct tttctataac ccggaaacga tcatccctct gacaaatcta    480
ggctttcttt ctccggataa caaatgttat agttttgacc atcgtgctaa cggttactct    540
cgcggcgagg ggtttggtat tcttgtattg aagagactgt cggacgctct acgcgataac    600
gacactgtcc gtgcagtgat tcgggcctct tcgtctaacc aggatggcaa gtctcccggt    660
atcacacagc ctaccaaaca agcgcaaata caactgatca agacactta cgcggctgcc      720
gggctggact atacgcaaac ccgctacttc gana                                  754
```

<210> SEQ ID NO 48
<211> LENGTH: 214
<212> TYPE: PRT
<213> ORGANISM: Parmelia sulcata
<220> FEATURE:
<221> NAME/KEY: SITE
<222> LOCATION: (214)
<223> OTHER INFORMATION: Xaa=unknown amino acid

<400> SEQUENCE: 48

```
Gly Leu Leu Glu Thr Val Tyr Arg Ala Phe Glu Asn Ala Gly Ile Pro
  1               5                  10                  15
```

```
Met Glu Gln Val Leu Gly Ser Lys Thr Ser Val Tyr Val Gly Cys Phe
            20                  25                  30

Thr Arg Glu Phe Glu Gln Leu Leu Ala Arg Asp Pro Glu Met Asn Leu
        35                  40                  45

Lys Tyr Ile Ala Thr Gly Thr Gly Thr Ala Met Leu Ser Asn Arg Leu
    50                  55                  60

Ser Trp Phe Tyr Asp Leu Lys Gly Ala Ser Ile Thr Leu Asp Thr Ala
65                  70                  75                  80

Cys Ser Ser Ser Leu Asn Ala Cys His Leu Ala Cys Ala Ser Leu Arg
                85                  90                  95

Asn Gly Glu Ala Asn Met Ala Leu Val Gly Gly Cys Asn Leu Phe Tyr
            100                 105                 110

Asn Pro Glu Thr Ile Ile Pro Leu Thr Asn Leu Gly Phe Leu Ser Pro
        115                 120                 125

Asp Asn Lys Cys Tyr Ser Phe Asp His Arg Ala Asn Gly Tyr Ser Arg
    130                 135                 140

Gly Glu Gly Phe Gly Ile Leu Val Leu Lys Arg Leu Ser Asp Ala Leu
145                 150                 155                 160

Arg Asp Asn Asp Thr Val Arg Ala Val Ile Arg Ala Ser Ser Ser Asn
                165                 170                 175

Gln Asp Gly Lys Ser Pro Gly Ile Thr Gln Pro Thr Lys Gln Ala Gln
            180                 185                 190

Ile Gln Leu Ile Lys Asp Thr Tyr Ala Ala Ala Gly Leu Asp Tyr Thr
        195                 200                 205

Gln Thr Arg Tyr Phe Xaa
    210
```

<210> SEQ ID NO 49
<211> LENGTH: 722
<212> TYPE: DNA
<213> ORGANISM: Parmelia sulcata

<400> SEQUENCE: 49

```
cttgttactc gagactgtct acgaatctct cgagtcggct ggtcagacaa tcgaaggctt      60
gcaaggatcg caaaccgcag tgtatattgg tgtaatgtgc gatgattacg ccgagctcgt     120
gtatcatgat acagagtcaa tcccgaccta tgctgcaact ggtagtgcac gcagcatgat     180
gtcgaaccga atctcttact tctttgactg aaggggccg tcaatgacca ttgatactgc      240
ctgttcctct agtcttgtcg ctgtccacca ggccgttcaa gttctcagga gcggagaatc     300
ccgcgtcgca gtggctgctg ggcaaatct catcttcgga cccagtaagt cttcctaaaa      360
tatgagtagg ctccagtcat tgtgattgct aatcacttca accatttaca gagatgtaca     420
ttgctgagag caacctcaat atgttgtccc caactggscg stcccgaatg tgggacgcta     480
acscggatgg ctatgcacga ggagagggta ttgcatctgt cgtactcaaa actcttagct     540
ctgctatagc agatggtgat accatcgaat gtttgatccg agaaaccggt gtcaaccagg     600
atggccgcac cactggtatc actatgccaa gctccgcagc ccaagccagt ttgatccgtc     660
agacttacgc cagagctggt ttggacctgg cgaagcaagc tgatcggcct caattctttg     720
ag                                                                    722
```

<210> SEQ ID NO 50
<211> LENGTH: 218
<212> TYPE: PRT
<213> ORGANISM: Parmelia sulcata

```
<220> FEATURE:
<221> NAME/KEY: SITE
<222> LOCATION: (139)
<223> OTHER INFORMATION: Xaa=unknown amino acid

<400> SEQUENCE: 50
```

```
Leu Leu Leu Glu Thr Val Tyr Glu Ser Leu Glu Ser Ala Gly Gln Thr
  1               5                  10                  15

Ile Glu Gly Leu Gln Gly Ser Gln Thr Ala Val Tyr Ile Gly Val Met
             20                  25                  30

Cys Asp Asp Tyr Ala Glu Leu Val Tyr His Asp Thr Glu Ser Ile Pro
         35                  40                  45

Thr Tyr Ala Ala Thr Gly Ser Ala Arg Ser Met Met Ser Asn Arg Ile
     50                  55                  60

Ser Tyr Phe Phe Asp Trp Lys Gly Pro Ser Met Thr Ile Asp Thr Ala
 65                  70                  75                  80

Cys Ser Ser Ser Leu Val Ala Val His Gln Ala Val Gln Val Leu Arg
                 85                  90                  95

Ser Gly Glu Ser Arg Val Ala Val Ala Ala Gly Ala Asn Leu Ile Phe
            100                 105                 110

Gly Pro Lys Met Tyr Ile Ala Glu Ser Asn Leu Asn Met Leu Ser Pro
        115                 120                 125

Thr Gly Arg Ser Arg Met Trp Asp Ala Asn Xaa Asp Gly Tyr Ala Arg
    130                 135                 140

Gly Glu Gly Ile Ala Ser Val Val Leu Lys Thr Leu Ser Ser Ala Ile
145                 150                 155                 160

Ala Asp Gly Asp Thr Ile Glu Cys Leu Ile Arg Glu Thr Gly Val Asn
                165                 170                 175

Gln Asp Gly Arg Thr Thr Gly Ile Thr Met Pro Ser Ser Ala Ala Gln
            180                 185                 190

Ala Ser Leu Ile Arg Gln Thr Tyr Ala Arg Ala Gly Leu Asp Leu Ala
        195                 200                 205

Lys Gln Ala Asp Arg Pro Gln Phe Phe Glu
    210                 215

<210> SEQ ID NO 51
<211> LENGTH: 703
<212> TYPE: DNA
<213> ORGANISM: Peltigera neopolydactyla

<400> SEQUENCE: 51
```

```
aatattactt gagacgatct acgaaggact tgagtccgcc ggacttacca taaaggggct      60
gcaaggttcc caaacagctg tgtacgtcgg tctcatggct ggagactact atgacatcca     120
gatgcgcgac atagagactt tgcctcgata tgctgctacc gggactgctc gtagcattat     180
gagcaaccga gtctcttatt tctttgattg gaaaggtccg tccatgacaa ttgatacggc     240
ctgctcttct tccctcgttg ccgttcatca ggctgtcgag attctccgga gaggtgatgt     300
taccatggct gtggctgccg cgccaaccct gatctatggt cctgaggctt atatatccga     360
gtcgaatctg aacatgctgt cgccgagcgg aagatcgcgc atgtgggatt caagtgcgga     420
cggatacggc cgcggagaag ggtttgcggc agtgatgttg aagaccctga gcgctgcaat     480
tcgtgatgga gatcatatcg agtgcattat ccgggagaca ggaattaacc aggatggcag     540
aacagccgga attaccatgc caagtgctgt cagccagact cgattgatca agacacata      600
```

```
tgctcgagct ggactcgatt gcaggaaaga agcggagaga tgccagtact ttgaaggtaa       660
gcgaataact tttcttgata aacgcactta ctaagatctt taa                        703
```

<210> SEQ ID NO 52
<211> LENGTH: 234
<212> TYPE: PRT
<213> ORGANISM: Peltigera neopolydactyla
<220> FEATURE:
<221> NAME/KEY: SITE
<222> LOCATION: (231)
<223> OTHER INFORMATION: Xaa=unknown amino acid
<221> NAME/KEY: SITE
<222> LOCATION: (234)
<223> OTHER INFORMATION: Xaa=unknown amino acid

<400> SEQUENCE: 52

```
Ile Leu Leu Glu Thr Ile Tyr Glu Gly Leu Glu Ser Ala Gly Leu Thr
  1               5                  10                  15

Ile Lys Gly Leu Gln Gly Ser Gln Thr Ala Val Tyr Val Gly Leu Met
             20                  25                  30

Ala Gly Asp Tyr Tyr Asp Ile Gln Met Arg Asp Ile Glu Thr Leu Pro
         35                  40                  45

Arg Tyr Ala Ala Thr Gly Thr Ala Arg Ser Ile Met Ser Asn Arg Val
     50                  55                  60

Ser Tyr Phe Phe Asp Trp Lys Gly Pro Ser Met Thr Ile Asp Thr Ala
 65                  70                  75                  80

Cys Ser Ser Ser Leu Val Ala Val His Gln Ala Val Glu Ile Leu Arg
                 85                  90                  95

Arg Gly Asp Val Thr Met Ala Val Ala Ala Gly Ala Asn Leu Ile Tyr
            100                 105                 110

Gly Pro Glu Ala Tyr Ile Ser Glu Ser Asn Leu Asn Met Leu Ser Pro
        115                 120                 125

Ser Gly Arg Ser Arg Met Trp Asp Ser Ser Ala Asp Gly Tyr Gly Arg
    130                 135                 140

Gly Glu Gly Phe Ala Ala Val Met Leu Lys Thr Leu Ser Ala Ala Ile
145                 150                 155                 160

Arg Asp Gly Asp His Ile Glu Cys Ile Ile Arg Glu Thr Gly Ile Asn
                165                 170                 175

Gln Asp Gly Arg Thr Ala Gly Ile Thr Met Pro Ser Ala Val Ser Gln
            180                 185                 190

Thr Arg Leu Ile Lys Asp Thr Tyr Ala Arg Ala Gly Leu Asp Cys Arg
        195                 200                 205

Lys Glu Ala Glu Arg Cys Gln Tyr Phe Glu Gly Lys Arg Ile Thr Phe
    210                 215                 220

Leu Asp Lys Arg Thr Tyr Xaa Asp Leu Xaa
225                 230
```

<210> SEQ ID NO 53
<211> LENGTH: 643
<212> TYPE: DNA
<213> ORGANISM: Peltigera neopolydactyla

<400> SEQUENCE: 53

```
gctgttgctg gaggtaagtt gggaagcttt agaaaatgct ggcaaagcac ctgaaaagct        60
agcaggaagc aatacaggtg tatttgttgg cattagcaac tttgattatt cacagttgca       120
aattaatcaa accgctcaac tagatgccta tacaggcact ggcaatgctt ttagcatcgc       180
agctaaccgt ctttcctatt ttctagactt gcacggacct agctgggcag tagacacagc       240
```

-continued

```
ctgttcatca tctctagtag cagtccatca agcttgccaa agtctgcgtc aaggagaatg      300
cgaactagcc ctcgctggtg gtgtaaatct gattctcacc ccacaattaa ccatcacttt      360
ttcccaagct gggatgatgg ctgctgatgg tcgttgcaaa acctttgatg ctgatgctga      420
tggttacgtg cggggcgaag gttgtggtgt tgtaattctc aagcgtttgg ccaacgctca      480
acgagatgga gacaatattt tggcagttat taaaggttcg gcagttaacc aagatggtcg      540
cagcaacgga ttgacagcac ccaacggtca tgcccaacaa gcagttattc gccaagcatt      600
acaaaatgcc aatgttgcag ctgccgagat tagctatgta gaa                       643
```

<210> SEQ ID NO 54
<211> LENGTH: 214
<212> TYPE: PRT
<213> ORGANISM: Peltigera neopolydactyla

<400> SEQUENCE: 54

```
Leu Leu Leu Glu Val Ser Trp Glu Ala Leu Glu Asn Ala Gly Lys Ala
 1               5                  10                  15

Pro Glu Lys Leu Ala Gly Ser Asn Thr Gly Val Phe Val Gly Ile Ser
            20                  25                  30

Asn Phe Asp Tyr Ser Gln Leu Gln Ile Asn Gln Thr Ala Gln Leu Asp
        35                  40                  45

Ala Tyr Thr Gly Thr Gly Asn Ala Phe Ser Ile Ala Ala Asn Arg Leu
    50                  55                  60

Ser Tyr Phe Leu Asp Leu His Gly Pro Ser Trp Ala Val Asp Thr Ala
65                  70                  75                  80

Cys Ser Ser Ser Leu Val Ala Val His Gln Ala Cys Gln Ser Leu Arg
                85                  90                  95

Gln Gly Glu Cys Glu Leu Ala Leu Ala Gly Gly Val Asn Leu Ile Leu
            100                 105                 110

Thr Pro Gln Leu Thr Ile Thr Phe Ser Gln Ala Gly Met Met Ala Ala
        115                 120                 125

Asp Gly Arg Cys Lys Thr Phe Asp Ala Asp Ala Asp Gly Tyr Val Arg
    130                 135                 140

Gly Glu Gly Cys Gly Val Val Ile Leu Lys Arg Leu Ala Asn Ala Gln
145                 150                 155                 160

Arg Asp Gly Asp Asn Ile Leu Ala Val Ile Lys Gly Ser Ala Val Asn
                165                 170                 175

Gln Asp Gly Arg Ser Asn Gly Leu Thr Ala Pro Asn Gly His Ala Gln
            180                 185                 190

Gln Ala Val Ile Arg Gln Ala Leu Gln Asn Ala Asn Val Ala Ala Ala
        195                 200                 205

Glu Ile Ser Tyr Val Glu
    210
```

<210> SEQ ID NO 55
<211> LENGTH: 655
<212> TYPE: DNA
<213> ORGANISM: Peltigera neopolydactyla

<400> SEQUENCE: 55

```
tcttttttg gagtgtgctt gggaagcgct ggaaaatgct ggttatgacc cgaaaacaga       60 caaaatcta attggcgttt atgcaggggg gaatctaagt acctacttac ttaacaatct      120
cgcctcacac cctgaactca ttaaagcgct ggagtcacaa attacaattg ctaatgataa      180
```

-continued

```
ggactttata tgcacacgag tttcttacaa attaaacctg aaagggccga gtattagtgt    240
cggcacggcc tgctctacgt cattagtagc agttcacttg gcatgtcgag gattgctaag    300
ttaccagtgt gatatggcac tggctggcgg tattgcgata caagttccac aaaaacaagg    360
ttatttctat caagaaggtg gcatggcctc tcctgatggc cactgtcggg cctttgatgc    420
taaagcacaa ggtagccctt ttggcaaagg agcaggtatt gtcgtgctga aaagattgga    480
agatgctgta gctgatggag actgcattta tgcggttatc aaaggttcag ccatcaataa    540
cgacggttcc gagaaggtga gttacaccgc acccagtgta acaggccaag cagaagtgat    600
tgccgaggct caggcgatcg ctaactttga ttctgaaaca atcacctaca ttgaa         655
```

<210> SEQ ID NO 56
<211> LENGTH: 217
<212> TYPE: PRT
<213> ORGANISM: Peltigera neopolydactyla

<400> SEQUENCE: 56

```
Leu Phe Leu Glu Cys Ala Trp Glu Ala Leu Glu Asn Ala Gly Tyr Asp
 1               5                  10                  15

Pro Lys Thr Asp Lys Asn Leu Ile Gly Val Tyr Ala Gly Gly Asn Leu
            20                  25                  30

Ser Thr Tyr Leu Leu Asn Asn Leu Ala Ser His Pro Glu Leu Ile Lys
        35                  40                  45

Ala Leu Glu Ser Gln Ile Thr Ile Ala Asn Asp Lys Asp Phe Ile Cys
    50                  55                  60

Thr Arg Val Ser Tyr Lys Leu Asn Leu Lys Gly Pro Ser Ile Ser Val
65                  70                  75                  80

Gly Thr Ala Cys Ser Thr Ser Leu Val Ala Val His Leu Ala Cys Arg
                85                  90                  95

Gly Leu Leu Ser Tyr Gln Cys Asp Met Ala Leu Ala Gly Gly Ile Ala
            100                 105                 110

Ile Gln Val Pro Gln Lys Gln Gly Tyr Phe Tyr Gln Glu Gly Gly Met
        115                 120                 125

Ala Ser Pro Asp Gly His Cys Arg Ala Phe Asp Ala Lys Ala Gln Gly
    130                 135                 140

Ser Pro Phe Gly Lys Gly Ala Gly Ile Val Val Leu Lys Arg Leu Glu
145                 150                 155                 160

Asp Ala Val Ala Asp Gly Asp Cys Ile Tyr Ala Val Ile Lys Gly Ser
                165                 170                 175

Ala Ile Asn Asn Asp Gly Ser Glu Lys Val Ser Tyr Thr Ala Pro Ser
            180                 185                 190

Val Thr Gly Gln Ala Glu Val Ile Ala Glu Ala Gln Ala Ile Ala Asn
        195                 200                 205

Phe Asp Ser Glu Thr Ile Thr Tyr Ile
    210                 215
```

<210> SEQ ID NO 57
<211> LENGTH: 765
<212> TYPE: DNA
<213> ORGANISM: Peltigera neopolydactyla

<400> SEQUENCE: 57

```
attgctgctt gaaaacgtct atgaagctct tgaaaacggt gagcggttct tcaagagaat     60
attgatgcat caatatgcta acttgatgtc aatcatcagc tggtattcct ctgagcgagt    120
ccgtctcttc taaacacctcc gtttatgttg gctcattcgg tgatgactat aagacgattc   180
```

```
tcaataccga ttttgagagt tgggtcaagt acaaaggcac cggtgtctat aactcgattc      240
tggccaatcg aatcagctgg ttctacgact ttaaaggagc cagcgtcacg ctagataccg      300
catgctcgag tagcttggta gccgtgcata tggcttgcca ggatttgagg ttgggagagt      360
ctagaatggt cagtgtattt ctctattgaa aagtactaga ggattctaat tgacgtattt      420
ggataccagt ccgttgtcgg cggtgtcaac atcattggcc atccgttgct cgtccacgat      480
ctaagcaagc tcggagcgct ctcctgat ggcgtgtgct acactttcga tgaacgggcc        540
aatggatatt cccggggaga aggtgtcggc accatcgttc tcaaacggct ctctgacgca      600
atcgaagatg gtgataccat tcgcgctatc atccgtgcaa gcgggtgcaa tcaagacggt      660
aaaacagcag gtatatttgt cccttcagtc caagcccagg agcgacttat ccgggatacc      720
tatgagaagg ctgggcttga ccggacacgc acgacatatt tggaa                     765
```

<210> SEQ ID NO 58
<211> LENGTH: 216
<212> TYPE: PRT
<213> ORGANISM: Peltigera neopolydactyla

<400> SEQUENCE: 58

```
Leu Leu Leu Glu Asn Val Tyr Glu Ala Leu Glu Asn Ala Gly Ile Pro
  1               5                  10                  15

Leu Ser Glu Ser Val Ser Ser Asn Thr Ser Val Tyr Val Gly Ser Phe
             20                  25                  30

Gly Asp Asp Tyr Lys Thr Ile Leu Asn Thr Asp Phe Glu Ser Trp Val
         35                  40                  45

Lys Tyr Lys Gly Thr Gly Val Tyr Asn Ser Ile Leu Ala Asn Arg Ile
     50                  55                  60

Ser Trp Phe Tyr Asp Phe Lys Gly Ala Ser Val Thr Leu Asp Thr Ala
 65                  70                  75                  80

Cys Ser Ser Ser Leu Val Ala Val His Met Ala Cys Gln Asp Leu Arg
                 85                  90                  95

Leu Gly Glu Ser Arg Met Val Ser Ser Val Val Gly Val Asn Ile
                100                 105                 110

Ile Gly His Pro Leu Leu Val His Asp Leu Ser Lys Leu Gly Ala Leu
            115                 120                 125

Ser Pro Asp Gly Val Cys Tyr Thr Phe Asp Glu Arg Ala Asn Gly Tyr
        130                 135                 140

Ser Arg Gly Glu Gly Val Gly Thr Ile Val Leu Lys Arg Leu Ser Asp
145                 150                 155                 160

Ala Ile Glu Asp Gly Asp Thr Ile Arg Ala Ile Ile Arg Ala Ser Gly
                165                 170                 175

Cys Asn Gln Asp Gly Lys Thr Ala Gly Ile Phe Val Pro Ser Val Gln
            180                 185                 190

Ala Gln Glu Arg Leu Ile Arg Asp Thr Tyr Glu Lys Ala Gly Leu Asp
        195                 200                 205

Arg Thr Arg Thr Thr Tyr Leu Glu
    210                 215
```

<210> SEQ ID NO 59
<211> LENGTH: 709
<212> TYPE: DNA
<213> ORGANISM: Peltigera neopolydactyla

<400> SEQUENCE: 59

```
taagttactg gaaacagcat atactgcgtt tgagaacggt gagtacgcct tgcgtcgtat    60 cccctcccccc ctcatggaag atctcaatct gatctcgtga acagccggc atcgggttag   120 aagcggcacg aggatcaaac acttcagtac ataggttg tttaatatc gactatacaa      180 gcaaccatag tagagatcca gagcagatgc acaaatatac ggggactgga ggagcacctt   240
ccatgctgtc gaacagactg agttggtttt tcgatctgag aggaccgagc ttgaccttgg    300
acacggcatg ctctagtagc atggttgcgc ttgatttagc atgccagact ttgcaaagtg    360
gacaatctga catgggtctt gtcgggggtt gtaatctcat ctacagcgtc gacatgacca    420
tggctctatc caagcttgga tttctctccc ataacagtcg gtgctacagt tttgaccatc    480
gagcggatgg gtacgccaga ggtgaaggct ttggagtttt aattctcaaa cgtgtcgaag    540
acgccatacg agatggggat actatacgag gagtcattcg attaacaagc tccaatcaag    600
acggccatac tccgggaata acaatgccca gcagagacgc ccaagcaagt ttgattagaa    660
agacatacca acaagctgga ttagatatgc agatgacagg ctactttga                709
```

<210> SEQ ID NO 60
<211> LENGTH: 213
<212> TYPE: PRT
<213> ORGANISM: Peltigera neopolydactyla

<400> SEQUENCE: 60

```
Lys Leu Leu Glu Thr Ala Tyr Thr Ala Phe Glu Asn Ala Gly Ile Gly
  1               5                  10                  15

Leu Glu Ala Ala Arg Gly Ser Asn Thr Ser Val His Ile Gly Cys Phe
                 20                  25                  30

Asn Ile Asp Tyr Thr Ser Asn His Ser Arg Asp Pro Glu Gln Met His
             35                  40                  45

Lys Tyr Thr Gly Thr Gly Gly Ala Pro Ser Met Leu Ser Asn Arg Leu
         50                  55                  60

Ser Trp Phe Phe Asp Leu Arg Gly Pro Ser Leu Thr Leu Asp Thr Ala
 65                  70                  75                  80

Cys Ser Ser Ser Met Val Ala Leu Asp Leu Ala Cys Gln Thr Leu Gln
                 85                  90                  95

Ser Gly Gln Ser Asp Met Gly Leu Val Gly Gly Cys Asn Leu Ile Tyr
            100                 105                 110

Ser Val Asp Met Thr Met Ala Leu Ser Lys Leu Gly Phe Leu Ser His
        115                 120                 125

Asn Ser Arg Cys Tyr Ser Phe Asp His Arg Ala Asp Gly Tyr Ala Arg
    130                 135                 140

Gly Glu Gly Phe Gly Val Leu Ile Leu Lys Arg Val Glu Asp Ala Ile
145                 150                 155                 160

Arg Asp Gly Asp Thr Ile Arg Gly Val Ile Arg Leu Thr Ser Ser Asn
                165                 170                 175

Gln Asp Gly His Thr Pro Gly Ile Thr Met Pro Ser Arg Asp Ala Gln
            180                 185                 190

Ala Ser Leu Ile Arg Lys Thr Tyr Gln Gln Ala Gly Leu Asp Met Gln
        195                 200                 205

Met Thr Gly Tyr Phe
    210
```

<210> SEQ ID NO 61
<211> LENGTH: 649
<212> TYPE: DNA
<213> ORGANISM: Pseudocyphellaria anthrapsis -continued

<400> SEQUENCE: 61

```
aatgttgctc gagatcacct acgaagccct ggagaacgct ggacttcctt tgagtaaggt     60
tgtcggctct gatacagcct gcttcattgg tggctttaca cgagattatg atgatttgac    120
cacttcggag ctcgcgaaga ccctactcta cacaactacc ggcaacggcc tgacgatgat    180
gtcgaatcgc ttatcctggt tctacgacct tcatggcccg tcggtttcgc tcgacacagc    240
atgttctagc tcgctggttg cactaaacct tgcatgccag acaatccgag catcgacgaa    300
tgactctcga caggcgatag ttggaggtgt caatctcatg ctgctccctg atcagatgac    360
cacgattaat cctctgcatt tcttaagtcc tgatagccaa tgctactcgt ttgatgaccg    420
tgcaaacggt tacacccgtg gagaaggtat tggcatactg gtgctcaagc acatcaatga    480
tgctattcga gatggagact gtataagggc agtaatccgc ggcactgggg tcaactccga    540
tggcaagacc cctggcatta ccttgccaag cacggctgca caagcctctt taattcgcgc    600
aacgtacgcc tcggcagggc tggacccagc tcacaccggc tactttgaa               649
```

<210> SEQ ID NO 62
<211> LENGTH: 216
<212> TYPE: PRT
<213> ORGANISM: Pseudocyphellaria anthrapsis

<400> SEQUENCE: 62

```
Met Leu Leu Glu Ile Thr Tyr Glu Ala Leu Glu Asn Ala Gly Leu Pro
  1               5                  10                  15

Leu Ser Lys Val Val Gly Ser Asp Thr Ala Cys Phe Ile Gly Gly Phe
             20                  25                  30

Thr Arg Asp Tyr Asp Asp Leu Thr Thr Ser Glu Leu Ala Lys Thr Leu
         35                  40                  45

Leu Tyr Thr Thr Thr Gly Asn Gly Leu Thr Met Met Ser Asn Arg Leu
     50                  55                  60

Ser Trp Phe Tyr Asp Leu His Gly Pro Ser Val Ser Leu Asp Thr Ala
 65                  70                  75                  80

Cys Ser Ser Ser Leu Val Ala Leu Asn Leu Ala Cys Gln Thr Ile Arg
                 85                  90                  95

Ala Ser Thr Asn Asp Ser Arg Gln Ala Ile Val Gly Gly Val Asn Leu
            100                 105                 110

Met Leu Leu Pro Asp Gln Met Thr Thr Ile Asn Pro Leu His Phe Leu
        115                 120                 125

Ser Pro Asp Ser Gln Cys Tyr Ser Phe Asp Asp Arg Ala Asn Gly Tyr
    130                 135                 140

Thr Arg Gly Glu Gly Ile Gly Ile Leu Val Leu Lys His Ile Asn Asp
145                 150                 155                 160

Ala Ile Arg Asp Gly Asp Cys Ile Arg Ala Val Ile Arg Gly Thr Gly
                165                 170                 175

Val Asn Ser Asp Gly Lys Thr Pro Gly Ile Thr Leu Pro Ser Thr Ala
            180                 185                 190

Ala Gln Ala Ser Leu Ile Arg Ala Thr Tyr Ala Ser Ala Gly Leu Asp
        195                 200                 205

Pro Ala His Thr Gly Tyr Phe Glu
    210                 215
```

<210> SEQ ID NO 63
<211> LENGTH: 747
<212> TYPE: DNA

<213> ORGANISM: Siphula certities

<400> SEQUENCE: 63

```
tatgctactt gaatgcacat acgaagcgtt agagaatggt cagtgagcta cgagccgatt    60
ttcatatatc atggctaaca agttgaagct ggcatacctc tagataaagt agtaggagaa   120
cccgtagggg tgtacgtcgg ctcagctagt tccgattact cggacatcgt gaactcagac   180
ggcgagatgg tctccactta cacggccacg gggttggccg caacgatgat ggcaaaccgc   240
atatcctatt tctatgatct ccgggggcca agcttcacat ggacacggc gtgttcatcg    300
agtttgatgg cgttacacct agcgtgccaa agtcttcgag tcggtgaatc gaagcaagcc   360
attgtgggcg gggtccacct tgtactgagc ccggattgta tgacttcgat gagtttatta   420
gggtaagacc ttcaaaatct ccatgcagaa tttctaaatc taacctacca ccctagtttg   480
ttctctaatg acggccgatc ctacacttat gaccatcgag gtactggtta tgggcgcggc   540
gaaggtattg ctaccttagt aataaaacct cttaaagatg cgatggaagc cggtgataac   600
atccgggcca tcatccgcaa tagtggggca aatcaagatg tcgaacacc aggtgtgact    660
tttccaagtc aagatgctca gatagatctt atgagatcgg tatatcgttc cgctggactt   720
gatgtacttg ataccggcta cgtggaa                                      747
```

<210> SEQ ID NO 64
<211> LENGTH: 213
<212> TYPE: PRT
<213> ORGANISM: Siphula certities
<220> FEATURE:
<221> NAME/KEY: SITE
<222> LOCATION: (135)
<223> OTHER INFORMATION: Xaa=unknown amino acid
<221> NAME/KEY: SITE
<222> LOCATION: (145)
<223> OTHER INFORMATION: Xaa=unknown amino acid

<400> SEQUENCE: 64

```
Met Leu Leu Glu Cys Thr Tyr Glu Ala Leu Glu Asn Ala Gly Ile Pro
  1               5                  10                  15
Leu Asp Lys Val Val Gly Glu Pro Val Gly Val Tyr Val Gly Ser Ala
                 20                  25                  30
Ser Ser Asp Tyr Ser Asp Ile Val Asn Ser Asp Gly Glu Val Ser Thr
             35                  40                  45
Tyr Thr Ala Thr Gly Leu Ala Ala Thr Met Met Ala Asn Arg Ile Ser
         50                  55                  60
Tyr Phe Tyr Asp Leu Arg Gly Pro Ser Phe Thr Leu Asp Thr Ala Cys
 65                  70                  75                  80
Ser Ser Ser Leu Met Ala Leu His Leu Ala Cys Gln Ser Leu Arg Val
                 85                  90                  95
Gly Glu Ser Lys Gln Ala Ile Val Gly Gly Val His Leu Val Leu Ser
                100                 105                 110
Pro Asp Cys Met Thr Ser Met Ser Leu Leu Gly Leu Phe Ser Asn Asp
                115                 120                 125
Gly Arg Ser Tyr Thr Tyr Xaa His Arg Gly Thr Gly Tyr Gly Arg Gly
                130                 135                 140
Xaa Gly Ile Ala Thr Leu Val Ile Lys Pro Leu Lys Asp Ala Met Glu
145                 150                 155                 160
Ala Gly Asp Asn Ile Arg Ala Ile Ile Arg Asn Ser Gly Ala Asn Gln
                165                 170                 175
```

```
Asp Gly Arg Thr Pro Gly Val Thr Phe Pro Ser Gln Asp Ala Gln Ile
            180                 185                 190

Asp Leu Met Arg Ser Val Tyr Arg Ser Ala Gly Leu Asp Val Leu Asp
        195                 200                 205

Thr Gly Tyr Val Glu
    210

<210> SEQ ID NO 65
<211> LENGTH: 643
<212> TYPE: DNA
<213> ORGANISM: Siphula certities

<400> SEQUENCE: 65
aattctactt gaagtcgcct atcaagcaat ggagtcaagc ggctgcttac ggaaccatcg      60
acgcgaagct ggggatcctg tgggatgttt tattggagct agctttgccg aatatcttga    120
caacacctgt tctaatccgc caaccagcta tacttccact ggcaccatca gagctttcca    180
ctgcggtaga ctcagttatt actttggatg gagcggtcct gccgaggtca ttgatacagc    240
ttgctcctct tcgttggttg ctatcaatcg agcttgcaag tcagtgcagg cgggtgaatg    300
tacaatggct cttactggtg gagtgaacat tataactggt atccacaact tcttagatct    360
ggcaaaggct ggcttyttaa gccccacagg ccaatgcaga cccttgacc agtctgcaga     420 tgggtattgt cgctcagaag gagcaggact tgttgtacta aaactgttaa gccaagccat    480
agcagatgga gatcaaattt tcggagttat tccaagtgtg tccaccaacc aaggcggatt    540
gtcatcttca attacgattc ctcattcgcc tgcacaaaaa aagttgtatc aaaccgtgct    600
tcggcaagcc ggcatgaagc tagaacaggt tagctacgta gag                       643

<210> SEQ ID NO 66
<211> LENGTH: 214
<212> TYPE: PRT
<213> ORGANISM: Siphula certities

<400> SEQUENCE: 66

Ile Leu Leu Glu Val Ala Tyr Gln Ala Met Glu Ser Ser Gly Cys Leu
  1               5                  10                  15

Arg Asn His Arg Arg Glu Ala Gly Asp Pro Val Gly Cys Phe Ile Gly
             20                  25                  30

Ala Ser Phe Ala Glu Tyr Leu Asp Asn Thr Cys Ser Asn Pro Pro Thr
         35                  40                  45

Ser Tyr Thr Ser Thr Gly Thr Ile Arg Ala Phe His Cys Gly Arg Leu
     50                  55                  60

Ser Tyr Tyr Phe Gly Trp Ser Gly Pro Ala Glu Val Ile Asp Thr Ala
 65                  70                  75                  80

Cys Ser Ser Ser Leu Val Ala Ile Asn Arg Ala Cys Lys Ser Val Gln
                 85                  90                  95

Ala Gly Glu Cys Thr Met Ala Leu Thr Gly Gly Val Asn Ile Ile Thr
            100                 105                 110

Gly Ile His Asn Phe Leu Asp Leu Ala Lys Ala Gly Phe Leu Ser Pro
        115                 120                 125

Thr Gly Gln Cys Arg Pro Phe Asp Gln Ser Ala Asp Gly Tyr Cys Arg
    130                 135                 140

Ser Glu Gly Ala Gly Leu Val Val Leu Lys Leu Leu Ser Gln Ala Ile
145                 150                 155                 160
```

Ala Asp Gly Asp Gln Ile Phe Gly Val Ile Pro Ser Val Ser Thr Asn
                165                 170                 175

Gln Gly Gly Leu Ser Ser Ser Ile Thr Ile Pro His Ser Pro Ala Gln
            180                 185                 190

Lys Lys Leu Tyr Gln Thr Val Leu Arg Gln Ala Gly Met Lys Leu Glu
        195                 200                 205

Gln Val Ser Tyr Val Glu
    210

<210> SEQ ID NO 67
<211> LENGTH: 809
<212> TYPE: DNA
<213> ORGANISM: Thamnolia vermicularis
<220> FEATURE:
<221> NAME/KEY: modified_base
<222> LOCATION: (802)
<223> OTHER INFORMATION: n=a, c, g or t

<400> SEQUENCE: 67
aggaaactac tagaggtcgt gtttgaatgt tttgagagtg ccggtacacc acttcacgca    60
gtttcaggag ctaatattgg ctgctatgtt gggaatttta cgttggatta tcttgtcatg   120
cagtctaagg atacagactc ttttcatcga tatactgctc caggaatggg acctacattg   180
ttagctaacc gcataagtca tgttttttaat cttcaaggtc caagtgttat gcttgataca   240
gcgtgttctt catcgatcta cgctcttcat gcagcttgtg tggccttgaa tgcagatgag   300
tgcaatgcag caattgttgc tggggcaaac ctaatccagt cacctgagtg gcatcttgca   360
gtctccaaat caggtgtgat ttcacaaact tccacgtgtc acactttcga tgctagtgcg   420
gatggttatg ggcgaggcga gggcgttggg gccctctatc tcaagcgtct aagtgacgca   480
atccgagatc gagatcctat acggtctgtt attcgtggta cagctgttaa taggttagta   540
catcctctta cctttctttc atggattagc gagaattagg gttccaaatg tttgaaagct   600
cgggttctaa tattcattca ctggactagt aatggcaaga caaacggcat cagtcagcct   660
agtgctttgg cacaggaagc tgtgattaaa aaagcttatg caaaggcggg attacctgtt   720
accgagactg actatgttga ggtaagtgag ctatgtttaa atcagaaaac gtcatgccat   780
tatttcttat ccttcactga nctcttaca                                     809

<210> SEQ ID NO 68
<211> LENGTH: 237
<212> TYPE: PRT
<213> ORGANISM: Thamnolia vermicularis
<220> FEATURE:
<221> NAME/KEY: SITE
<222> LOCATION: (235)
<223> OTHER INFORMATION: Xaa=unknown amino acid

<400> SEQUENCE: 68

Arg Lys Leu Leu Glu Val Val Phe Glu Cys Phe Glu Ser Ala Gly Thr
  1               5                  10                  15

Pro Leu His Ala Val Ser Gly Ala Asn Ile Gly Cys Tyr Val Gly Asn
             20                  25                  30

Phe Thr Leu Asp Tyr Leu Val Met Gln Ser Lys Asp Thr Asp Ser Phe
         35                  40                  45

His Arg Tyr Thr Ala Pro Gly Met Gly Pro Thr Leu Leu Ala Asn Arg
     50                  55                  60

Ile Ser His Val Phe Asn Leu Gln Gly Pro Ser Val Met Leu Asp Thr
 65                  70                  75                  80

```
Ala Cys Ser Ser Ser Ile Tyr Ala Leu His Ala Cys Val Ala Leu
                85                  90                  95

Asn Ala Asp Glu Cys Asn Ala Ala Ile Val Ala Gly Ala Asn Leu Ile
            100                 105                 110

Gln Ser Pro Glu Trp His Leu Ala Val Ser Lys Ser Gly Val Ile Ser
        115                 120                 125

Gln Thr Ser Thr Cys His Thr Phe Asp Ala Ser Ala Asp Gly Tyr Gly
    130                 135                 140

Arg Gly Glu Gly Val Gly Ala Leu Tyr Leu Lys Arg Leu Ser Asp Ala
145                 150                 155                 160

Ile Arg Asp Arg Asp Pro Ile Arg Ser Val Ile Arg Gly Thr Ala Val
                165                 170                 175

Asn Ser Asn Gly Lys Thr Asn Gly Ile Ser Gln Pro Ser Ala Leu Ala
            180                 185                 190

Gln Glu Ala Val Ile Lys Lys Ala Tyr Ala Lys Ala Gly Leu Pro Val
        195                 200                 205

Thr Glu Thr Asp Tyr Val Glu Val Ser Glu Leu Cys Leu Asn Gln Lys
    210                 215                 220

Thr Ser Cys His Tyr Phe Leu Ser Phe Thr Xaa Leu Leu
225                 230                 235
```

<210> SEQ ID NO 69
<211> LENGTH: 658
<212> TYPE: DNA
<213> ORGANISM: Usnea florida

<400> SEQUENCE: 69

```
tttgctcctt gagactgtct acgaagctct ggaagcaggc ggtcacacga ttgaagcgct    60
acgaggatct gatacgtctg tctttacagg caccatgggc gtcgactaca cgatactgt   120
tatacgggac ctgaacgtca tcccgacgta ctttgctact ggagtaaatc gagctatcat   180
ctcgaaccga gtctcatact tctttgactg gcatgggccg agcatgacca tcgacacagc   240
ctgttcatcc agtctcgtcg ccgtgcacca aggagtgaaa gctcttcgga gtggggagtc   300
gcgtactgcc ctggcatgtg ggacgcaggt cattctaaat cccgagatgt atgttattga   360
gagcaagctg aaaatgcttt tcctacgggg ccgctcccgc atgtgggatg cggacgcgga   420
tggctacgct cgtggggagg gcgtagcggc tgtagtgctg aaacggctca gtgacgctat   480
tgcggatgga satcgcatcg agtgcatcat ccgtgagaca gggtccaacc aagacggcca   540
ttcaaatggt atcacggtgc cgagtacgga ggcccaagcg gccctcatcc accaaaccta   600
tgccagagct ggtctagacc cggaaaataa ccctcacgac cgccctcagt tcttcgaa    658
```

<210> SEQ ID NO 70
<211> LENGTH: 219
<212> TYPE: PRT
<213> ORGANISM: Usnea florida
<220> FEATURE:
<221> NAME/KEY: SITE
<222> LOCATION: (164)
<223> OTHER INFORMATION: Xaa=unknown amino acid

<400> SEQUENCE: 70

```
Leu Leu Leu Glu Thr Val Tyr Glu Ala Leu Glu Ala Gly Gly His Thr
  1               5                  10                  15

Ile Glu Ala Leu Arg Gly Ser Asp Thr Ser Val Phe Thr Gly Thr Met
             20                  25                  30
```

Gly Val Asp Tyr Asn Asp Thr Val Ile Arg Asp Leu Asn Val Ile Pro
            35                  40                  45

Thr Tyr Phe Ala Thr Gly Val Asn Arg Ala Ile Ile Ser Asn Arg Val
        50                  55                  60

Ser Tyr Phe Phe Asp Trp His Gly Pro Ser Met Thr Ile Asp Thr Ala
65                  70                  75                  80

Cys Ser Ser Ser Leu Val Ala Val His Gln Gly Val Lys Ala Leu Arg
                85                  90                  95

Ser Gly Glu Ser Arg Thr Ala Leu Ala Cys Gly Thr Gln Val Ile Leu
            100                 105                 110

Asn Pro Glu Met Tyr Val Ile Glu Ser Lys Leu Lys Met Leu Ser Pro
        115                 120                 125

Thr Gly Arg Ser Arg Met Trp Asp Ala Asp Ala Asp Gly Tyr Ala Arg
    130                 135                 140

Gly Glu Gly Val Ala Ala Val Val Leu Lys Arg Leu Ser Asp Ala Ile
145                 150                 155                 160

Ala Asp Gly Xaa Arg Ile Glu Cys Ile Ile Arg Glu Thr Gly Ser Asn
                165                 170                 175

Gln Asp Gly His Ser Asn Gly Ile Thr Val Pro Ser Thr Glu Ala Gln
            180                 185                 190

Ala Ala Leu Ile His Gln Thr Tyr Ala Arg Ala Gly Leu Asp Pro Glu
        195                 200                 205

Asn Asn Pro His Asp Arg Pro Gln Phe Phe Glu
    210                 215

<210> SEQ ID NO 71
<211> LENGTH: 753
<212> TYPE: DNA
<213> ORGANISM: Usnea florida

<400> SEQUENCE: 71
tgggctactc gagactgctt acaaggcgtt cgaaaacggt gagtcttgaa gctgcacaga      60
tcaagacaag aacactaaat ctctcagcgg gcatacgcat agaagaagcc gctggctcta     120
gaacttcagt tcatatcggg agtttcactc atgattggag agacatcctc caaagggatc     180
cactaatgga tgttagctac atagctaccg caaccgaggt ttctatgcta gcgagtcgac     240
tcagctggtt ttatgatcta agtgggccya gcatctcctt ggatacagcg tgttcgagta     300
gcttaatggc tttacatctc gcctgccaga gtctaaagag tcgagaggcc gacatggtaa     360
ggctatgcta ctttctggct cactcaaact gttttccata tctgatgctt gcacagggcc     420
ttgttgggag gggctaatct tcttttggat cctgtagggg ttattggcat aacaaatgtt     480
ggcatgcttt cgccagatgg cattagttac agctttgatc atcgtgcaaa cgggtatgcc     540
cgaggagaag ggttcggagt cgttgtcatc aaacgcttgg acgatgctct cagacatggc     600
gatactattc gcggtatcgt tcgtgccaca ggatcgaatc aagatggaag aactccaggg     660
attacccaac tgatggagc cgcgcaagaa gagctcatcc gagacactta caaagctgct     720
ggcttagata tgaggctagt aaggtattct taa                                   753

<210> SEQ ID NO 72
<211> LENGTH: 213
<212> TYPE: PRT
<213> ORGANISM: Usnea florida

<400> SEQUENCE: 72

-continued

```
Gly Leu Leu Glu Thr Ala Tyr Lys Ala Phe Glu Asn Ala Gly Ile Arg
  1               5                  10                  15

Ile Glu Glu Ala Ala Gly Ser Arg Thr Ser Val His Ile Gly Ser Phe
                 20                  25                  30

Thr His Asp Trp Arg Asp Ile Leu Gln Arg Asp Pro Leu Met Asp Val
             35                  40                  45

Ser Tyr Ile Ala Thr Ala Thr Glu Val Ser Met Leu Ala Ser Arg Leu
         50                  55                  60

Ser Trp Phe Tyr Asp Leu Ser Gly Pro Ser Ile Ser Leu Asp Thr Ala
 65                  70                  75                  80

Cys Ser Ser Ser Leu Met Ala Leu His Leu Ala Cys Gln Ser Leu Lys
                 85                  90                  95

Ser Arg Glu Ala Asp Met Gly Leu Val Gly Gly Ala Asn Leu Leu Leu
                100                 105                 110

Asp Pro Val Gly Val Ile Gly Ile Thr Asn Val Gly Met Leu Ser Pro
            115                 120                 125

Asp Gly Ile Ser Tyr Ser Phe Asp His Arg Ala Asn Gly Tyr Ala Arg
        130                 135                 140

Gly Glu Gly Phe Gly Val Val Ile Lys Arg Leu Asp Asp Ala Leu
145                 150                 155                 160

Arg His Gly Asp Thr Ile Arg Gly Ile Val Arg Ala Thr Gly Ser Asn
                165                 170                 175

Gln Asp Gly Arg Thr Pro Gly Ile Thr Gln Pro Asp Gly Ala Ala Gln
                180                 185                 190

Glu Glu Leu Ile Arg Asp Thr Tyr Lys Ala Ala Gly Leu Asp Met Arg
            195                 200                 205

Leu Val Arg Tyr Ser
        210
```

<210> SEQ ID NO 73
<211> LENGTH: 753
<212> TYPE: DNA
<213> ORGANISM: Usnea florida

<400> SEQUENCE: 73

```
attgttgctc gaagtaacct atgaagcttt agagaacggt gggtagttcc aggaagcatt    60
aatcaagaca aagctattgc tcacactttt ccaaaatagc cggaataccc ttgaaccaaa   120
ttgtgggcca ggatgttggg gttttttgttg gcggctcaat gtccgactac cagaacctcc   180
tccacaaaga catcgcaaat ggtcctattt accaagccac tggcactgcc atgagcttcc   240
tagccaaccg aatatcttac atctatgacc tcaagggccc aagcgtaaca gtggacactg   300
catgctcctc gggtctcacg gcacttcatt tagcatgcca gagcatacgc actggtgaga   360
tccgacaagc tttggtcggc ggtgtataca ttatcctaag cccggagaat atgattgcca   420
tgagcatgct ggggtgatgt ctcctgttcc agaaagtaat tgataaaagc taatgccagt   480
agactgtttg gcaccgacgg tctctcatac agctatgatc accgagcaac tggatatgga   540
cgtggtgaag gaggaggcat gatagtctta agtcgctag acgacgcgat ggcaaacgga   600
gacacaatac atgcggtaat tcggcacaca gggacaaatc aggatggtaa gaccagcggc   660
ccaacaatgc ccagtctgga agcccaggag agactcatca agaaagttta cagccaggct   720
ggtctggatc cattggatac agaatatgtc gag                                753
```

<210> SEQ ID NO 74
<211> LENGTH: 214
<212> TYPE: PRT
<213> ORGANISM: Usnea florida

<400> SEQUENCE: 74

```
Leu Leu Leu Glu Val Thr Tyr Glu Ala Leu Glu Asn Ala Gly Ile Pro
 1               5                  10                  15

Leu Asn Gln Ile Val Gly Gln Asp Val Gly Val Phe Val Gly Gly Ser
             20                  25                  30

Met Ser Asp Tyr Gln Asn Leu Leu His Lys Asp Ile Ala Asn Gly Pro
         35                  40                  45

Ile Tyr Gln Ala Thr Gly Thr Ala Met Ser Phe Leu Ala Asn Arg Ile
     50                  55                  60

Ser Tyr Ile Tyr Asp Leu Lys Gly Pro Ser Val Thr Val Asp Thr Ala
 65                  70                  75                  80

Cys Ser Ser Gly Leu Thr Ala Leu His Leu Ala Cys Gln Ser Ile Arg
                 85                  90                  95

Thr Gly Glu Ile Arg Gln Ala Leu Val Gly Gly Val Tyr Ile Ile Leu
            100                 105                 110

Ser Pro Glu Asn Met Ile Ala Met Ser Met Leu Gly Leu Phe Gly Thr
        115                 120                 125

Asp Gly Leu Ser Tyr Ser Tyr Asp His Arg Ala Thr Gly Tyr Gly Arg
    130                 135                 140

Gly Glu Gly Gly Gly Met Ile Val Leu Lys Ser Leu Asp Asp Ala Met
145                 150                 155                 160

Ala Asn Gly Asp Thr Ile His Ala Val Ile Arg His Thr Gly Thr Asn
                165                 170                 175

Gln Asp Gly Lys Thr Ser Gly Pro Thr Met Pro Ser Leu Glu Ala Gln
            180                 185                 190

Glu Arg Leu Ile Lys Lys Val Tyr Ser Gln Ala Gly Leu Asp Pro Leu
        195                 200                 205

Asp Thr Glu Tyr Val Glu
    210
```

<210> SEQ ID NO 75
<211> LENGTH: 692
<212> TYPE: DNA
<213> ORGANISM: Usnea florida

<400> SEQUENCE: 75

```
aatgctgctt gaggtagtct atgaggcgtt agaagacggt aagtctaacg aatttcaatc      60
agtggtcctg agctaattgc gatcaagctg gcattacgct cgacgacatt aagggttccc     120
agacatctgt ctactgtggg agcttcacca acgactaccg tgaaatgctg aacaaagatt     180
tggggtacta ccccaagtac atggccactg gtgttggaaa ctccatctta gccaaccgca     240
tttcatattt ctatgaccta cacgaccaag tgtgactgt cgacacagcc tgctctcttc      300
ccctggtctc attccatatg gcaacagat caatccmaga tggagatgct gacatctcaa     360
tcgtcattgg atcttcgctc cattttgatc ccaacatgtt cgtcactatg acggaccttg     420
ggtttctctc aaccgacggc agatgccgtg cttttgacgc tagcggaaag gggtatgtcc     480
gcggtgaggg catctgcgct gttgttttga acaaaaaatc acgcgctgaa cttcacgaca     540
acaacgttcg atccgtcatt cgtggctcgg atgtcaacca cgacggtgcc aaagacggta     600
```

-continued

```
tcacaatgcc aaactcgaag gctcaggaga gcctcatcag aaagacctac aaaaacgctg    660
gactgagtac aaacgacacc cagtactttg ag                                  692
```

<210> SEQ ID NO 76
<211> LENGTH: 214
<212> TYPE: PRT
<213> ORGANISM: Usnea florida
<220> FEATURE:
<221> NAME/KEY: SITE
<222> LOCATION: (96)
<223> OTHER INFORMATION: Xaa=unknown amino acid

<400> SEQUENCE: 76

```
Met Leu Leu Glu Val Val Tyr Glu Ala Leu Glu Asp Ala Gly Ile Thr
 1               5                  10                  15

Leu Asp Asp Ile Lys Gly Ser Gln Thr Ser Val Tyr Cys Gly Ser Phe
                20                  25                  30

Thr Asn Asp Tyr Arg Glu Met Leu Asn Lys Asp Leu Gly Tyr Tyr Pro
            35                  40                  45

Lys Tyr Met Ala Thr Gly Val Gly Asn Ser Ile Leu Ala Asn Arg Ile
        50                  55                  60

Ser Tyr Phe Tyr Asp Leu His Gly Pro Ser Val Thr Val Asp Thr Ala
 65                  70                  75                  80

Cys Ser Leu Pro Leu Val Ser Phe His Met Gly Asn Arg Ser Ile Xaa
                    85                  90                  95

Asp Gly Asp Ala Asp Ile Ser Ile Val Ile Gly Ser Ser Leu His Phe
                100                 105                 110

Asp Pro Asn Met Phe Val Thr Met Thr Asp Leu Gly Phe Leu Ser Thr
            115                 120                 125

Asp Gly Arg Cys Arg Ala Phe Asp Ala Ser Gly Lys Gly Tyr Val Arg
        130                 135                 140

Gly Glu Gly Ile Cys Ala Val Val Leu Lys Gln Lys Ser Arg Ala Glu
145                 150                 155                 160

Leu His Asp Asn Asn Val Arg Ser Val Ile Arg Gly Ser Asp Val Asn
                    165                 170                 175

His Asp Gly Ala Lys Asp Gly Ile Thr Met Pro Asn Ser Lys Ala Gln
                180                 185                 190

Glu Ser Leu Ile Arg Lys Thr Tyr Lys Asn Ala Gly Leu Ser Thr Asn
            195                 200                 205

Asp Thr Gln Tyr Phe Glu
        210
```

<210> SEQ ID NO 77
<211> LENGTH: 690
<212> TYPE: DNA
<213> ORGANISM: Usnea florida

<400> SEQUENCE: 77

```
tattttattg gagacaacat acgaagcact tgaaaatagt gagtaagcca tgaccgtatt     60
aagtaaaagc tcacgaacag taaaggtggc acccctctgg ctagcattcg cggccaaaat   120
gtaggcgttt acgttggtgc atccatgtca gactacaacg agcttttcgc aaaggacccg   180
gataccaatt tgacatatcg tattaccgga actgcatcaa atattttgtc aaatcgactc   240
tcctacatgt tcgaccttca cgggccaagt ttcacggtgg acactgcgtg ctcatcaagc   300
ttggccgcat tccatctggc ctgtcagagt ttgaagacgg gagaggtccg gcaagccatc   360
gtgggcgggg cttaccttgt attatcccca gatcctacga tcggaatgag caaactcagg   420
```

```
cttacggcg aacatggtcg ctcatacact tacgatcacc gagggactgg atacggtcgt    480
ggcgagggcg tcgctagcct aattcttaag cctttacaag atgctatcga cgtgggtgat    540
acaattcgag caatcatacg taacactgga atgaatcaag acgggaagac gaacggaatt    600
acgctcccaa gcaaagacgc ccaagaaagc ctcataaggt ctgtctacac agctgcaggt    660
ctcgatccac tgtatacttc ctacgttgag                                     690
```

<210> SEQ ID NO 78
<211> LENGTH: 214
<212> TYPE: PRT
<213> ORGANISM: Usnea florida

<400> SEQUENCE: 78

```
Ile Leu Leu Glu Thr Thr Tyr Glu Ala Leu Glu Asn Ser Gly Thr Pro
 1               5                  10                  15

Leu Ala Ser Ile Arg Gly Gln Asn Val Gly Val Tyr Val Gly Ala Ser
            20                  25                  30

Met Ser Asp Tyr Asn Glu Leu Phe Ala Lys Asp Pro Asp Thr Asn Leu
        35                  40                  45

Thr Tyr Arg Ile Thr Gly Thr Ala Ser Asn Ile Leu Ser Asn Arg Leu
    50                  55                  60

Ser Tyr Met Phe Asp Leu His Gly Pro Ser Phe Thr Val Asp Thr Ala
65                  70                  75                  80

Cys Ser Ser Ser Leu Ala Ala Phe His Leu Ala Cys Gln Ser Leu Lys
                85                  90                  95

Thr Gly Glu Val Arg Gln Ala Ile Val Gly Gly Ala Tyr Leu Val Leu
            100                 105                 110

Ser Pro Asp Pro Thr Ile Gly Met Ser Lys Leu Arg Leu Tyr Gly Glu
        115                 120                 125

His Gly Arg Ser Tyr Thr Tyr Asp His Arg Gly Thr Gly Tyr Gly Arg
    130                 135                 140

Gly Glu Gly Val Ala Ser Leu Ile Leu Lys Pro Leu Gln Asp Ala Ile
145                 150                 155                 160

Asp Val Gly Asp Thr Ile Arg Ala Ile Ile Arg Asn Thr Gly Met Asn
                165                 170                 175

Gln Asp Gly Lys Thr Asn Gly Ile Thr Leu Pro Ser Lys Asp Ala Gln
            180                 185                 190

Glu Ser Leu Ile Arg Ser Val Tyr Thr Ala Ala Gly Leu Asp Pro Leu
        195                 200                 205

Tyr Thr Ser Tyr Val Glu
    210
```

<210> SEQ ID NO 79
<211> LENGTH: 761
<212> TYPE: DNA
<213> ORGANISM: Usnea florida

<400> SEQUENCE: 79

```
gcgaatgcta gagacggctt atcacgctct ggaggacggt aagtctaacc agtgcaaatt    60 tagggctat aatcttggtg tgtgagaata acataccatc agcgagcatc ccctggaga    120 agtgcttcgg ctcagacact tccgtttata ccgggtgctt caccaacgat tatctcagca    180
tactgcagca agactttgag gctgagcaaa ggcacgcagc catgggaatc gcgccctcca    240
tgttggccaa tcgcctaagc tggttcttca acttcaaggg gacatcgatg aacctggatt    300
```

```
cggcctgctc cagcagtctg gttgcactgc atcttgcttc acaggacctc cgtgctggta    360
ccacatcgat ggtatgtatc gatcataaaa tcacgtactc cttcattaat aaataaatgt    420
tttaggcact agttggaggg gcgaatcttg tctaccaccc cgacttcatg gagatgatgt    480
caaacttcaa cttcctgtct cccgacagcc gttcttggag tttcgatcaa cgtgctaatg    540
gttatgcgcg tggggaagga accgccgtga tggtcgtcaa acgccttgca gatgcactgc    600
gagatggaga tacaatcaga accgtaatct ggagtaccgg gtcgaaccaa gacgggagaa    660
cacctgggat cacgcagcca agtaaagaag cgcagttaaa tctcatcgag cgcacctaca    720
aacaagcgaa gattgatatg gagcctacca gattcttcga g                       761
```

<210> SEQ ID NO 80
<211> LENGTH: 214
<212> TYPE: PRT
<213> ORGANISM: Usnea florida

<400> SEQUENCE: 80

```
Arg Met Leu Glu Thr Ala Tyr His Ala Leu Glu Asp Ala Ser Ile Pro
  1               5                  10                  15

Leu Glu Lys Cys Phe Gly Ser Asp Thr Ser Val Tyr Thr Gly Cys Phe
                 20                  25                  30

Thr Asn Asp Tyr Leu Ser Ile Leu Gln Gln Asp Phe Glu Ala Glu Gln
             35                  40                  45

Arg His Ala Ala Met Gly Ile Ala Pro Ser Met Leu Ala Asn Arg Leu
         50                  55                  60

Ser Trp Phe Phe Asn Phe Lys Gly Thr Ser Met Asn Leu Asp Ser Ala
 65                  70                  75                  80

Cys Ser Ser Ser Leu Val Ala Leu His Leu Ala Ser Gln Asp Leu Arg
                 85                  90                  95

Ala Gly Thr Thr Ser Met Ala Leu Val Gly Gly Ala Asn Leu Val Tyr
            100                 105                 110

His Pro Asp Phe Met Glu Met Met Ser Asn Phe Asn Phe Leu Ser Pro
        115                 120                 125

Asp Ser Arg Ser Trp Ser Phe Asp Gln Arg Ala Asn Gly Tyr Ala Arg
    130                 135                 140

Gly Glu Gly Thr Ala Val Met Val Val Lys Arg Leu Ala Asp Ala Leu
145                 150                 155                 160

Arg Asp Gly Asp Thr Ile Arg Thr Val Ile Trp Ser Thr Gly Ser Asn
                165                 170                 175

Gln Asp Gly Arg Thr Pro Gly Ile Thr Gln Pro Ser Lys Glu Ala Gln
            180                 185                 190

Leu Asn Leu Ile Glu Arg Thr Tyr Lys Gln Ala Lys Ile Asp Met Glu
        195                 200                 205

Pro Thr Arg Phe Phe Glu
    210
```

<210> SEQ ID NO 81
<211> LENGTH: 1171
<212> TYPE: DNA
<213> ORGANISM: Artificial Sequence
<220> FEATURE:
<223> OTHER INFORMATION: Description of Artificial Sequence: Clone ps10

<400> SEQUENCE: 81

```
aaggagggc cgcccgggag aagaagttat cgtgggcgcc gattcggtcg accggcagca     60
attgcagcca gattgccgcg agggcttcct ccattcccgg cgcgggcgca acgaatccgg   120
```

```
tgtactccag atgccgtgcg gtccggggga gagctgcctg atccagtttg agattcttgt      180
ttaaaggaag ttcggccagc ttctctatgg cggcggggac catgtgagcg gggagcagag      240
ccttcatgtg ctggcgaatc gtttccgtgg acgctccgcc gactgcatac gccgcgagat      300
acttctcgcc ggggatatcg tctcggacca gcacaacgcc gtccgtgacg cccgggcacg      360
actgcagcgc ggcctgaatt tcgccgagtt ctatgcgatg cccgcgaagc ttgatctggc      420
cgtcgtttct gcccagaaaa tcgatgcgcc catccggcag atagcgcgcg cgatcgcccg      480
tgcggtacat acgcgcgccc ggaaatgggc taaacgggtt cggcacaaag taggctgcgg      540
tgagatcgct gcgccccgca tagccgcgcg cgacaccgtc tccggcagcg tacagccagc      600
cttccactcc cggcggaacg ggagcgaatt gctcgtcgag cacgtaggtt tggacgttcg      660
aaattggacg gccgatggga atcgacgggg tcccggcggg gaccgaatcg atgacgccac      720
acgccgtgag catcgtgttc tcggtagggc cgtaaccgtt caagaggcgg gcgggcttgc      780
cgtgctcgat caccatgcgc atccagtggg gatccagcgc ttcgccgccg acaatcacat      840
tggtcagcga ttcgaatccg gctggatctt cgcgggcaac ctgattgaac agagatgcag      900
taaggataat cgtgtccacg tggaagcggc gaaaggcgag aatcagctcg cggggcgcca      960
tcaaggtctc tttcgaaaga acgacgattc gcgcgccatg cagcaggccg ccccataact     1020
cgaaggtggg agggtcgaaa ccgaaggccg acatctgtcc cacggtatcg gcgggtgaga     1080
attgtacgta gttggtccgg ctaacgaggt tgacaatcgc cccgtggggg acggcgaccc     1140
ccttgggctt gccggtcgtg ccggacgtgt a                                    1171
```

<210> SEQ ID NO 82
<211> LENGTH: 390
<212> TYPE: PRT
<213> ORGANISM: Artificial Sequence
<220> FEATURE:
<223> OTHER INFORMATION: Description of Artificial Sequence: Clone ps10

<400> SEQUENCE: 82

```
Tyr Thr Ser Gly Thr Thr Gly Lys Pro Lys Gly Val Ala Val Pro His
 1               5                  10                  15

Gly Ala Ile Val Asn Leu Val Ser Arg Thr Asn Tyr Val Gln Phe Ser
                20                  25                  30

Pro Ala Asp Thr Val Gly Gln Met Ser Ala Phe Gly Phe Asp Pro Pro
            35                  40                  45

Thr Phe Glu Leu Trp Gly Gly Leu Leu His Gly Ala Arg Ile Val Val
        50                  55                  60

Leu Ser Lys Glu Thr Leu Met Ala Pro Arg Glu Leu Ile Leu Ala Phe
    65                  70                  75                  80

Arg Arg Phe His Val Asp Thr Ile Ile Leu Thr Ala Ser Leu Phe Asn
                    85                  90                  95

Gln Val Ala Arg Glu Asp Pro Ala Gly Phe Glu Ser Leu Thr Asn Val
                100                 105                 110

Ile Val Gly Gly Glu Ala Leu Asp Pro His Trp Met Arg Met Val Ile
            115                 120                 125

Glu His Gly Lys Pro Ala Arg Leu Leu Asn Gly Tyr Gly Pro Thr Glu
        130                 135                 140

Asn Thr Met Leu Thr Ala Cys Gly Val Ile Asp Ser Val Pro Ala Gly
    145                 150                 155                 160

Thr Pro Ser Ile Pro Ile Gly Arg Pro Ile Ser Asn Val Gln Thr Tyr
                    165                 170                 175
```

Val Leu Asp Glu Gln Phe Ala Pro Val Pro Gly Val Glu Gly Trp
        180                 185                 190

Leu Tyr Ala Ala Gly Asp Gly Val Ala Arg Gly Tyr Ala Gly Arg Ser
            195                 200                 205

Asp Leu Thr Ala Ala Tyr Phe Val Pro Asn Pro Phe Ser Pro Phe Pro
        210                 215                 220

Gly Ala Arg Met Tyr Arg Thr Gly Asp Arg Ala Arg Tyr Leu Pro Asp
225                 230                 235                 240

Gly Arg Ile Asp Phe Leu Gly Arg Asn Asp Gly Gln Ile Lys Leu Arg
                245                 250                 255

Gly His Arg Ile Glu Leu Gly Glu Ile Gln Ala Ala Leu Gln Ser Cys
            260                 265                 270

Pro Gly Val Thr Asp Gly Val Val Leu Val Arg Asp Asp Ile Pro Gly
        275                 280                 285

Glu Lys Tyr Leu Ala Ala Tyr Ala Val Gly Gly Ala Ser Thr Glu Thr
        290                 295                 300

Ile Arg Gln His Met Lys Ala Leu Leu Pro Ala His Met Val Pro Ala
305                 310                 315                 320

Ala Ile Glu Lys Leu Ala Glu Leu Pro Leu Asn Lys Asn Leu Lys Leu
                325                 330                 335

Asp Gln Ala Ala Leu Pro Arg Thr Ala Arg His Leu Glu Tyr Thr Gly
            340                 345                 350

Phe Val Ala Pro Ala Pro Gly Met Glu Glu Ala Leu Ala Ala Ile Trp
        355                 360                 365

Leu Gln Leu Leu Pro Val Asp Arg Ile Gly Ala His Asp Asn Phe Phe
    370                 375                 380

Ser Arg Ala Ala Pro Pro
385                 390

<210> SEQ ID NO 83
<211> LENGTH: 1222
<212> TYPE: DNA
<213> ORGANISM: Artificial Sequence
<220> FEATURE:
<223> OTHER INFORMATION: Description of Artificial Sequence: Clone ps7

<400> SEQUENCE: 83
cgtttcaccc caagaatctc agaccatata tcagcaatgg ccttctccct ggcattgccc      60
ggagcgacat agatcggatc ccgaatcaca gtatcgcgat caaatggcgg cagggcgttt    120
cggtcaatct tgccgttcgg cgttaaaggg agagaatcga caatgacgaa ggcgctgggc    180
accatgtagt ccggcagttt tgccttcaga tgggcgcgca attcgcttat tcgggagca     240 ccttcccgtg cgacgatata agcaactaat tgcttttctt cgctagggtc ttttgtcgtt    300
gtgaccacag cttctcgaat cggggatgtt gcgcaacagg acttcgattt ctccagctcg    360
atgcgatagc cgcgaatctt gacctgattg tcggtgcggc cgataaactc gatgttgcca    420
tccggcaaat aacgcgcaag atcgccagtt cgatagaggc gctgcgctgg ctcgcgatcg    480
aatgaatggt agatgaacct ctccgccgtc agttccggcc ggttgagata ccctcgcgcc    540
agtccgtcgc cgccaatgta gatctctcca accacgccga tcggcaccgg attgagatga    600
gcatccagta tgtagatctg cgtattcgcg atcggtcggc caatgggcgg taattctccc    660
cagcactctg gcggaccgtc cacagtaaac gctgtcacaa cgtggctttc cgtcggccca    720
tactggttga ccaaatgaca ctcgggcaac gtgtcaagga aacttctgat ccgcggcgtt    780

-continued

```
atctgcagcc gctctcccgc cgtaatgact tcgcgcagct gcggcaaaac cacattctcc    840
atgtgcgcgg cttccgccat ctgttgcagt acgacaaaag gcacaaaaag tctctctact    900
cgcttcattc gcaggaaatt caacagggct ggcggatcgc gtcggatttg cgcgggcagt    960
agcaccagtg tgcctcctga gcaccacgtg ctaaacatct cttgaaacga aacatcgaaa   1020
ctcaacgagg caaactgtaa cgttcgcgcc ggcaccgaac gagaaaaatc ctcaatttgc   1080
cacgcgatca ggttggcaag cgcgcggtgt tccatcacca caccettcgg cttgcccgtc   1140 gtgccaatcc cgcggccatg gcggccggga gcatgcgacg tcgggcccaa ttcgccctat   1200
agtgagtcgt attacaattc aa                                           1222
```

<210> SEQ ID NO 84
<211> LENGTH: 396
<212> TYPE: PRT
<213> ORGANISM: Artificial Sequence
<220> FEATURE:
<223> OTHER INFORMATION: Description of Artificial Sequence: Clone ps7

<400> SEQUENCE: 84

```
Gly Thr Thr Gly Lys Pro Lys Gly Val Val Met Glu His Arg Ala Leu
  1               5                  10                  15

Ala Asn Leu Ile Ala Trp Gln Ile Glu Asp Phe Ser Arg Ser Val Pro
             20                  25                  30

Ala Arg Thr Leu Gln Phe Ala Ser Leu Ser Phe Asp Val Ser Phe Gln
         35                  40                  45

Glu Met Phe Ser Thr Trp Cys Ser Gly Gly Thr Leu Val Leu Leu Pro
     50                  55                  60

Ala Gln Ile Arg Arg Asp Pro Ala Leu Leu Asn Phe Leu Arg Met
 65                  70                  75                  80

Lys Arg Val Glu Arg Leu Phe Val Pro Phe Val Val Leu Gln Gln Met
                 85                  90                  95

Ala Glu Ala Ala His Met Glu Asn Val Val Leu Pro Gln Leu Arg Glu
            100                 105                 110

Val Ile Thr Ala Gly Glu Arg Leu Gln Ile Thr Pro Arg Ile Arg Ser
        115                 120                 125

Phe Leu Asp Thr Leu Pro Glu Cys His Leu Val Asn Gln Tyr Gly Pro
    130                 135                 140

Thr Glu Ser His Val Val Thr Ala Phe Thr Val Asp Gly Pro Pro Glu
145                 150                 155                 160

Cys Trp Gly Glu Leu Pro Pro Ile Gly Arg Pro Ile Ala Asn Thr Gln
                165                 170                 175

Ile Tyr Ile Leu Asp Ala His Leu Asn Pro Val Pro Ile Gly Val Val
            180                 185                 190

Gly Glu Ile Tyr Ile Gly Gly Asp Gly Leu Ala Arg Gly Tyr Leu Asn
        195                 200                 205

Arg Pro Glu Leu Thr Ala Glu Arg Phe Ile Tyr His Ser Phe Asp Arg
    210                 215                 220

Glu Pro Ala Gln Arg Leu Tyr Arg Thr Gly Asp Leu Ala Arg Tyr Leu
225                 230                 235                 240

Pro Asp Gly Asn Ile Glu Phe Ile Gly Arg Thr Asp Asn Gln Val Lys
                245                 250                 255

Ile Arg Gly Tyr Arg Ile Glu Leu Glu Lys Ser Lys Ser Cys Cys Ala
            260                 265                 270

Thr Ser Pro Ile Arg Glu Ala Val Val Thr Thr Lys Asp Pro Ser
        275                 280                 285
```

```
Glu Glu Lys Gln Leu Val Ala Tyr Ile Val Ala Arg Glu Gly Ala Pro
        290                 295                 300
Glu Ile Ser Glu Leu Arg Ala His Leu Lys Ala Lys Leu Pro Asp Tyr
305                 310                 315                 320
Met Val Pro Ser Ala Phe Val Ile Val Asp Ser Leu Pro Leu Thr Pro
                325                 330                 335
Asn Gly Lys Ile Asp Arg Asn Ala Leu Pro Pro Phe Asp Arg Asp Thr
                340                 345                 350
Val Ile Arg Asp Pro Ile Tyr Val Ala Pro Gly Asn Ala Arg Glu Lys
            355                 360                 365
Ala Ile Ala Asp Ile Trp Ser Glu Ile Leu Gly Val Lys Arg Ile Gly
        370                 375                 380
Val His Asp Asn Phe Phe Ala Pro Gly Gly Pro Ser
385                 390                 395
```

<210> SEQ ID NO 85
<211> LENGTH: 1200
<212> TYPE: DNA
<213> ORGANISM: Artificial Sequence
<220> FEATURE:
<223> OTHER INFORMATION: Description of Artificial Sequence: Clone ps30

<400> SEQUENCE: 85

| | | |
|---|---|---|
| aatctacacg tccggcacca ccggcaagcc caaggggggcc ataatccatc acctgggact | 60 |
| ggcgaattac ttggtgtggt gctcgcgggc ttacgcgatt gctcaaggag tgggagcacc | 120 |
| ggtccactcg tcgatctcgt tcgatctgac gatcactgcc ttgcttgccc ccttggtcgt | 180 |
| cggccggcgc atcgacctgc ttgatgaaga actgggcatc gagcaactga gttacgctct | 240 |
| ccggcgatcg cgcgactata gcctggtcaa gatcactccg gctcacctgc gctggctcgg | 300 |
| cgatgaactg ggaccctgcg aggccgaagg tcgtacgcga gctttcatca tcggtggtga | 360 |
| gcaactgacg gccgaacacg tckcattctg gaggcggcac gcgccgggga cgagcctgat | 420 |
| caacgagtat ggtccgaccg agacggtcgt cggctgctgc gtgtaccgcg tgcctcctga | 480 |
| ccaggagatt tcggggccca tcccgattgg ccgaccgatc gccaacacgc gtctctacgt | 540 |
| cctcgatccg gatctcgcgc tggtacccat cggcgttgca ggcgagctgt acatcggcgg | 600 |
| tgccggggtc gcgcgggggt atctcaacag gcccggcctg accgctgaaa ggttcatccc | 660 |
| cgacccgttc ggcaagaagc cggcgagcg cctctatcgc accggagacc tcgcccgatg | 720 |
| gcggtccgac ggtaacctcg agtatctcgg cagggtcgat cgccaggtta agtccgcgg | 780 |
| gtttcggatc gaacccgggg agatcgaaca ggcactcgcc cggcactccg cggtacgcga | 840 |
| gtccgtcgtg gtcgcaagcg caggtgcatc ggacgtgcaa cgcctcgtcg cctatctggt | 900 |
| tcttgcggag gcagggccgg caccgcccga ctcggagctg cgcgagttcc tgcggacgtt | 960 |
| actccccgag ccgatgatac cctcggcatt cgttgtgctg gagacgctcc cactgaccca | 1020 |
| caacgggaag gtggaccgag aggccctgcc ggcccctgag ggtgtgccct tccgtgggga | 1080 |
| tgctcgtttc gttgctcccc gcggcccgct cgaacaggag gtggcatcga tctggggtgc | 1140 |
| agtcctcgga ctggagcgta tcggcgccct tgacaacttc ttcttccctc ggcggcccct | 1200 |

<210> SEQ ID NO 86
<211> LENGTH: 399
<212> TYPE: PRT
<213> ORGANISM: Artificial Sequence
<220> FEATURE:
<223> OTHER INFORMATION: Description of Artificial Sequence: Clone ps30

-continued

```
<221> NAME/KEY: SITE
<222> LOCATION: (128)
<223> OTHER INFORMATION: Xaa=unknown amino acid

<400> SEQUENCE: 86

Ile Tyr Thr Ser Gly Thr Gly Lys Pro Lys Gly Ala Ile Ile His
  1               5                  10                  15

His Leu Gly Leu Ala Asn Tyr Leu Val Trp Cys Ser Arg Ala Tyr Ala
             20                  25                  30

Ile Ala Gln Gly Val Gly Ala Pro Val His Ser Ser Ile Ser Phe Asp
         35                  40                  45

Leu Thr Ile Thr Ala Leu Leu Ala Pro Leu Val Val Gly Arg Arg Ile
     50                  55                  60

Asp Leu Leu Asp Glu Glu Leu Gly Ile Glu Gln Leu Ser Tyr Ala Leu
 65                  70                  75                  80

Arg Arg Ser Arg Asp Tyr Ser Leu Val Lys Ile Thr Pro Ala His Leu
                 85                  90                  95

Arg Trp Leu Gly Asp Glu Leu Gly Pro Cys Glu Ala Glu Gly Arg Thr
            100                 105                 110

Arg Ala Phe Ile Ile Gly Gly Glu Gln Leu Thr Ala Glu His Val Xaa
        115                 120                 125

Phe Trp Arg Arg His Ala Pro Gly Thr Ser Leu Ile Asn Glu Tyr Gly
    130                 135                 140

Pro Thr Glu Thr Val Val Gly Cys Cys Val Tyr Arg Val Pro Pro Asp
145                 150                 155                 160

Gln Glu Ile Ser Gly Pro Ile Pro Ile Gly Arg Pro Ile Ala Asn Thr
                165                 170                 175

Arg Leu Tyr Val Leu Asp Pro Asp Leu Ala Leu Val Pro Ile Gly Val
            180                 185                 190

Ala Gly Glu Leu Tyr Ile Gly Gly Ala Gly Val Ala Arg Gly Tyr Leu
        195                 200                 205

Asn Arg Pro Gly Leu Thr Ala Glu Arg Phe Ile Pro Asp Pro Phe Gly
    210                 215                 220

Lys Lys Pro Gly Glu Arg Leu Tyr Arg Thr Gly Asp Leu Ala Arg Trp
225                 230                 235                 240

Arg Ser Asp Gly Asn Leu Glu Tyr Leu Gly Arg Val Asp Arg Gln Val
                245                 250                 255

Lys Val Arg Gly Phe Arg Ile Glu Pro Gly Glu Ile Glu Gln Ala Leu
            260                 265                 270

Ala Arg His Ser Ala Val Arg Glu Ser Val Val Ala Ser Ala Gly
        275                 280                 285

Ala Ser Asp Val Gln Arg Leu Val Ala Tyr Leu Val Leu Ala Glu Ala
    290                 295                 300

Gly Pro Ala Pro Pro Asp Ser Glu Leu Arg Glu Phe Leu Arg Thr Leu
305                 310                 315                 320

Leu Pro Glu Pro Met Ile Pro Ser Ala Phe Val Val Leu Glu Thr Leu
                325                 330                 335

Pro Leu Thr His Asn Gly Lys Val Asp Arg Glu Ala Leu Pro Ala Pro
            340                 345                 350

Glu Gly Val Pro Phe Arg Gly Asp Ala Arg Phe Val Ala Pro Arg Gly
        355                 360                 365

Pro Leu Glu Gln Glu Val Ala Ser Ile Trp Gly Ala Val Leu Gly Leu
    370                 375                 380
```

Glu Arg Ile Gly Ala Leu Asp Asn Phe Phe Phe Pro Arg Arg Pro
385                 390                 395

<210> SEQ ID NO 87
<211> LENGTH: 1204
<212> TYPE: DNA
<213> ORGANISM: Artificial Sequence
<220> FEATURE:
<223> OTHER INFORMATION: Description of Artificial Sequence: Clone ps2

<400> SEQUENCE: 87

| | | | | | |
|---|---|---|---|---|---|
| aggggccgcc | gggcgagaag | aagttcgcgg | tgatgctcac | cggcgcgtcg | agcttcaacg | 60 |
| cctcctgcca | gatctccgcg | agcttgctct | ccgtctccgt | gcccggcgct | acgtattggg | 120 |
| cgccggcgct | acggtcgatg | gacggcagcg | ccttacgatc | gatcttgccg | ttggcattca | 180 |
| gcggaaaggc | ctccaggacg | cgccagccgc | tgggaatcat | gtactcgggc | agggccagct | 240 |
| tgaggcgcat | ccgcagcgcc | gagatgagca | cctcttcgtc | cgcggtctgg | gccacgacgt | 300 |
| aggcgacgag | ggccttgttc | tccccctctc | cctgcgccac | gaccagggcg | tcgtcgacgc | 360 |
| cagcctcggt | cttcagcgcg | gtctcgatct | cgccgagctc | gatgcggaag | ccgcggatct | 420 |
| tgatctggtc | gtcgaggcgg | ccgaggaact | cgagatcgcc | gctggcgagc | cggcgaacga | 480 |
| ggtcgccgct | gcgatagagg | cgcccttcgc | cgaagggatt | ggcgatgaac | ttcgccgccg | 540 |
| tcagctccgg | ctggttgacg | tagcctctgg | ccaccctgc | cccgccaatg | cacagctcgc | 600 |
| cggccacgcc | gaccggcgcg | atctccagtg | cctcgttgag | gacatacagc | tccgtgttgt | 660 |
| ccatggccct | gccgatgggc | aggcgctccg | gcaggccggc | ctggagagcg | gcggtgacgt | 720 |
| cgaacatggc | gcagccgacc | acggtctccg | tgggaccgta | gtggttgtag | atctgggcgt | 780 |
| ggggaagcg | cgtttgcagc | tcgcgggcga | gcgaggcggg | aaacgattcg | ccgccgatga | 840 |
| cgaaaacgtg | ttgagatgaa | gcccgggccg | tgtcttccgt | cagctccgcg | ctgtcgagca | 900 |
| gagcgagcat | accggtgaga | tgcatcggcg | tcatgcgcag | cagataagcc | cgttcgtcgc | 960 |
| cggccaacgc | tttcgcgagc | tcgttcaact | catcgccggg | cgtggtcagc | gagacgcagc | 1020 |
| caccccggag | caagggaaca | tacaggctgg | gcacggtgat | gtcgaagccg | tgggaggtga | 1080 |
| cgacgaggga | gccggccaac | cccttcgcgt | agtagcgctg | cgaagcgaag | gcgcagtagt | 1140 |
| cactgaggcc | ggcgtgtctg | atctccacgc | ccttcggctt | gcccgtcgtg | ccggacgtgt | 1200 |
| agat | | | | | | 1204 |

<210> SEQ ID NO 88
<211> LENGTH: 401
<212> TYPE: PRT
<213> ORGANISM: Artificial Sequence
<220> FEATURE:
<223> OTHER INFORMATION: Description of Artificial Sequence: Clone ps2

<400> SEQUENCE: 88

Ile Tyr Thr Ser Gly Thr Thr Gly Lys Pro Lys Gly Val Glu Ile Arg
1               5                   10                  15

His Ala Gly Leu Ser Asp Tyr Cys Ala Phe Ala Ser Gln Arg Tyr Tyr
            20                  25                  30

Ala Lys Gly Leu Ala Gly Ser Leu Val Val Thr Ser His Gly Phe Asp
        35                  40                  45

Ile Thr Val Pro Ser Leu Tyr Val Pro Leu Leu Arg Gly Gly Cys Val
    50                  55                  60

Ser Leu Thr Thr Pro Gly Asp Glu Leu Asn Glu Leu Ala Lys Ala Leu
65                  70                  75                  80

```
Ala Gly Asp Glu Arg Ala Tyr Leu Leu Arg Met Thr Pro Met His Leu
             85                  90                  95

Thr Gly Met Leu Ala Leu Leu Asp Ser Ala Glu Leu Thr Glu Asp Thr
        100                 105                 110

Ala Arg Ala Ser Ser Gln His Val Phe Val Ile Gly Gly Glu Ser Phe
        115                 120                 125

Pro Ala Ser Leu Ala Arg Glu Leu Gln Thr Arg Phe Pro His Ala Gln
    130                 135                 140

Ile Tyr Asn His Tyr Gly Pro Thr Glu Thr Val Val Gly Cys Ala Met
145                 150                 155                 160

Phe Asp Val Thr Ala Ala Leu Gln Ala Gly Leu Pro Glu Arg Leu Pro
                165                 170                 175

Ile Gly Arg Ala Met Asp Asn Thr Glu Leu Tyr Val Leu Asn Glu Ala
            180                 185                 190

Leu Glu Ile Ala Pro Val Gly Val Ala Gly Glu Leu Cys Ile Gly Gly
        195                 200                 205

Ala Gly Val Ala Arg Gly Tyr Val Asn Gln Pro Glu Leu Thr Ala Ala
    210                 215                 220

Lys Phe Ile Ala Asn Pro Phe Gly Glu Gly Arg Leu Tyr Arg Ser Gly
225                 230                 235                 240

Asp Leu Val Arg Arg Leu Ala Ser Gly Asp Leu Glu Phe Leu Gly Arg
                245                 250                 255

Leu Asp Asp Gln Ile Lys Ile Arg Gly Phe Arg Ile Glu Leu Gly Glu
            260                 265                 270

Ile Glu Thr Ala Leu Lys Thr Glu Ala Gly Val Asp Asp Ala Leu Val
        275                 280                 285

Val Ala Gln Gly Glu Gly Glu Asn Lys Ala Leu Val Ala Tyr Val Val
    290                 295                 300

Ala Gln Thr Ala Asp Glu Val Leu Ile Ser Ala Leu Arg Met Arg
305                 310                 315                 320

Leu Lys Leu Ala Leu Pro Glu Tyr Met Ile Pro Ser Gly Trp Arg Val
                325                 330                 335

Leu Glu Ala Phe Pro Leu Asn Ala Asn Gly Lys Ile Asp Arg Lys Ala
            340                 345                 350

Leu Pro Ser Ile Asp Arg Ser Ala Gly Ala Gln Tyr Val Ala Pro Gly
        355                 360                 365

Thr Glu Thr Glu Ser Lys Leu Ala Glu Ile Trp Gln Glu Ala Leu Lys
    370                 375                 380

Leu Asp Ala Pro Val Ser Ile Thr Ala Asn Phe Phe Ser Pro Gly Gly
385                 390                 395                 400

Pro

<210> SEQ ID NO 89
<211> LENGTH: 1190
<212> TYPE: DNA
<213> ORGANISM: Artificial Sequence
<220> FEATURE:
<223> OTHER INFORMATION: Description of Artificial Sequence: Clone ps24

<400> SEQUENCE: 89
atctacacct cgggcacgac cggcaagccg aagggatca tgtattcgca tcgatacctg      60
ttgcataata tgcgcaacta cggcgactta tttcaggtct cccccacga tcgctggagt    120 tggttgcatt cctacagcta tgcttcggcg aatactgata tcctttgccc gctactgcac    180
```

-continued

```
ggcgccgccg tctgcccttg gaatttgcat cgtaatggcc tatcgggctt agctcgttgg      240
ctcgccgagt cgcgaatcac cattttgaac tggatgccga caccgctacg cagtttggca      300
aagctctggc cgccaaagca cgtgcttccc gatctgcgac ttacagtgtt gggcggcgaa      360
acgctgtttg cccaagacgt tgctgacttt cggcgaataa tttcgctgaa ttgcctaatc      420
gccaatcgtc tgggaacttc ggaaactgga ttgtttcggc tcgcgtttct cgaccgagag      480
actccccttg ctaatggttc catacaggcc ggatacgaag ttccagacaa gaccgtcgtc      540
ctgttcgacg aatatggagt tgagctggcc cctggcaacg tcggtcagat tggcgtgcgc      600
agcaggtact tgccgcctgg atactggcga cggccggagt tgacaagcga gcgatttcta      660
accagtaaag gcgatgatga cgtacggacc ttcctcaccg gcgaccttgg gcgaatgcgg      720
gacgacggat gcctcgagca ctgcggacgg ctcgactccc aagtgaagat ccgtggtcac      780
cgcatcgcaa tgggagagat cgaattcttg cttcggacat gcgacggagt cagcgaagca      840
gttgtcattg ccaggccaca ttcagacggt gaaacccgtt tgatagctta ttttgtgccg      900
accgagaaaa gcgctatcga tgtatcgagc cttcgtcggc acctgctggg aaagctgcct      960
ggccacatga tcccctcggc gtttgtgcgg ctcgacggcg tgcccaaaaa cgccaaccaa     1020
aaagtagatt gggcggcctt gccagcaccg aacttccaaa accagggaca gcagcacgta     1080
ccgccacaaa cgccttggca gcgacatctc gtggagttgt ggcaaaagtt gttgaatgtg     1140
gaatcgatcg gcatccacga tgacttcttc gccctcggcg ccccctcctt                1190
```

```
<210> SEQ ID NO 90
<211> LENGTH: 396
<212> TYPE: PRT
<213> ORGANISM: Artificial Sequence
<220> FEATURE:
<223> OTHER INFORMATION: Description of Artificial Sequence: Clone ps24

<400> SEQUENCE: 90
```

Ile Tyr Thr Ser Gly Thr Thr Gly Lys Pro Lys Gly Ile Met Tyr Ser
 1               5                  10                  15

His Arg Tyr Leu Leu His Asn Met Arg Asn Tyr Gly Asp Leu Phe Gln
            20                  25                  30

Val Ser Pro His Asp Arg Trp Ser Trp Leu His Ser Tyr Ser Tyr Ala
        35                  40                  45

Ser Ala Asn Thr Asp Ile Leu Cys Pro Leu Leu His Gly Ala Ala Val
    50                  55                  60

Cys Pro Trp Asn Leu His Arg Asn Gly Leu Ser Gly Leu Ala Arg Trp
65                  70                  75                  80

Leu Ala Glu Ser Arg Ile Thr Ile Leu Asn Trp Met Pro Thr Pro Leu
                85                  90                  95

Arg Ser Leu Ala Lys Leu Trp Pro Pro Lys His Val Leu Pro Asp Leu
            100                 105                 110

Arg Leu Thr Val Leu Gly Gly Glu Thr Leu Phe Ala Gln Asp Val Ala
        115                 120                 125

Asp Phe Arg Arg Ile Ile Ser Leu Asn Cys Leu Ile Ala Asn Arg Leu
    130                 135                 140

Gly Thr Ser Glu Thr Gly Leu Phe Arg Leu Ala Phe Leu Asp Arg Glu
145                 150                 155                 160

Thr Pro Leu Ala Asn Gly Ser Ile Gln Ala Gly Tyr Glu Val Pro Asp
                165                 170                 175

Lys Thr Val Val Leu Phe Asp Glu Tyr Gly Val Glu Leu Ala Pro Gly
            180                 185                 190

```
Asn Val Gly Gln Ile Gly Val Arg Ser Arg Tyr Leu Pro Pro Gly Tyr
            195                 200                 205

Trp Arg Arg Pro Glu Leu Thr Ser Glu Arg Phe Leu Thr Ser Lys Gly
        210                 215                 220

Asp Asp Asp Val Arg Thr Phe Leu Thr Gly Asp Leu Gly Arg Met Arg
225                 230                 235                 240

Asp Asp Gly Cys Leu Glu His Cys Gly Arg Leu Asp Ser Gln Val Lys
                245                 250                 255

Ile Arg Gly His Arg Ile Ala Met Gly Glu Ile Glu Phe Leu Leu Arg
                260                 265                 270

Thr Cys Asp Gly Val Ser Glu Ala Val Val Ile Ala Arg Pro His Ser
            275                 280                 285

Asp Gly Glu Thr Arg Leu Ile Ala Tyr Phe Val Pro Thr Glu Lys Ser
        290                 295                 300

Ala Ile Asp Val Ser Ser Leu Arg Arg His Leu Gly Lys Leu Pro
305                 310                 315                 320

Gly His Met Ile Pro Ser Ala Phe Val Arg Leu Asp Gly Val Pro Lys
                325                 330                 335

Asn Ala Asn Gln Lys Val Asp Trp Ala Ala Leu Pro Ala Pro Asn Phe
            340                 345                 350

Gln Asn Gln Gly Gln Gln His Val Pro Pro Gln Thr Pro Trp Gln Arg
        355                 360                 365

His Leu Val Glu Leu Trp Gln Lys Leu Leu Asn Val Glu Ser Ile Gly
            370                 375                 380

Ile His Asp Asp Phe Phe Ala Leu Gly Gly Pro Ser
385                 390                 395

<210> SEQ ID NO 91
<211> LENGTH: 1178
<212> TYPE: DNA
<213> ORGANISM: Artificial Sequence
<220> FEATURE:
<223> OTHER INFORMATION: Description of Artificial Sequence: Clone ps25

<400> SEQUENCE: 91
aaggaggggc cgcccggcgc gaagaagttc tcgtgtagcc cgacgcgttc cagctgcagc      60
acggcgcacc agatcgctgc gacctgccgc tggacgtccg tcatgatcgc ggtgtccgct     120
gcggccgctg ccgcgcgatt cacctgtgga atgggcaggg ccttgcggtc gatcttgtcg     180
ttcggcgtga gcggcagcgc ggcgagcgat acgatcacct gtggcaccat gtactcgggg     240
agtctcgcgc ggagcgccgt ccggagctcg tcgagcggca gcacgccgtc ttctgccggg     300
acgacgtacg ccaccagacg ctgatcgccg ggggtgtcct cgcgcacgac ggccacgctg     360
cggcgcaccg acgatgctc ggacaggacc gattcgatct cccccagctc gatcggtag      420
ccgcgaagct tcacctgatg atctcggcgt ccgacgaact cgagggcccg atcggcgcgc     480
agtcgtacga tgtcgccggt gcggtacacg cgctccgccg gtctgcccgc gacctcgacg     540
acgacgaact tttctgccgt gagctcgggt cgatgacgat agccccgcgc cacgccctct     600
cctccgatgc acagctcacc cggcacgccg atgggagcct ggcgacccgc ggcgtcgagc     660
acgtagacgt tcgtgttggc gatgggatgg ccgatcggaa tatcgcgatc gcaatccgtg     720
acctgatgca cggtcgacca gatcgtcgtc tcggtcgggc cgtacatgtt ccacagcgcc     780
cgcaccctcg acgagagatc gcgcgcgaga tcgcgtggaa gggcctcccc gccgcagagc     840
gcggtgagat ccgtcttgcc ctgccagccg gcgtcgatga gcaggcgcca ggtcgcgggg     900
```

-continued

```
gtcgcctgca tcatcgtcgc tctgcacgat tcgatgcgct cgcgaagacg ctcgccgtcg      960
agcacgtcgc cgcgggaggc gatgaccgtc ctcccgccga cgacgagagg caagaacagc     1020
tcgagacccg cgatgtcgaa cgacggcgtg gtgaccgcga ggagcacgtc gccggctcgc     1080
aagcctggct ccttctgcat ggcgcgcagg aaattcacga gctggcggtg ctcgatctcg     1140 accccttcg gcttgcccgt cgtgcccgac gtgtagat                              1178
```

<210> SEQ ID NO 92
<211> LENGTH: 392
<212> TYPE: PRT
<213> ORGANISM: Artificial Sequence
<220> FEATURE:
<223> OTHER INFORMATION: Description of Artificial Sequence: Clone ps25

<400> SEQUENCE: 92

```
Ile Tyr Thr Ser Gly Thr Thr Gly Lys Pro Lys Gly Val Glu Ile Glu
  1               5                  10                  15

His Arg Gln Leu Val Asn Phe Leu Arg Ala Met Gln Lys Glu Pro Gly
                 20                  25                  30

Leu Arg Ala Gly Asp Val Leu Leu Ala Val Thr Thr Pro Ser Phe Asp
             35                  40                  45

Ile Ala Gly Leu Glu Leu Phe Leu Pro Leu Val Gly Gly Arg Thr
         50                  55                  60

Val Ile Ala Ser Arg Gly Asp Val Leu Asp Gly Glu Arg Leu Arg Glu
 65                  70                  75                  80

Arg Ile Glu Ser Cys Arg Ala Thr Met Met Gln Ala Thr Pro Ala Thr
                 85                  90                  95

Trp Arg Leu Leu Ile Asp Ala Gly Trp Gln Gly Lys Thr Asp Leu Thr
            100                 105                 110

Ala Leu Cys Gly Gly Glu Ala Leu Pro Arg Asp Leu Ala Arg Asp Leu
        115                 120                 125

Ser Ser Arg Val Arg Ala Leu Trp Asn Met Tyr Gly Pro Thr Glu Thr
    130                 135                 140

Thr Ile Trp Ser Thr Val His Gln Val Thr Asp Cys Asp Arg Asp Ile
145                 150                 155                 160

Pro Ile Gly His Pro Ile Ala Asn Thr Asn Val Tyr Val Leu Asp Ala
                165                 170                 175

Ala Gly Arg Gln Ala Pro Ile Gly Val Pro Gly Glu Leu Cys Ile Gly
            180                 185                 190

Gly Glu Gly Val Ala Arg Gly Tyr Arg His Arg Pro Glu Leu Thr Ala
        195                 200                 205

Glu Lys Phe Val Val Val Glu Val Ala Gly Arg Pro Ala Glu Arg Val
    210                 215                 220

Tyr Arg Thr Gly Asp Ile Val Arg Leu Arg Ala Asp Arg Ala Leu Glu
225                 230                 235                 240

Phe Val Gly Arg Arg Asp His Gln Val Lys Leu Arg Gly Tyr Arg Ile
                245                 250                 255

Glu Leu Gly Glu Ile Glu Ser Val Leu Ser Glu His Pro Ser Val Arg
            260                 265                 270

Arg Ser Val Ala Val Val Arg Glu Asp Thr Pro Gly Asp Gln Arg Leu
        275                 280                 285

Val Ala Tyr Val Val Pro Ala Glu Asp Gly Val Leu Pro Leu Asp Glu
    290                 295                 300
```

```
Leu Arg Thr Ala Leu Arg Ala Arg Leu Pro Glu Tyr Met Val Pro Gln
305                 310                 315                 320

Val Ile Val Ser Leu Ala Ala Leu Pro Leu Thr Pro Asn Asp Lys Ile
            325                 330                 335

Asp Arg Lys Ala Leu Pro Ile Pro Gln Val Asn Arg Ala Ala Ala Ala
        340                 345                 350

Ala Ala Asp Thr Ala Ile Met Thr Asp Val Gln Arg Gln Val Ala Ala
        355                 360                 365

Ile Trp Cys Ala Val Leu Gln Leu Glu Arg Val Gly Leu His Glu Asn
    370                 375                 380

Phe Phe Ala Pro Gly Gly Pro Ser
385                 390

<210> SEQ ID NO 93
<211> LENGTH: 1178
<212> TYPE: DNA
<213> ORGANISM: Artificial Sequence
<220> FEATURE:
<223> OTHER INFORMATION: Description of Artificial Sequence: Clone ps3

<400> SEQUENCE: 93
atctacacct ccggcacgac gggcaagccg aagggagtaa agatcacaca tcgtgccgtg      60
gtgaattttc tgaactcgat gcggcgtgaa ccagggctga ccccggacga tgtggtgctc     120
tcggtcacca cgctgtcgtt tgacattgcc ggactcgaac tccacctgcc cctgacgact     180
ggagccacgg tcgtagtggc gacccaagac gcggtgtccg acgctgaact gctggtcaga     240
gagttggagc ggaccggaac aactctgttg caggcgacgc cagtcacatg gcgaatgctt     300
ctggagtcgg gctggaaagg aaatccgcga ctcaaggctc tggtcggagg tgaggcagtg     360
ccgagggacc tggtgaatcg gcttgctccc ctttgcgcgt cactttggaa catgtacgga     420
ccaacggaaa ccacgatctg gtcaacggtt gggcgtctgg aggctggaga tggtgtgtct     480
agtattggcc ggcccatcga caatacgcgg atttacgtcg tggatccgtc gatacacctt     540
cagcccatcg gagttcccgg cgaattgctg attggcggag aaggattggc cgacggatat     600
ctgaaacgcg atcagttgac ggcagagaag ttcattcctg atccatttgg tgggaggcct     660
gggtctcggc tgtatcgaac cggagatctt gcgcgctggc gcgcggacgg caccttggag     720
tgtctcggac gaatggacca acaggtgaag attcggggtt cccggatcga attgggtgag     780
atcgaaaccc tgttggcctc ccacccggat gtgaaacaga acgtggtggt cgtacgcgag     840
gacagccccg gggaaaaaaa attggtgggc tatttcgtgc cggcgaacgg acgcaatccc     900
gaagtgatgg aatttcgcaa acatctgcag cggacgcttc cggattacat ggtcccctca     960
gtgtacgtgc ccttgacctc ggttccgctt acacccaacg gaaagatcga ccgcaaggcg    1020
ctgcccgcac cggatatcag cgccgtcacg gtttcccgag agtcaattgc gccgcgcaat    1080
cccgccgaag agcggctggc agcaattttc gccaaggtgc ttggcacgcc gatcgcctcg    1140
atccacgaca gcttcttctc cccgggcggc ccctccat                            1178

<210> SEQ ID NO 94
<211> LENGTH: 388
<212> TYPE: PRT
<213> ORGANISM: Artificial Sequence
<220> FEATURE:
<223> OTHER INFORMATION: Description of Artificial Sequence: Clone ps3

<400> SEQUENCE: 94
```

-continued

```
Ile Tyr Thr Ser Gly Thr Thr Gly Lys Pro Lys Gly Val Lys Ile Thr
 1               5                  10                  15

His Arg Ala Val Val Asn Phe Leu Asn Ser Met Arg Arg Glu Pro Gly
             20                  25                  30

Leu Thr Pro Asp Asp Val Val Leu Ser Val Thr Thr Leu Ser Phe Asp
         35                  40                  45

Ile Ala Gly Leu Glu Leu His Leu Pro Leu Thr Thr Gly Ala Thr Val
 50                  55                  60

Val Val Ala Thr Gln Asp Ala Val Ser Asp Ala Glu Leu Leu Val Arg
 65                  70                  75                  80

Glu Leu Glu Arg Thr Gly Thr Thr Leu Leu Gln Ala Thr Pro Val Thr
                 85                  90                  95

Trp Arg Met Leu Leu Glu Ser Gly Trp Lys Gly Asn Pro Arg Leu Lys
                100                 105                 110

Ala Leu Val Gly Gly Glu Ala Val Pro Arg Asp Leu Val Asn Arg Leu
            115                 120                 125

Ala Pro Leu Cys Ala Ser Leu Trp Asn Met Tyr Gly Pro Thr Glu Thr
130                 135                 140

Thr Ile Trp Ser Thr Val Gly Arg Leu Glu Ala Gly Asp Gly Val Ser
145                 150                 155                 160

Ser Ile Gly Arg Pro Ile Asp Asn Thr Arg Ile Tyr Val Val Asp Pro
                165                 170                 175

Ser Ile His Leu Gln Pro Ile Gly Val Pro Gly Glu Leu Leu Ile Gly
                180                 185                 190

Gly Glu Gly Leu Ala Asp Gly Tyr Leu Lys Arg Asp Gln Leu Thr Ala
            195                 200                 205

Glu Lys Phe Ile Pro Asp Pro Phe Gly Gly Arg Pro Gly Ser Arg Leu
210                 215                 220

Tyr Thr Gly Asp Leu Ala Arg Trp Arg Ala Asp Gly Thr Leu Glu Cys
225                 230                 235                 240

Leu Gly Arg Met Asp Gln Gln Val Lys Ile Arg Gly Ser Arg Glu Leu
                245                 250                 255

Gly Glu Ile Glu Thr Leu Leu Ala Ser His Pro Asp Lys Gln Asn Val
            260                 265                 270

Val Val Arg Glu Asp Ser Pro Gly Glu Lys Lys Leu Val Gly Tyr
                275                 280                 285

Phe Val Pro Ala Asn Gly Arg Asn Pro Glu Val Met Glu Phe Arg Lys
290                 295                 300

His Leu Gln Arg Thr Leu Pro Asp Tyr Met Val Pro Ser Val Tyr Val
305                 310                 315                 320

Pro Leu Thr Ser Val Pro Leu Thr Pro Asn Gly Lys Ile Asp Arg Lys
                325                 330                 335

Ala Leu Pro Ala Pro Asp Ile Ser Ala Val Thr Val Ser Arg Glu Ser
            340                 345                 350

Ile Ala Pro Arg Asn Pro Ala Glu Glu Arg Leu Ala Ala Ile Phe Ala
                355                 360                 365

Lys Val Leu Gly Thr Pro Ile Ala Ser Ile His Asp Ser Phe Phe Ser
        370                 375                 380

Pro Gly Gly Pro
385
```

METHOD FOR ISOLATION OF BIOSYNTHESIS GENES FOR BIOACTIVE MOLECULES

BACKGROUND OF THE INVENTION

This application relates to a method for the isolation of biosynthesis genes for antibiotics and other bioactive molecules from complex natural sources such as humus, soil and lichens.

Antibiotics play an important role in man's efforts to combat disease and other economically detrimental effects of microorganisms. Traditionally, antibiotics have been identified by screening microorganisms, especially those found naturally in soil, for their ability to produce an antimicrobial substance. In some cases, the gene or genes responsible for antibiotic synthesis have then been identified and cloned into producer organisms which produce the antibiotic in an unregulated manner for commercial applications. However, it has been estimated that less than 1% of the microorganisms present in soil are culturable. Torsvik et al., *Appl. Environ. Microbiol.* 56: 782–787 (1990). Thus, much of the genetic diversity potentially available in soil microorganisms is unavailable through traditional techniques.

As pathogenic microorganisms become increasingly resistant to known antibiotics, it would, however, be highly desirable to be able to access the reservoir of genetic diversity found in soil, and to facilitate the exploration of new species of antibiotics which may be made by the vast numbers of unculturable organisms found there. It would further be desirable to have access to novel biosynthetic enzymes and the genes encoding such enzymes, which could be used in recombinant organisms for antibiotic production or for in vitro enzymatic synthesis of desirable compounds. Thus, it is an object of the present invention to provide a method and compositions for isolating DNA and DNA fragments encoding enzymes relevant to the production of pharmaceutically active molecules such as antibiotic biosynthesis enzymes.

SUMMARY OF THE INVENTION

We have now identified degenerate primers which hybridize with various classes of antibiotic biosynthesis genes, and have used such primers to amplify fragments of DNA from soil and lichen extracts. Cloning and sequencing of the amplified products showed that these products included a variety of novel and previously uncharacterized antibiotic biosynthesis gene sequences, the products of which have the potential to be active as antibiotics, immunosuppressors, antitumor agents, etc. Thus, antibiotic biosynthesis genes can be recovered from soil by a method in accordance with the present invention comprising the steps of:

(a) combining a soil-derived sample with a pair of amplification primers under conditions suitable for polymerase chain reaction amplification, wherein the primer set is a degenerate primer set selected to hybridize with conserved regions of known antibiotic biosynthetic pathway genes, for example Type I and Type II polyketide synthase genes, isopenicillin N synthase genes, and peptide synthetase genes;

(b) cycling the combined sample through a plurality of amplification cycles to amplify DNA complementary to the primer set; and (c) isolating the amplified DNA.

DETAILED DESCRIPTION OF THE INVENTION

In accordance with the present invention, antibiotic biosynthesis genes can be recovered from soil and lichens by a method comprising the steps of:

(a) combining a humic or lichen-derived sample with a pair of amplification primers under conditions suitable for polymerase chain reaction amplification, wherein the primer set is a degenerate primer set selected to hybridize with conserved regions of an antibiotic biosynthesis gene;

(b) cycling the combined sample through a plurality of amplification cycles to amplify DNA complementary to the primer set; and (c) isolating the amplified DNA.

As used in the specification and claims of this application, the term "humic or lichen-derived sample" encompasses any sample containing the DNA found in lichens or in samples of humic materials including soil, mud, peat moss, marine sediments, and effluvia from hot springs and thermal vents in accessible form for amplification, substantially without alteration of the natural ratios of such DNA in the sample. One exemplary form of a humic sample is a sample obtained by performing direct lysis as described by Barns et al., *Proc. Nat'l Acad. Sci. USA* 91:1609–1613 (1994) on a soil sample and then purifying the total DNA extract by column chromatography. Related extraction methods can be applied to the isolation of community DNA from other environmental sources. See, Trevors et al., eds. *Nucleic Acids in the Environment*, Springer Lab Manual (1995). Lichen-derived samples may be prepared from foliose lichens by the method of fungal DNA extraction described by Miao et al., *Mol. Gen. Genet.* 226: 214–223 (1991). Specific non-limiting procedures for isolation of DNA from humic and lichen samples are set forth in the examples herein.

The humic or lichen-derived sample is combined with at least one, and optionally with several pairs of amplification primers under conditions suitable for polymerase chain reaction amplification. Polymerase chain-reaction (PCR) amplification is a well known process. The basic procedure, which is described in U.S. Pat. No. 4,683,202 and 4,683,195, which are incorporated herein by reference, makes uses of two amplification primers each of which hybridizes to a different one of the two strands of a DNA duplex. Multiple cycles of primer extension using a polymerase enzyme and denaturation are used to produce additional copies of the DNA in the region between the two primers. In the present invention, PCR amplification can be performed using any suitable polymerase enzyme, including Taq polymerase and Thermo Sequenase™.

The amplification primers employed in the method of the invention are degenerate primer sets selected to hybridize with conserved regions of known antibiotic biosynthetic genes, for example Type I and Type II polyketide synthase genes, isopenicillin N synthase genes, and peptide synthetase genes. Each degenerate primer set of the invention includes multiple primer species which hybridize with one DNA strand, and multiple primer species which hybridize with the other DNA strand. All of the primer species within a degenerate primer set which bind to the first strand are the same length, and hybridize with the same target region of the DNA. These primers all have very similar sequences, but have a few bases different in each species to account for the observed variations in the target region. For this reason, they are called degenerate primers. Similarly, all of the primers within a degenerate primer set which bind to the second strand are the same length, hybridize with the same target region of the DNA, and have very similar sequences with a few bases different in each species to account for the observed variations in the target region.

The degenerate primer sets of the invention are selected to hybridize to highly conserved regions of known antibiotic biosynthesis genes in such a way that they flank a region of several hundred (e.g. 300) or more base pairs such that amplification leads to the selective reproduction of DNA spanning a substantial portion of the antibiotic biosynthesis gene. Selection of primer sets can be made based upon published sequences for classes of antibiotic biosynthesis genes.

For example, for amplification of Type I polyketide synthase genes, we have designed primers based upon the conserved sequences of six beta-ketoacyl carrier protein synthase domains of the erythromycin gene cluster. Donadio et al., *Science* 252: 675–679 (1991); Donadio and Staver, *Gene* 126: 147–151 (1993). These primers have the sequences
5'-GC(C/G) (A/G)T(G/C) GAC CCG CAG CG CGC-3' [SEQ ID No. 1]
and
5'-GAT (C/G)(G/A)C GTC CGC (G/A)TT (C/G)GT (C/G) CC-3' [SEQ ID No. 2].

The expected size of the PCR product is 1.2 kilobase pairs. Other degenerate primer sets for Type I and Type II polyketide synthetase genes could be determined from sequence information available in Hutchinson and Fujii, *Ann. Rev. Microbiol.* 49: 201–238 (1995).

Type II polyketide synthase gene clusters are characterized by the presence of chain length factor genes which are arranged at the 3'-end of the ketosynthase genes. Primers were designed based on one conserved region near the 3'-end of the ketosynthase gene and one at the middle portion of the chain length factor gene. The sequences of one suitable set of amplification primers are:
5' CT(C/G)AC(G/C)(G/T)(C/G)GG(C/G)CGIAC(C/G)GC (C/G)AC(C/G)CG-3' SEQ ID No. 3
and
5' GTT(C/G)AC(C/G)GCGTAGAACCA(C/G)GCGAA-3' SEQ ID No. 4

The expected size of the PCR product was 0.5 kilobase pairs. An alternative set of degenerate primers has the sequence
5'-TTCGG(C/G)GGITTCCAG(T/A)(C/G)IGC(C/G)ATG SEQ ID No. 5
and
5'-TC(C/G)A(G/T)(C/G)AG(C/G)GC(C/G)AI(C/G)GA(C/G)TCGTAICC SEQ ID No. 6.

These primers were designed based upon consensus sequences for the regions flanking the Ks$_\beta$ (chain length factor) genes. The consensus sequences are available from Hutchinson and Fujii, supra.

Primers were designed for beta-lactam biosynthetic genes on the basis of the conserved sequences of a number of isopenicillin N synthase genes as described in Aharanowitz et al., *Ann. Rev. Microbiol.* 46: 461–495 (1992). These primers have the sequences
5'-GG(C/G/T) TC(C/G) GG(C/G) TT(C/T) TTC TAC GC-3' [SEQ ID No.7]
and
5'-CCT (C/G)GG TCT GG(A/T) A(C/G)A G(C/G)A CG-3' [SEQ ID No.8].

The expected size of the PCR product is 570 base pairs. Other degenerate primer sets could be determined from sequence information available in Jensen and Demain, "Beta-Lactams" in *Genetics and Biochemistry of Antibiotic Production* (L.C. Vining and C, Studdard, eds.), pp 239–268, Butterworth-Heinemann, Newton, Mass. (1995).

For isolation of peptide synthetase genes, primers based on two of the conserved core sequences within the functional domains of peptide synthetase genes as described by Turgay and Marahiel, *Peptide Res.* 7: 238–241 (1994) were utilized. These primers had the sequence
5'-ATCTACAC(G/C)TC(G/C)GGCAC(G/C)AC(G/C) GGCAAGCC(G/C)AAGGG-3' SEQ ID No. 9
and
5'-A(A/T)IGAG(T/G)(C/G)ICCICC(G/C)(A/G)(A/G)(G/C) I(A/C)GAAGAA-3' SEQ ID No. 10

The expected size of the PCR product is 1.2 kilobase pairs.

PCR amplification can also be used for isolating lichen-derived antibiotic biosynthesis genes and gene fragments. For isolation of Type I polyketide synthase genes from lichens, the primer set used was previously described by Keller et al. in *Molec. Appl. to Food Safety Involving Toxic Microorganisms*, J. L. Richard, ed., pp. 2630277 (1995), and had the following sequences.
5'-MGIGARGCIYTIGCIATGGAYCCICARCARMG SEQ ID No. 11
and
5'-GGRTCNCCIARYTGIGTICCIGTICCRTGIGC SEQ ID No. 12

The expected size of the PCR product is approximately 0.7 to 0.9 kilobases. Actual products evaluated ranged in size from 637 to 809 nucleotides (not including the 61 nt due to the primers).

Once the primers and the sample are cycled through sufficient thermal cycles to selectively amplify antibiotic biosynthetic DNA in the sample (generally around 25 cycles or more), the amplified DNA is isolated from the amplification mixture. Isolation can be accomplished in a variety of ways. For example, the PCR products can be isolated by electrophoresis on an agarose or polyacrylamide gel, visualized with a stain such as ethidium bromide and then excised from the gel for cloning. Primers modified with an affinity binding moiety such as biotin may also be used during the amplification step, in which case the affinity binding moiety can be used to facilitate the recovery. Thus, in the case of biotinylated primers, the amplified DNA can be recovered from the amplification mixture by coupling the biotin to a streptavidin-coated solid support, for example Dynal streptavidin-coated magnetic beads.

It will be appreciated that the DNA obtained as a result of this isolation will not generally be of a single type because of the degeneracy of the primers and the complexity of the initial sample. Thus, although these steps are sufficient to recover antibiotic biosynthesis genes from soil or lichen, it is preferable to further separate and characterize the individual species of amplified DNA.

This further separation and characterization can be accomplished by inserting the amplified DNA into an expression vector and cloning in a suitable host. The specific combination of vectors and hosts will be understood by persons skilled in the art, although bacterial expression vectors and bacterial hosts are generally preferred. Individual clones are then picked and the sequence of the cloned plasmid determined. While random selection has been employed successfully, selection of antibiotic biosynthesis gene-containing clones can be facilitated by screening using hybridization with DNA probes based on conserved sequences or by overlay of bacterial clones with an antibiotic-sensitive test strain.

Once the sequence of the cloned DNA is determined, it can be screened against existing libraries of nucleotide and protein sequences for confirmation as an antibiotic biosynthetic gene or gene fragment. Amplified DNA so-identified can be used in several ways. First, the amplified DNA, or distinctive portions thereof, can be used to as probes to screen libraries constructed from humic-derived or lichen DNA to facilitate the identification and isolation of full length antibiotic biosynthetic genes. Once isolated, these genes can be expressed in readily cultivated surrogate hosts, such as a Streptomyces species for soil-derived genes or an Aspergillus species for lichen-derived genes. General procedures for such expression are known in the art, for example from Fujii et al., *Molec. Gen. Genet.* 253: 1010 (1996) and Bedford et al., *J. Bacteriol.* 177: 4544–4548 (1995), which are incorporated herein by reference. Second, amplified DNA which is different from previously known DNA can be used to generate hybrid antibiotic biosynthesis genes using the procedures described by McDaniel et al, *Nature* 375: 549–554 (1995); Stachelhaus et al., *Science* 269: 69–72 (1995); and Stachelhaus et al, *Biochem, Pharmacol.* 52: 177–186 (1996). In these procedures, the novel DNA sequences isolated using the method of the invention are spliced into a known antibiotic gene to provide an expressible sequence encoding a complete gene product.

Using the method of the invention, a number of unique nucleotide sequences have been identified and characterized. The sequences and the biosynthetic polypeptides/proteins for which they encode, given by sequence ID Nos. 13 to 80, are a further aspect of the present invention.

EXAMPLE 1

Total DNA was extracted from soil samples by a direct lysis procedure as described by Barns et al. (1994). The high molecular weight DNA (>20 kb) in the extract was separated on a Sephadex G200 column (Pharmacia, Uppsala, Sweden) as described by Tsai and Olson, *Appl. Environ. Microbiol.* 58: 2292–2295 (1992).

The DNA extract (10–50 ng template DNA) was added to an amplification mixture (total volume 100 μl) containing 20 mM Tris-HCl (pH 8.4), 50 mM KCl, 2 mM $MgCl_2$, 200 μM of each deoxynucleotide triphosphate, 25 pmol of each Type I polyketide primer (Seq ID Nos 1 and 2) and 5.0 units of Taq polymerase (BRL Life Technologies, Gaithersburg, Md.). The mixture was then thermally cycled for 30 cycles in a MJ Research PTC-100 thermocycler using the following program:

denaturation 93° C. 60 seconds annealing 60° C. 30 seconds extension 72° C. 90 seconds The PCR products were then electrophoresed in 1% agarose gels and stained with ethidium bromide to visualize the DNA bands. Bands containing PCR product of the expected size were excised from the gel and purified using a Qiaex Gel Extraction kit (Qiagen GmBH). The purified DNA was ligated to pCRII (Invitrogen) to generate a clone library using *E. coli* INVαF competent cells. 18 clones were chosen at random from the library and sequenced using a Taq Dye Terminator Cycle Sequencing Kit and an Applied Biosystem DNA sequencer model 373. The sequencing primers used included the universal M13 (−20) forward primer, the M13 reverse primer and primers designed from the sequence data obtained. DNA sequences were translated into partial amino acid sequences using a software package from Geneworks (Intelligenetics, Inc.) with further manual adjustments and sent to the NCBI database by e-mail at blast@ncbi.nlm.nih.gov for comparison against protein databases. Altschul et al., "Basic Local Alignment Tool", *J. Mol. Biol.* 215: 403–410 (1990).

Blast analysis of the 18 clones pointed to 12 unique sequences that were not identical to each other or to published sequences. Seq. ID No. 13 shows the complete DNA sequence of a representative unique clone (Clone ksfs). Seq. ID No. 14 shows the translated amino acid sequence of this clone. The greatest homology as determined by a Blast analysis is indicated to be Type I polyketide synthases. Similar results were obtained on the Blast search of the other 11 unique clones based upon partial sequences which were determined.

EXAMPLE 2

The experiment of Example 1 was repeated using isopenicillin N synthase gene primers (Seq ID Nos. 7 and 8). The thermal cycling program was changed to include 60 second extension periods at 72° C., but otherwise the experimental conditions were the same. Twelve clones were picked at random and yielded one unique sequence that was not identical to published sequences. The complete sequence of this clone (Clone ipnsfs) is shown in Seq. ID. No. 15 and the translated amino acid sequence in Seq. ID No. 16. The BLAST search indicated greatest homology for this sequence with isopenicillin N synthases.

EXAMPLE 3

The experiment of Example 1 was repeated using peptide synthetase primers (Seq. ID Nos 9 and 10). The amplification mixture was changed to a 50 ul volume containing 10 to 50 ng of template DNA, 20 mM $(NH_4)_2SO_4$, 74 mM Tris-HCl (pH 8.8), 1.5 mM $MgCl_2$, 0.01% Tween 20, 200 μM of each deoxynucleotide triphosphate, 25 pmol of each primer, 0.25% skim milk and 0.4 units of Ultra Therm DNA Polymerase (Bio/Can Scientific, Mississauga, Ontario). The mixture was thermocycled for 30 cycles using the following program:

denaturation 95° C. 60 seconds annealing 52° C. 60 seconds extension 72° C. 120 seconds.

Thirty clones containing a 1.2 kb insert have been partially sequenced. The BLAST analysis of the 30 clones pointed to 28 unique sequences that were not identical to each other or to published sequences. Varying degrees of homology to known peptide synthase genes were seen. Seq. ID No. 17 shows the complete DNA sequence of representative clone (ps32). Seq. ID No. 18 shows the translated amino acid sequence of this clone. Based on a Blast search of these sequences, the greatest homology is to a peptide synthase gene such as the pristinamycin synthase gene from *Streptomyces pristinaespiralis* and Bacillus sp. peptide synthetase genes such as gramicidin S synthase and surfactin synthetase. Stachelhaus and Marahiel, *FEMS Micro. Letters* 125: 3–14 (1995); Turgay et al., *Mol. Micro* 6: 529–546 (1992).

Sequence ID Nos. 81 to 94 show an additional 7 unique sequences (nucleic acid and translated amino acid sequences) of 1.2 kb PCR products amplified from soil DNA samples using these primers. These sequences have been named ps 2, ps 3, ps 7, ps 10, ps 24, ps 25 and ps 30. The sequences are unique in that they are all different from each other and from ps 32, and while they show greatest homology to peptide synthetase sequences in the databases searched by BLAST analysis, they do not match any known sequence. Within each, the conserved motifs (TGD, KIRGXRIEL, NGK) common to peptide synthetase domains as described by Turgay and Marahiel (1994) can be identified. Descriptive information of the clones follows:

Clone ps 2, 1204 bp, with conserved motifs SGD, KIRGFRIEL, NGK, 67% G+C

Clone ps 3, 1178 bp, with conserved motifs TGD, KIRGSRIEL, NGK, 59% G+C

Clone ps 7, 1222 bp with conserved motifs TGD, KIRGYRIEL, NGK, 55.5% G+C

Clone ps 10, 1171 bp with conserved motifs TGD, KIRGHRIEL, NLK, 63% G+C

Clone ps 24, 1190 bp with conserved motifs TGD, KIRGHRIAM, NQK, 56% G+C

Clone ps 25, 1178 bp with conserved motifs TGD, KLRGYRIEL, NDK 68% G+C

Clone ps 30, 1200 bp with conserved motifs TGD, KVRGFRIEP, NGK, 64.5% G+C

Clone ps 32, 1172 bp with conserved motifs TGD, KIRGFRIEL, SGK, 67% G+C

EXAMPLE 4

The experiment of example 1 was repeated using the Type II polyketide synthase primers given by Seq. ID. Nos. 3 and 4. PCR amplification was carried out in a total volume of 50 ul containing 50 ng of soil DNA, 20 mM Tris-HCl (pH 8.4), 50 mM KCl, 2 mM $MgCl_2$, 200 uM of each deoxynucleotide triphosphate, 25 pmol of each primer and 5.0 units of Taq polymerase (BRL Life Technologies, Gaithersburg, Md.). The thermal cycling conditions included denaturations at 94° C. for 60 seconds, annealing at 58° C. for 30 seconds and extensions at 72° C. for seconds, repeated for a total of 30 cycles.

PCR amplification yielded products of the expected size of 0.5 kilobase pairs. Sequencing of 18 randomly selected clones revealed the presence of 5 unique sequence that were not identical to each other or to published sequences. Seq. ID No. 19 shows the complete DNA sequence of a representative clone (clone clf). The translated amino acid sequence of this clone is shown in Seq. ID. No. 20. In a BLAST search of this DNA sequence against the protein database, the greatest homology is indicated to chain length factor genes of the Type II polyketide synthases.

EXAMPLE 5

The experiment of Example 1 was repeated using the Type I polyketide synthase primers designed for fungal sequences. (Seq. ID. Nos. 11 and 12) PCR amplifications were carried out with lichen DNA samples from a variety of lichen species representing 11 genera prepared as described in Miao et al. (1991), supra.

PCR amplifications were carried out in a total volume of 50 ul containing approximately 10 ng of lichen DNA and 1 unit of Taq polymerase in a reaction as per Example 4. The cycling protocol was 30 cycles of denaturation at 95° C. for 60 seconds, annealing at 57° C. for 2 minutes and extensions at 72° C. for 2 minutes.

Forty seven clones with inserts of the expected size have been partially sequenced. The sequences all show homology to Type I fungal polyketide synthase genes but are all distinct from each other and from known sequences. Seq. ID. No. 21 shows the complete DNA sequence of a 637 base pair product amplified from DNA extracted from the lichen *Xanthoparmelia cumberlandia* (clone Xa.cum.6A). The translated amino acid sequence is shown in Seq. ID. No. 22. The greatest homology as determined by Blast analysis is indicated to fungal Type I polyketide synthase genes.

Sequence ID Nos. 29 and 30 show the DNA sequence and conceptual amino acid sequence, respectively, for a further clone Xa.cum.6H isolated in this experiment. Sequences of DNA and the corresponding amino acid sequences for seven other lichen samples, *Leptogium corniculatum* (Seq. ID Nos. 31–42), *Parmelia sulcata* (Seq. ID Nos. 43–50); *Peltigera neopolydactyla* (Seq. ID Nos. 51–60); *Pseudocyphellaria anthrapsis* (Seq. ID Nos. 61–62); *Siphula ceratities* (Seq. ID. Nos. 63–66); *Thamnolia vermicularis* (Seq. ID Nos. 67–68); and *Usnea florida* (Seq. ID Nos. 69–80). Each of these sequences showed homology by Blast analysis to fungal Type I polyketide synthase.

EXAMPLE 6

The experiment of Example 5 was repeated on DNA from the lichen *Solorina crocea* using the degenerate peptide synthetase primers of Example 3. Freshly collected lichen (approximately 1.2 g) was washed in running tap water to remove conspicuous soil and field detritis, and then further cleaned under a dissecting microscope. The cleaned sample was then gently shaken in a 50 ml tube containing about 40 ml of 0.2% SDS for at least 30 minutes and rinsed thoroughly with water. Excess surface water was blotted from the washed, hydrated lichen, and the sample was frozen at −80° C. for at least 15 minutes then vacuum dried at room temperature for 4 hours. The lichen was ground in liquid nitrogen using a mortar and pestle to produce a lichen powder for use in preparing DNA extracts.

To prepare the DNA extracts, 0.28 g of lichen powder was placed into 18 2-ml microfuge tubes, and each aliquot was mixed with 1.25 ml isolation buffer (150 mM EDTA, 50 mM Tris pH 8, 1% sodium lauroyl sarcosine) and extracted for 1 hour at 62° C. The samples were centrifuged for three minutes to pellet cellular debris and a cloudy supernatant was decanted into new microfuge tubes. Each sample of the supernate was mixed with 750 $\mu$l 7.5 M ammonium acetate, incubated on ice for 30 minutes and centrifuged for five minutes at 16,000×g to precipitate proteins. The supernatant fluid was saved in new microfuge tubes and nucleic acids were precipitated with 0.6 volumes of isopropanol overnight at 4° C. Samples were centrifuged for five minutes at 16,000×g to pellet nucleic acids. The pellets were dissolved in TE containing RNAse (18 $\mu$g total) at 50° C. for 45 minutes. The solutions were then extracted with an equal volume of TE saturated phenol:chloroform (1:1), and again with chloroform. DNA in the aqueous phase was precipitated with 0.1 M sodium acetate and two volumes of ethanol at −20° C. for 2 hours, and then pelleted by centrifugation for five minutes at 16,000×g. The DNA pellet was washed with 75% ethanol, vacuum dried at room temperature for 3 minutes and then dissolved in TE. The final amount of DNA recovered was approximately 70 $\mu$g according to fluorometric measurement.

Two clones containing the expected 1.2 kb insert were sequenced and found to contain the same sequence shown in Seq. ID. No. 23. Seq. ID. No. 24 shows the translated amino acid sequence. The sequence is distinct, with greatest homology as determined by Blast analysis to the peptide synthase module of the cyanobacterium *Microcyctis aeruginosa*.

EXAMPLE 7

The experiment of example 4 was repeated using the Type II polyketide synthase primers given by Seq. ID. Nos. 5 and 6. Three starting samples were used for recovery of Type II polyketide synthase genes: two uncharacterized strains of Streptomyces (strains WEC 68A and WEC 71B) which had been shown to contain Type II polyketide synthase genes, and a soil sample obtained from a forest area near Vancouver, British Columbia. The soil sample was prepared using the basic protocol from Holben et al, *Appl. Environ. Microbiol.* 54: 703–711 (1988) with variations in parameters such as mix time to adjust for the individual characteristics of the soil samples.

Streptomyces genomic DNA preparations suitable for PCR amplification were prepared from the mycelia harvested from a 50 ml culture in tryptic soy broth (Difco) which had been grown for 3 days at 300 C. The mycelia were collected by centrifugation at 2500×g for 10 minutes, the pellets were washed in 10% v/v glycerol and the washed pellets were frozen at –200C. The size of the pellets will vary with different strains; for extraction, 1 g samples were suspended in 5 ml TE buffer (10 mM Tris-HCl, pH 8.0, 1 mM EDTA) in a 50 ml screw cap Oakridge tube and lysozyme (to 10 mg/ml) and RNase (to 40 ug/g) were added. Following incubation at 300 C. for 45 min. a drop of each suspension was transferred to a microscope slide, one drop of 10% SDS was added and the suspension was checked for complete clearing and increased viscosity, indicating lysis. Most strains lyse with this incubation time, but incubation in lysozyme may be continued if necessary. (For strains which are very resistant to lysis, small amounts of DNA suitable for PCR amplification may often be prepared on a FastPrep™ instrument as described below.) Following confirmation of sufficient incubation time in lysozyme, 1.2 ml of 0.5 M EDTA, pH 8.0 was added to the suspension and mixed gently then 0.13 ml of 10 mg/ml Proteinase K (Gibco/BRL) solution was added and incubated for 5 min. at 300 C. 0.7 ml of 10% SDS was added, mixed gently by tilting, then incubated again at 300 C. for 2 hours. Following lysis, three successive phenol/chloroform extractions were performed by adding a volume equivalent to the aqueous phase each time of a 1:1 mixture of ultrapure Tris buffer saturated phenol (Gibco/BRL) and chloroform. The aqueous phase was recovered each time following centrifugation at 2500×g for 10 min. in a shortened (i.e.wide bore) Pasteur pipet to minimize shearing; DNA was precipitated from the final aqueous phase with the addition of 0.1 volume of 3M Na acetate, pH 4.8 and 1 volume of isopropanol at room temperature. DNA was spooled from the solution onto a sealed Pasteur pipet, rinsed in ice cold 70% ethanol and solubilized in 0.5 ml TE buffer overnight at room temperature. DNA yields (as determined spectrophotometrically) typically range from 1 to 3 mg from 1 g of mycelia.

An alternative method for the preparation of small amounts of Streptomyces DNA suitable for PCR amplification has been found to be useful for strains resistant to lysis or when a faster method is desirable. This method makes use of the FastPrep™ instrument (Savant) and the methods and kit supplied by BIO 101 (Bio/Can Scientific, Mississauga, Canada). A 2 ml aliquot from a 20 ml, 3 day culture in tryptic soy broth is pelleted in a 2 ml microfuge tube and the size of the mycelial pellet is estimated. "Small" pellets are resuspended in 100 ul of sterile distilled water; larger pellets are resuspended in 200–300 ul of water. 200 ul of suspension is transferred to a homogenization tube from the kit. Following the manufacturer's protocol for the preparation of DNA from medium hard tissue, the large bead is added to this tube (which already contains a small bead) and 1 ml of solution CLS-TC from the kit is added and the samples are processed in the instrument for 10 seconds at speed setting 4.5. Samples are then spun 15 min. at 10,000×g at 40 C. and 600 ul of the supernatant is transferred to a clean microfuge tube, 400 ul of Binding Matrix is added and mixed gently, then the sample is spun for 1 min. as above. The supernatant is discarded while the pellet is resuspended in 500 ul SEWS-M and transferred to a SPIN™ Filter unit. This is spun for 1 minute, the contents of the catch tube are discarded and the unit is spun again to dry. The filter unit is transferred to a new microfuge tube and DNA is eluted from the matrix in 100 ul DES which is left on the filter for 2–3 min. at room temperature. Eluted DNA is collected by spinning once again and this DNA is now ready to use in PCR amplifications. Due to components of the final solution, DNA prepared by this method is difficult to quantify. Typically 1 ul or 1/10 ul of this eluate is suitable as a template for PCR; larger quantities may be inhibitory to the PCR polymerase.

PCR amplification was carried out in a total volume of 50 ul containing 50 ng of DNA) 5% DMSO, 1.25 mM MgCl$_2$, 200 uM of each deoxynucleotide triphosphate, 0.5 ug of each primer and 5.0 units of Taq polymerase (BRL Life Technologies, Gaithersburg, Md.). The thermal cycling started with a 'touch-down' sequence, lowering the annealing temperature from 65° C. to 58° C. over the course of 8 cycles. The temperature of the annealing step was then maintained at 58° C. for a further 35 cycles. The overall cycle used was: denaturation at 94° C. for 45 seconds, annealing at 65° C. to 58° C. for 1 minute and extension at 72° C. for 2 minutes. The size of the amplified fragments was expected to be approximately 1.5 kb.

Amplification of the two Streptomyces strains produced DNA fragments of the expected size (1482 bp and 1538 bp). Open reading frame analysis of the two sequences revealed the presence of a set of three ORFs each, corresponding to the 3'-ends of the putative $Ks_\alpha$-subunit genes (50 to 60 bp), possible full-length $Ks_\beta$ genes (approx. 1.2 kb) and the first halves of potential ACP genes (approx 100 bp). In each sequence, the first and second ORFs were linked by a stop codon overlap typical of $Ks_{\alpha,\beta}$ gene pair junctions and a possible indication of tight coexpression through translational coupling. The two $Ks_\beta$ genes were separated from the downstream ACP genes by a short spacer, again consistent with the expected gene organization.

Two clones were selected from among clones created using the soil DNA as a source which were found to produce 1.5 kb inserts. These inserts were sequenced and found to exhibit similarity to known $KS_\beta$ genes with three ORFs as described above. The translated amino acid sequences of the four genes are shown in Sequence ID Nos 25 to 28.

The four putative $KS_\beta$ genes had G+C content over 70% which is typical for the coding regions of Actinomycete genes. Results of data base searches established that the deduced products of all four ORFs were similar to known $KS_\beta$ gene products from Type II polyketide synthases but they did not match any known sequences.

EXAMPLE 8

DNA can be extracted from large volumes of soil in accordance with the following procedure. Place dry soil into a sterile blender with 0.2% sodium pyrophosphate (100 ml/100 grams of soil). The pH of the sodium pyrophosphate solution should be about 10, although some variation to account for the characteristics of the soil may be appropriate. The mixture is blended for 30 seconds, decanted into centrifuges bottles and then centrifuged for 15 minutes at 100×g at 4° C. The supernatant is decanted, filtered two times through cheese cloth and saved. The pelleted soil is extracted an additional two times using the same procedure.

After the extractions, the pooled supernatants are centrifuged for 15 minutes at 10,500×g and the pellets are collected. The pellet may be incubated for 6 hours at 55° C. in pre-germination medium (0.5% w/v yeast extract (Difco), 0.5% w/v casamino acids (Difco) with 0,005 M $CaCl_2$ and 0.025 M TES, pH 8.0 (added separately from sterile stock after autoclaving other components)) and then repelleted, or it may be used directly. In either case, the pellet (approximately 30–200 mg) is mixed with 5 ml 1×TE (pH 8.0), 500 µl 0.5M EDTA (pH 8.0) and 500 µl–20 mg/ml lysozyme in 1×TE (pH 8.0) and incubated for 30 minutes at 37° C. 500 µl of 20% SDS and 100 µl–1% proteinase K in TE and 1% SDS are then added and the mixture is vortexed gently before incubating for 60 minutes at 55° C. or overnight at 37° C.

The incubated mixture is combined with 10 ml 20% polyvinylpyrrolidone (avg. MW=40,000) and incubated for 10 minutes at 70° C. One-half volume of 7.5 M ammonium acetate (stored at –20° C.) is then added, the resulting mixture is placed for 10 minutes on a low speed shaker, and then centrifuged for 20 minutes at 18,5000×g. The supernatant is combined with 1 volume of isopropanol and incubated for 30 minutes at –20° C. before centrifuging for 20 minutes at 18,500×g. The pellet from this centrifugation is washed in 70% ethanol, and centrifuged for 10 minutes at 18,500×g. The pellet from this final centrifugation is collected and air dried.

EXAMPLE 9

To extract DNA from small amounts of soil the following procedure can be used. Combine soil (approx 1 g) with 1 ml distilled water, vortex to suspend and pellet at 19,000×g for 5 minutes. After removing the supernatant, freeze/thaw the samples twice by either of the following techniques (a) –20° C. freezer, 30 minutes, followed by 50–60° C. water bath (2 minutes), repeated 2 times; or (b) quick freeze in EtOH-dry ice bath (dip in until frozen, approx one minute) followed by 60° C. water bath (2 minutes), repeated 2 times. The pellets are then suspended in 350 µl TE buffer (pH 8.0), 50 µl 0.5 M EDTA and 50 µl–20 mg/ml lysozyme in TE buffer, vortexed and incubated at 37° C. for 30 minutes in a water bath. 50 µl of 20% SDS and 10 µl 1% Proteinase K/1% SDS in TE buffer is added, vortexed, and incubated for one hour at 55° C. or overnight at 37° C. One-tenth volume of 20% polyvinylpyrrolidone (avg. MW=40,000) is then added and incubated at 70° C. for 10 minutes. One-half volume of 7.5 M ammonium acetate (stored at –20° C.) is added, the tubes are shaken at low speed for ten minutes and then centrifuged at 19,000×g for 20 minutes. The supernatant is collected using pipets with cut tips to avoid shearing DNA, combined with one volume of isopropanol, mixed gently, and stored at –20° C. for 30 minutes or 4° C. overnight. The DNA is then collected as a pellet by centrifugation at 19,000×g for 10 minutes. The resulting pellet is washed with 0.5 ml of 70% ethanol (stored at –20° C.) and then air or vacuum dried. The dried DNA is then dissolved in 50–150 ul of TE buffer, incubated at 4° C. for one hour and then heated to 60° C. for 10 minutes to facilitate dissolving DNA. The resulting solutions are stored at –20° C. until use.

We claim:

1. A method for recovery of DNA comprising a nucleotide sequence of a portion of a gene that encodes a protein that is involved in antibiotic synthesis, from humic materials or lichen, comprising the steps of:

(a) combining a DNA sample derived from humic material or lichen with a set of oligonucleotide primers in a reaction mixture which comprises a DNA polymerase and deoxynucleotide triphosphates, wherein the primers are capable of hybridizing to nucleotide sequences that encode conserved regions of a protein, the protein being involved in antibiotic synthesis;

(b) amplifying the DNA flanked by the nucleotide sequences that encode conserved regions of the protein in the reaction mixture by polymerase chain reaction; and (c) isolating the amplified DNA from the reaction mixture.

2. The method according to claim 1, wherein the set of olilonucleotide primers comprises oligonucleotide primers that hybridize to nucleotide sequences encoding a protein that is involved in polyketide synthesis.

3. The method according to claim 2, wherein the set of oligonucleotide primers comprises oligonucleotide primers that consist essentially of the nucleotide sequence set forth in SEQ ID NO:1, oligonucleotide primers that consist essentially of the nucleotide sequence set forth in SEQ ID NO:2, or both.

4. The method according to claim 2, wherein the set of oligonucleotide primers comprises oligonucleotide primers that consist essentially of the nucleotide sequence set forth in SEQ ID NO:3, oligonucleotide primers that consist essentially of the nucleotide sequence set forth in SEQ ID NO: 4, or both.

5. The method according to claim 2, wherein the set of oligonucleotide primers comprises oligonucleotide primers that consist essentially of the nucleotide sequence set forth in SEQ ID NO: 5, oligonucleotide primers that consist essentially of the nucleotide sequence set forth in SEQ ID NO: 6, or both.

6. The method according to claim 2, wherein the set of oligonucleotide primers comprises oligonucleotide primers that consist essentially of the nucleotide sequence set forth in SEQ ID NO: 11, oligonucleotide primers that consist essentially of the nucleotide sequence set forth in SEQ ID NO: 12, or both.

7. The method according to claim 1, wherein the set of oligonucleotide primers comprises oligonucleotide primers that hybridize to nucleotide sequences encoding an isopenicillin N synthase gene.

8. The method according to claim 7, wherein the set of oligonucleotide primers comprises oligonucleotide primers that consist essentially of the nucleotide sequence set forth in SEQ ID NO:7, oligonucleotide primers that consist essentially of the nucleotide sequence set forth in SEQ ID NO:8. or both.

9. The method according to claim 1, wherein the set of oligonucleotide primers comprises oligonucleotide primers that hybridize to nucleotide sequences encoding a polyketide synthase gene.

10. The method according to claim 9, wherein the set of oligonucleotide primers comprises oligonucleotide primers that consist essentially of the nucleotide sequence set forth in SEQ ID NO:9, oligonucleotide primers that consisting essentially of the nucleotide sequence set forth in SEQ ID NO: 10, or both.

11. The method according to claim 1, wherein the sample comprises DNA extracted from a soil sample.

12. The method according to claim 1, wherein the sample is a lichen-derived sample.

13. The method according to claim 1, further comprising the steps of cloning the amplified DNA into a host organism, and isolating the cloned DNA.

14. The method according to claim 13, wherein the host organism is *E. coli*.

15. An oligonucleotide primer consisting essentially of the sequence as defined in SEQ ID NO:1, SEQ ID NO:2, SEQ ID NO:3, SEQ ID NO:4, SEQ ID NO:5, SEQ ID NO:6, SEQ ID NO:7 or SEQ ID NO:8.

16. A composition comprising two oligonucleotide primers, said oligonucleotide primers each consisting essentially of the sequence as defined in (i) SEQ ID NO: 1 or SEQ ID NO:2; (ii) SEQ ID NO:3 or SEQ ID NO:4; (iii) SEQ ID NO:5 or SEQ ID NO:6; or (iv) SEQ ID NO:7 or SEQ ID NO:8.

* * * * *